US007104961B2

(12) United States Patent
Starobin et al.

(10) Patent No.: US 7,104,961 B2
(45) Date of Patent: *Sep. 12, 2006

(54) METHOD AND SYSTEM FOR EVALUATING CARDIAC ISCHEMIA WITH AN EXERCISE PROTOCOL

(75) Inventors: Joseph M. Starobin, Greensboro, NC (US); Yuri B. Chernyak, Lexington, MA (US)

(73) Assignee: Mediwave Star Technology, Inc., Greensboro, NC (US)

( * ) Notice: Subject to any disclaimer, the term of this patent is extended or adjusted under 35 U.S.C. 154(b) by 652 days.

This patent is subject to a terminal disclaimer.

(21) Appl. No.: 10/308,639

(22) Filed: Dec. 3, 2002

(65) Prior Publication Data

US 2003/0149370 A1    Aug. 7, 2003

Related U.S. Application Data

(63) Continuation-in-part of application No. 10/036,005, filed on Dec. 26, 2001, now Pat. No. 6,648,830, which is a continuation-in-part of application No. 09/891,910, filed on Jun. 26, 2001, now Pat. No. 6,652,467, which is a continuation-in-part of application No. 09/603,286, filed on Jun. 26, 2000, now Pat. No. 6,361,503.

(51) Int. Cl.
*A61B 5/0452* (2006.01)

(52) U.S. Cl. .................................... 600/508

(58) Field of Classification Search ........ 600/508–510, 600/515–521
See application file for complete search history.

(56) References Cited

U.S. PATENT DOCUMENTS

| 4,870,974 A | 10/1989 | Wang ........................ 128/700 |
| 5,020,540 A | 6/1991 | Chamoun .................. 128/703 |
| 5,117,834 A | 6/1992 | Kroll et al. ................. 128/705 |

(Continued)

OTHER PUBLICATIONS

Sarma et al, "Hysteresis in the Human RR-QT Relationship During Exercise and Recovery", Pace vol. 10, May-Jun. 1987, pp. 485-491.*

(Continued)

*Primary Examiner*—George R. Evanisko
(74) *Attorney, Agent, or Firm*—Myers Bigel Sibley & Sajovec, PA

(57) ABSTRACT

A method of assessing cardiac ischemia in a subject to provide a measure of cardiac or cardiovascular health in that subject is described herein. The method comprises the steps of: (a) collecting a first RR-interval data set from said subject during a stage of gradually increasing heart rate up to a predetermined heart rate of at least 130 beats per minute; (b) collecting a second RR-interval data set from said subject during a stage of gradually decreasing heart rate; (c) comparing said first RR-interval data set to said second RR-interval data set to determine the difference between said data sets; and (d) generating from said comparison of step (c) a measure of cardiac ischemia during stimulation in said subject, wherein a greater difference between said first and second data sets indicates greater cardiac ischemia and lesser cardiac or cardiovascular health in said subject.

43 Claims, 21 Drawing Sheets

U.S. PATENT DOCUMENTS

| | | | | |
|---|---|---|---|---|
| 5,148,812 | A | 9/1992 | Verrier et al. | 128/704 |
| 5,323,783 | A | 6/1994 | Henkin et al. | 128/703 |
| 5,419,338 | A | 5/1995 | Sarma et al. | 128/703 |
| 5,560,370 | A | 10/1996 | Verrier et al. | 128/705 |
| 5,713,367 | A | 2/1998 | Arnold et al. | 128/704 |
| 5,792,065 | A | 8/1998 | Xue et al. | 600/516 |
| 5,794,623 | A | 8/1998 | Forbes | 128/702 |
| 5,827,195 | A | 10/1998 | Lander | 600/509 |
| 5,842,997 | A | 12/1998 | Verrier et al. | 600/518 |
| 5,891,047 | A | 4/1999 | Lander et al. | 600/516 |
| 5,921,940 | A | 7/1999 | Verrier et al. | 600/518 |
| 5,951,484 | A | 9/1999 | Hoium et al. | 600/515 |
| 6,361,503 | B1 * | 3/2002 | Starobin et al. | 600/508 |
| 6,648,829 | B1 * | 11/2003 | Starobin et al. | 600/508 |
| 6,648,830 | B1 * | 11/2003 | Starobin et al. | 600/508 |
| 6,652,467 | B1 * | 11/2003 | Starobin et al. | 600/508 |
| 6,656,126 | B1 * | 12/2003 | Starobin et al. | 600/508 |
| 6,663,572 | B1 * | 12/2003 | Starobin et al. | 600/508 |
| 6,768,919 | B1 * | 7/2004 | Starobin et al. | 600/520 |

OTHER PUBLICATIONS

Arnold et al.; *The dependence on heart rate of the human ventricular action potential duration*, Cardiovascular Research, 16, 547-551 (1982).

Chernyak et al.; *Class of Exactly Solvable Models of Excitable Media*, Phys. Rev. Lett,. 80:25, 5675-56787 (1998).

Chernyak et al.; *Where do dispersion curves end? A basic question in theory of excitable media*, Phys. Rev. E,. 58:4, 4108-4111 (1998).

Ciavolella et al.; *Exponential Fit of QT Interval-Heart Rate Relation During Exercise Used to Diagnose Stress-induced Myocardial Ischemia*, Journal of Electrocariology, 24:2, 145-153 (1991).

Cole et al.; *Heart-Rate Recovery Immediately After Exercise As A Predictor of Mortality*, The New England Journal of Medicine, 341:18, 1351-1357 (Oct. 1999).

Franz et al.; *Cycle Length Dependence of Human Action Potential Duration In Vivo: Effects of SIngle Extrastimuli, Sudden Sustained Rate Acceleration and Deceleration, and Different Steady-State Frequencies*, J. Clin. Invest,. 82, 972-979 (1988).

Froelicher, Jr. et al.; *A comparison of three maximal treadmill exercise protocols*, Journal of Applied Physiology, 36:6, 720-725 (1974).

Hintze et al.; *Prognostic Properties of QT/RR Dynamics in Survivors of Myocardial Infarction with Reduced Systolic Function*, NASPE Annual Meeting, Washington, D.C. (May 17-20, 2000).

Jonnalegedda et al.; *An Exponential Formula for Heart Rate Dependence of QT Interval During Exercise and Cardiac Pacing in Humans: Reevaluation of Bazett's Formula*, Am J Cardiol, 54, 103-108 (1984).

Jonnalegedda et al.; *Hysteresis in the Human RR-QT Relationship During Exercise and Recovery*, PACE 10, 485-491 (1997).

Krahn, M.D. et al.; *Hysteresis of the RT Interval With Exercise: A New Marker for the Long-QT Syndrome?*, Circulation, 96, 1551-1556 (1997).

Lau et al.; *Hysteresis of the ventricular paced QT interval in response to abrupt changes in pacing rate*, Cardiovascular Research, 22, 67-72 (1988).

Starobin et al.; *The role of a critical excitation length scale in dynamics of reentrant cardiac arrhythmias*, Herzschr Elektrophys, 10, 119-136 (Month Unknown, 1999).

Surawicz; *Will QT Dispersion Play a Role in Clinical Decision-Making?*, J Cardiovascular Electrophysiol, 7, 777-784 (1996).

Swan et al.; *Rate adaption of QT intervals during and after exercise in children with congenital long QT syndrome*, European Heart Journal, 19, 508-513 (1998).

Takahashi et al.; *Paradoxically Shortened QT Interval after a Prolonged Pause*, PACE, 21, 1476-1479 (1998).

Pierpoint et al.; *Heart Rate recovery post-exercise as an index of parasympathetic activity*, Journal of the Autonomic Nervous System, 80, 169-174 (May 12, 2000).

International Search Report, International Application No. PCT/US01/20391 dated Aug. 20, 2001.

* cited by examiner $$\frac{fu}{ft} = \frac{f^2u}{fx^2} - i(u,v)$$

$$\frac{fv}{ft} = \varepsilon g(u,v)$$

METHOD AND SYSTEM FOR EVALUATING CARDIAC ISCHEMIA WITH AN EXERCISE PROTOCOL

RELATED APPLICATIONS

This application is a continuation-in-part of application Ser. No. 10/036,005, filed Dec. 26, 2001, now U.S. Pat. No. 6,648,830 which in turn is a continuation-in-part of application Ser. No. 09/891,910, filed Jun. 26, 2001, now U.S. Pat. No. 6,652,467 which in turn is a continuation-in-part of U.S. Pat. No. 6,361,503, filed as application Ser. No. 09/603,286, filed Jun. 26, 2000, the disclosures of all of which are incorporated by reference herein in their entirety.

FIELD OF THE INVENTION

The present invention relates to non-invasive high-resolution diagnostics of cardiac ischemia based on processing of body-surface electrocardiogram (ECG) data. The invention's quantitative method of assessment of cardiac ischemia may simultaneously indicate both cardiac health itself and cardiovascular system health in general.

BACKGROUND OF THE INVENTION

Heart attacks and other ischemic events of the heart are among the leading causes of death and disability in the United States. In general, the susceptibility of a particular patient to heart attack or the like can be assessed by examining the heart for evidence of ischemia (insufficient blood flow to the heart tissue itself resulting in an insufficient oxygen supply) during periods of elevated heart activity. Of course, it is highly desirable that the measuring technique be sufficiently benign to be carried out without undue stress to the heart (the condition of which might not yet be known) and without undue discomfort to the patient. It is also desirable that the measuring technique be useful for patients of varying degrees of health, including patients without detectable ischemia, those with moderate levels of ischemia, and patients with coronary artery disease.

The cardiovascular system responds to changes in physiological stress by adjusting the heart rate, which adjustments can be evaluated by measuring the surface ECG R-R intervals. The time intervals between consecutive R waves indicate the intervals between the consecutive heartbeats (RR intervals). This adjustment normally occurs along with corresponding changes in the duration of the ECG QT intervals, which characterize the duration of electrical excitation of cardiac muscle and represent the action potential duration averaged over a certain volume of cardiac muscle (FIG. 1). Generally speaking, an average action potential duration measured as the QT interval at each ECG lead may be considered as an indicator of cardiac systolic activity varying in time.

Recent advances in computer technology have led to improvements in automatic analyzing of heart rate and QT interval variability. It is well known now that the QT interval's variability (dispersion) observations performed separately or in combination with heart rate (or RR-interval) variability analysis provides an effective tool for the assessment of individual susceptibility to cardiac arrhythmias (B. Surawicz, J. Cardiovasc. Electrophysiol, 1996, 7, 777–784). Applications of different types of QT and some other interval variability to susceptibility to cardiac arrhythmias are described in U.S. Pat. No. 5,020,540 by Chamoun, 1991; Wang U.S. Pat. No. 4,870,974, 1989; Kroll et al. U.S. Pat. No. 5,117,834, 1992; Henkin et al. U.S. Pat. No. 5,323,783, 1994; Xue et al. U.S. Pat. No. 5,792,065, 1998; Lander U.S. Pat. No. 5,827,195, 1998; Lander et al. U.S. Pat. No. 5,891,047, 1999; Hojum et al. U.S. Pat. No. 5,951,484, 1999).

It was recently found that cardiac electrical instability can be also predicted by linking the QT-dispersion observations with the ECG T-wave alternation analysis (Verrier et al., U.S. Pat. Nos. 5,560,370; 5,842,997; 5,921,940). This approach is somewhat useful in identifying and managing individuals at risk for sudden cardiac death. The authors report that QT interval dispersion is linked with risk for arrhythmias in patients with long QT syndrome. However, QT interval dispersion alone, without simultaneous measurement of T-wave alternation, is said to be a less accurate predictor of cardiac electrical instability (U.S. Pat. No. 5,560,370 at column 6, lines 4–15).

Another application of the QT interval dispersion analysis for prediction of sudden cardiac death is developed by J. Sarma (U.S. Pat. No. 5,419,338). He describes a method of an autonomic nervous system testing that is designed to evaluate the imbalances between both parasympathetic and sympathetic controls on the heart and, thus, to indicate a predisposition for sudden cardiac death.

The same author suggested that an autonomic nervous system testing procedure might be designed on the basis of the QT hysteresis (J. Sarma et al., *PACE* 10, 485–491 (1988)). Hysteresis between exercise and recovery was observed, and was attributed to sympatho-adrenal activity in the early post-exercise period. Such an activity was revealed in the course of QT interval adaptation to changes in the RR interval during exercise with rapid variation of the load.

The influence of sympatho-adrenal activity and the sharp dependence of this hysteresis on the time course of abrupt QT interval adaptation to rapid changes in the RR interval dynamics radically overshadows the method's susceptibility to the real ischemic-like changes of cardiac muscle electrical parameters and cardiac electrical conduction. Therefore, this type of hysteresis phenomenon would not be useful in assessing the health of the cardiac muscle itself, or in assessing cardiac ischemia.

A similar sympatho-adrenal imbalance type hysteresis phenomenon was observed by A. Krahn et al. (*Circulation* 96, 1551–1556 (1997)(see Figure 2 therein)). The authors state that this type of QT interval hysteresis may be a marker for long-QT syndrome. However, long-QT syndrome hysteresis is a reflection of a genetic defect of intracardiac ion channels associated with exercise or stress-induced syncope or sudden death. Therefore, similar to the example described above, although due to two different reasons, it also does not involve a measure of cardiac ischemia or cardiac muscle ischemic health.

A conventional non-invasive method of assessing coronary artery diseases associated with cardiac ischemia is based on the observation of morphological changes in a surface electrocardiogram during physiological exercise (stress test). A change of the ECG morphology, such as an inversion of the T-wave, is known to be a qualitative indication of ischemia. The dynamics of the ECG ST-segments are continuously monitored while the shape and slope, as well as ST-segment elevation or depression, measured relative to an average base line, are altering in response to exercise load. A comparison of any of these changes with average values of monitored ST segment data provides an indication of insufficient coronary blood circulation and developing ischemia. Despite a broad clinical acceptance and the availability of computerized Holter monitor-like devices for automatic ST segment data processing, the diagnostic value of this method is limited due to its low sensitivity and low resolution. Since the approach is specifically reliable primarily for ischemic events associated with relatively high coronary artery occlusion, its widespread use often results in false positives, which in turn may lead to unnecessary and more expensive, invasive cardiac catheterization.

Relatively low sensitivity and low resolution, which are fundamental disadvantages of the conventional ST-segment depression method, are inherent in such method's being based on measuring an amplitude of a body surface ECG signal, which signal by itself does not accurately reflect changes in an individual cardiac cell's electrical parameters normally changing during an ischemic cardiac event. A body surface ECG signal is a composite determined by action potentials aroused from discharge of hundred of thousands of individual excitable cardiac cells. When electrical activity of excitable cells slightly and locally alters during the development of exercise-induced local ischemia, its electrical image in the ECG signal on the body surface is significantly overshadowed by the aggregate signal from the rest of the heart. Therefore, regardless of physiological conditions, such as stress or exercise, conventional body surface ECG data processing is characterized by a relatively high threshold (lower sensitivity) of detectable ischemic morphological changes in the ECG signal. An accurate and faultless discrimination of such changes is still a challenging signal processing problem.

Accordingly, there is a need to provide techniques for detecting and measuring cardiac ischemia in a patient that may be non-invasive, not unduly uncomfortable or stressful, and which may be implemented with relatively simple equipment for patients having various health conditions, and can be sensitive to low levels of ischemia.

SUMMARY OF THE INVENTION

The present invention is based on the finding that, for all individuals (not just patients afflicted with coronary artery disease), if the patient's heart rate reaches a sufficiently high level (which level will vary from individual to individual), then slowly or rapidly diminishing or even discontinuing the exercise (or other load causing the increased heart rate) will not evoke a clear or substantial sympatho-adrenal response in the subject. As a result, the exercise can be considered to be quasi-stationary; data may be collected from such a patient; and cardiac ischemia and/or cardiovascular health may be assessed in the patient in accordance with the techniques described herein.

Embodiments of the present invention may overcome deficiencies in the conventional ST-segment analysis. An RR- and/or QT-RR interval data set may be used to assess cardiovascular health in a subject under certain conditions. Embodiments of the present invention may be useful to assess cardiovascular health in patients with varying degrees of ischemia such as patients with coronary artery disease ("CAD"), patients with moderate levels of ischemia, as well as patients without detectable ischemia. An RR- and/or QT-RR interval data set can be collected during stages of varying workloads and heart rates. The data collected during a recovery period after a relatively high workload and/or heart rate period may be analyzed as an indication of cardiovascular health.

More specifically, the subject's heart rate at its peak during heavy workload may be sufficiently high such that a quasi-stationary increasing heart rate period and subsequent recovery period are observed. The recovery period can involve decreasing the subject's heart rate by reducing workload gradually or by abruptly stopping exercise workload. The reduction of workload may be preceded by a "cool down" stage of reduced workload. The RR- and/or QT-RR interval data sets collected during the stage of relatively high workload and heart rate and the subsequent recovery stage in which workload is decreased or eliminated may be analyzed to indicate the cardiovascular health of the patient.

While the present invention is described herein primarily with reference to the use of QT- and RR-interval data sets, it will be appreciated that the invention may be implemented in simplified form with the use of RR-interval data sets alone. For use in the claims below, it will be understood that the term "RR-interval data set" is intended to be inclusive of both the embodiments of QT-RR and RR-interval data sets and RR-interval data sets alone, unless expressly subject to the proviso that the data set does not include a QT-interval data set.

A first aspect of the present invention is a method of assessing cardiac ischemia in a subject to provide a measure of cardiovascular health in that subject. The method comprises the steps of:

(a) collecting a first RR-interval data set from said subject during a stage of gradually increasing heart rate up to a predetermined threshold of, for example, at least 130 beats per minute;

(b) collecting a second RR-interval data set from said subject during a stage of gradually decreasing heart rate;

(c) comparing said first RR-interval data set to said second RR-interval data set to determine the difference between said data sets; and (d) generating from said comparison of step (c) a measure of cardiac ischemia during stimulation in said subject, wherein a greater difference between said first and second data sets indicates greater cardiac ischemia and lesser cardiac or cardiovascular health in said subject.

During the periods of gradually increasing and gradually decreasing heart rate the effect of the sympathetic, parasympathetic, and hormonal control on formation of the hysteresis loop is sufficiently small, minimized or controlled so that the ischemic changes are readily detectable. This maintenance is achieved by effecting a sufficiently high peak heart rate that the increasing and decreasing heart rate periods are quasi-stationary.

Another aspect of the present invention is a computer program product for assessing cardiac ischemia in a subject to provide a measure of cardiac or cardiovascular health in that subject. The computer program product includes a computer usable storage medium having computer readable program code embodied in the medium. The computer readable program code includes:

(a) computer readable program code for collecting a first RR-interval data set from said subject during a stage of gradually increasing heart rate up to a predetermined threshold of, for example, at least 130 beats per minute;

(b) computer readable program code for collecting a second RR-interval data set from said subject during a stage of gradually decreasing heart rate;

(c) computer readable program code for comparing said first RR-interval data set to said second RR-interval data set to determine the difference between said data sets; and (d) computer readable program code for generating from said comparing in said computer readable program code (c) a measure of cardiac ischemia during stimulation in said subject, wherein a greater difference between said first and second data sets indicates greater cardiac ischemia and lesser cardiac or cardiovascular health in said subject.

The present invention is explained in greater detail in the drawings herein and the specification set forth below.

DETAILED DESCRIPTION OF THE PREFERRED EMBODIMENTS

Figures 1, 2A:
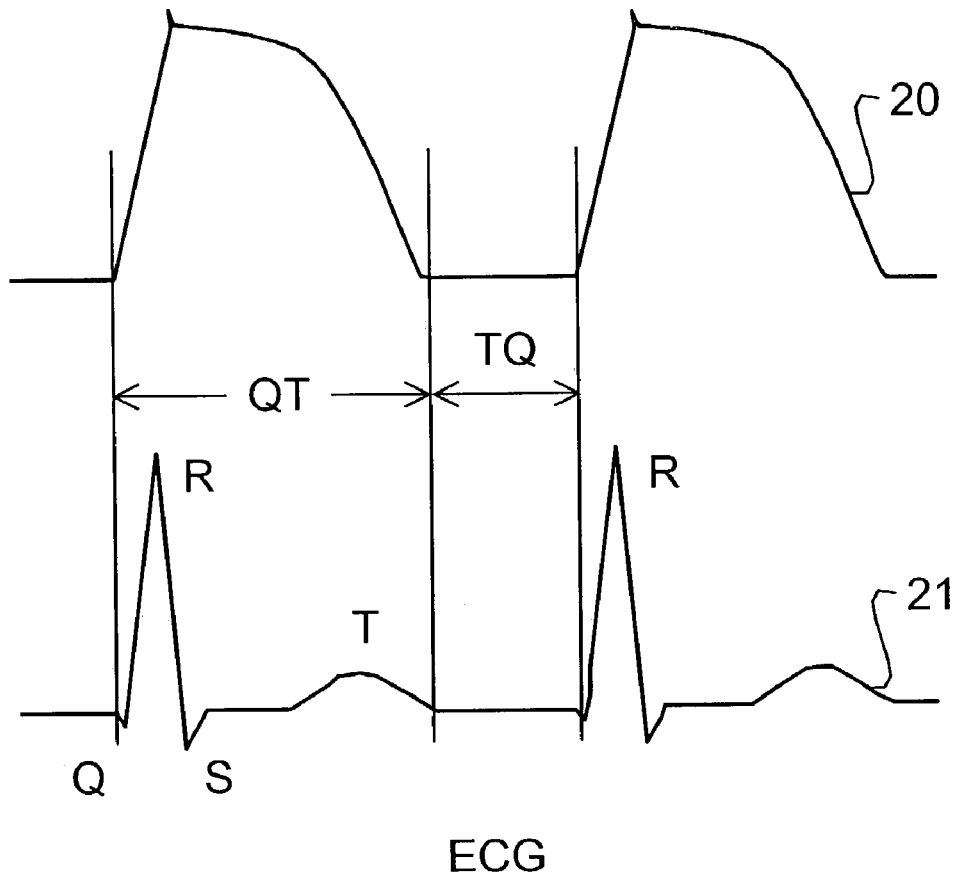
FIG. 1 is a schematic graphic representation of the action potential in cardiac muscle summed up over its volume and the induced electrocardiogram (ECG) recorded on a human's body surface.
FIG. 2A depicts the equations used in a simplified mathematical model of periodic excitation.

The present invention is explained in greater detail below. This description is not intended to be a detailed catalog of all the different manners in which particular elements of the invention can be implemented, and numerous variations will be apparent to those skilled in the art based upon the instant disclosure.

As will be appreciated by one of skill in the art, certain aspects of the present invention may be embodied as a method, data processing system, or computer program product. Accordingly, certain aspects of the present invention may take the form of an entirely hardware embodiment, an entirely software embodiment, or an embodiment combining software and hardware aspects. Furthermore, certain aspects of the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices.

Certain aspects of the present invention are described below with reference to flowchart illustrations of methods, apparatus (systems), and computer program products. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

Computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

Computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

1. Definitions.

"Cardiac ischemia" refers to a lack of or insufficient blood supply to an area of cardiac muscle. Cardiac ischemia usually occurs in the presence of arteriosclerotic occlusion of a single or a group of coronary arteries. Arteriosclerosis is a product of a lipid deposition process resulting in fibro-fatty accumulations, or plaques, which grow on the internal walls of coronary arteries. Such an occlusion compromises blood flow through the artery, which reduction then impairs oxygen supply to the surrounding tissues during increased physiological need—for instance, during increased exercise loads. In the later stages of cardiac ischemia (e.g., significant coronary artery occlusion), the blood supply may be insufficient even while the cardiac muscle is at rest. However, in its earlier stages such ischemia is reversible in a manner analogous to how the cardiac muscle is restored to normal function when the oxygen supply to it returns to a normal physiological level. Thus, ischemia that may be detected by the present invention includes episodic, chronic and acute ischemia.

"Exercise" as used herein refers to voluntary skeletal muscle activity of a subject that increases heart rate above that found at a sustained stationary resting state. Examples of exercise include, but are not limited to, cycling, rowing, weight-lifting, walking, running, stair-stepping, etc., which may be implemented on a stationary device such as a treadmill or in a non-stationary environment.

"Exercise load" or "load level" refers to the relative strenuousness of a particular exercise, with greater loads or load levels for a given exercise producing a greater heart rate in a subject. For example, load may be increased in weight-lifting by increasing the amount of weight; load may be increased in walking or running by increasing the speed and/or increasing the slope or incline of the walking or running surface; etc.

"Gradually increasing" and "gradually decreasing" an exercise load refers to exercise in which the subject is caused to perform an exercise under a plurality of different sequentially increasing or sequentially decreasing loads. The number of steps in the sequence can be infinite so the terms gradually increasing and gradually decreasing loads include continuous load increase and decrease, respectively.

"Hysteresis" refers to a lagging of the physiological effect when the external conditions are changed.

"Hysteresis curves" refer to a pair of curves in which one curve reflects the response of a system to a first sequence of conditions, such as gradually increasing heart rate, and the other curve reflects the response of a system to a second sequence of conditions, such as gradually decreasing heart rate. Here both sets of conditions are essentially the same—i.e., consist of the same (or approximately the same) steps—but are passed in different order in the course of time. A "hysteresis loop" refers to a loop formed by the two contiguous curves of the pair.

"Electrocardiogram" or "ECG" refers to a continuous or sequential record (or a set of such records) of a local electrical potential field obtained from one or more locations outside the cardiac muscle. This field is generated by the combined electrical activity (action potential generation) of multiple cardiac cells. The recording electrodes may be either subcutaneously implanted or may be temporarily attached to the surface of the skin of the subject, usually in the thoracic region. An ECG record typically includes the single-lead ECG signal that represents a potential difference between any two of the recording sites including the site with a zero or ground potential.

"Non-quasi-stationary intervening rest", when used to refer to a stage following increased cardiac stimulation, refers to a stage of time initiated by a sufficiently abrupt decrease in heart stimulation (e.g., an abrupt decrease in exercise load) so that it evokes a clear sympatho-adrenal response. Thus, a non-quasi-stationary intervening rest stage is characterized by a rapid sympatho-adrenal adjustment (as further described in Example 8 below), and the inclusion of an intervening rest stage precludes the use of a quasi-stationary exercise (or stimulation) protocol (as further described in Example 9 below). On the other hand, "quasi-stationary intervening rest" refers to a stage of time initiated by a decrease in heart stimulation that does not evoke a clear sympatho-adrenal response. Examples of conditions under which a quasi-stationary intervening rest occurs includes a stage of increasing heart rate up to a predetermined threshold that is sufficiently high such that subsequent intervening rest is quasi-stationary.

A "predetermined threshold heart rate" refers to a range of heart rates that are sufficiently high such that a subsequent reduction in heart rate, e.g., due to decreased exercise load or the elimination of exercise load, is quasi-stationary. The predetermined threshold heart rate can be at least 130, 140, 150, 160 or more beats per minute. In addition, the predetermined threshold heart rate can be defined by the following formula:

$$PT=(220\pm V \text{ bpm})-\text{age};$$

where PT is the predetermined threshold heart rate, V is 10, 15, 20, 25, or 30, bpm is beats per minute, and age is the age of said subject. The threshold heart rate may correspond to a work load of between about 5, 10 or 20W and about 30, 40, or 60W for a coronary artery disease patient and a work load of between about 80, 90 or 100W to about 130, 150 or 170W for a non-coronary artery disease patient. The threshold heart rate may also be determined by observing the amount of stress that a patient experiences during exercise such that the threshold heart rate coincides with a degree of stress that is close to the maximum safe degree of stress.

"Quasi-stationary conditions" refer to any situation in which a gradual change in the external conditions and/or the physiological response it causes occurs slower than any corresponding adjustment due to sympathetic/parasympathetic and hormonal control. If the representative time of the external conditions variation is denoted by $\tau_{ext}$, and $\tau_{int}$ is a representative time of the fastest of the internal, sympathetic/parasympathetic and hormonal control, then "quasi-stationary conditions" indicates $\tau_{ext} \gg \tau_{int}$ (e.g., $\tau_{ext}$ is at least about two, three, four or five times greater than $\tau_{int}$). Abrupt changes in exercise load may be either quasi-stationary or non-quasi-stationary. "A non-quasi-stationary abrupt change" refers to a situation opposite quasi-stationary conditions corresponding to a sufficiently fast change in the external conditions as compared with the rate sympathetic/parasympathetic and hormonal control—that is, it requires that $\tau_{ext} \ll \tau_{int}$ (e.g., $\tau_{ext}$ is at least about two, three, for our five times less than $\tau_{int}$). "A quasi-stationary abrupt change" refers to a relatively fast change in exercise load that is nonetheless quasi-stationary-, for example, because the change is preceded by a sufficiently high exercise load such that a slower, quasi-stationary recovery period is observed.

"QT- and RR-data set" refers to a record of the time course of an electrical signal comprising action potentials spreading through cardiac muscle. Any single lead ECG record incorporates a group of three consecutive sharp deflections usually called a QRS complex and generated by the propagation of the action potential's front through the ventricles. In contrast, the electrical recovery of ventricular tissue is seen on the ECG as a relatively small deflection known as the T wave. The time interval between the cardiac cycles (i.e., between the maxima of the consecutive R-waves) is called an RR-interval, while the action potential duration (i.e., the time between the beginning of a QRS complex and the end of the ensuing T-wave) is called a QT-interval. Alternative definitions of these intervals can be equivalently used in the framework of the present invention. For example, an RR-interval can be defined as the time between any two similar points, such as the similar inflection points, on two consecutive R-waves, or any other way to measure cardiac cycle length. A QT-interval can be defined as the time interval between the peak of the Q-wave and the peak of the T wave. It can also be defined as the time interval between the beginning (or the center) of the Q-wave and the end of the ensuing T-wave defined as the point on the time axis (the base line) at which it intersects with the linear extrapolation of the T-wave's falling branch and started from its inflection point, or any other way to measure action potential duration. An ordered set of such interval durations simultaneously with the time instants of their beginnings or ends which are accumulated on a beat to beat basis or on any given beat sampling rate basis form a corresponding QT- and RR-interval data set. Thus, a QT- and RR-interval data set will contain two QT-interval related sequences $\{T_{QT,1}, T_{QT,2}, \ldots, T_{QT,n}\}$ and $\{t_1, t_2, \ldots, t_n\}$, and will also contain two RR-interval related sequences $\{T_{RR,1}, T_{RR,2}, \ldots, T_{RR,n}\}$ and $\{t_1, t_2, \ldots, t_n\}$ (the sequence $\{t_1, t_2, \ldots, t_n\}$ may or may not exactly coincide with the similar sequence in the QT data set).

In the following definitions, C[a,b] shall denote a set of continuous functions $f(t)$ on a segment [a,b]. $\{t_i\}$, i=1, 2, ..., N, denotes a set of points from [a,b], i.e. $\{t_i\}=\{t_i: a \leq t_i \leq b, i=1, 2, \ldots, N\}$ and $\{f(t_i)\}$, where $f \in C[a,b]$, denotes a set of values of the function $f$ at the points $\{t_i\}$. In matrix operations the quantities $\tau=\{t_i\}$, $y=\{f(t_i)\}$, are treated as column vectors. $E_N$ shall denote a N-dimensional metric space with the metric $R_N(x,y)$, $x,y \in E_N$. ($R_N(x,y)$ is said to be a distance between points x and y.) A (total) variation $$\overset{b}{\underset{a}{V}}[F]$$

is defined for any absolutely continuous function F from C[a,b] as the integral (a Stieltjes integral)

$$\overset{b}{\underset{a}{V}}[F(t)] \equiv \int_a^b |dF(t)| = \int_a^b |F'(t)|\, dt. \quad\quad\quad (D.1)$$

For a function F monotonic on segment [a,b] its variation is simply |F(a)−F(b)|. If a function F(t) has alternating maxima and minima, then the total variation of F is the sum of its variations on the intervals of monotonicity. For example, if the points of minima and maxima are $x_1=a, x_2, x_3, \ldots, x_k=b$ then $$\overset{b}{\underset{a}{V}}[F(t)] = \sum_{i=1}^{k-1} |F(x_i) - F(x_{i+1})|. \quad (D.2)$$

Fitting (best fitting): Let $\tilde{C}[a,b]$ be a subset of $C[a,b]$. A continuous function $f(t)$, $f \in \tilde{C}[a,b]$ is called the (best) fit (or the best fitting) function of class $\tilde{C}[a,b]$ with respect to metric $R_N$ to a data set $\{x_i, t_i\}$ (i=1, 2, ..., N) if $$R_N(\{f(t_i)\}, \{x_i\}) = \min_{f \in \tilde{C}[a,b]} \quad (D.3)$$

The minimum value of $R_N$ is then called the error of the fit. The functions $f(t)$ from $\tilde{C}[a,b]$ will be called trial functions.

In most cases $E_N$ is implied to be an Euclidean space with an Euclidean metric. The error $R_N$ then becomes the familiar mean-root-square error. The fit is performed on a subset $\tilde{C}[a,b]$ since it usually implies a specific parametrization of the trial functions and/or such constrains as the requirements that the trial functions pass through a given point and/or have a given value of the slope at a given point.

A smoother function (comparison of smoothness): Let $f(t)$ and $g(t)$ be functions from $C[a,b]$ that have absolutely continuous derivatives on this segment. The function $f(t)$ is smoother than the function $g(t)$ if $$\overset{b}{\underset{a}{V}}[f(t)] \leq \overset{b}{\underset{a}{V}}[g(t)], \quad (D.4)$$

and $$\overset{b}{\underset{a}{V}}[f'(t)] \leq \overset{b}{\underset{a}{V}}[g'(t)], \quad (D.5)$$

where the prime denotes a time derivative, and a strict inequality holds in at least one of relations (D.4) and (D.5).

A smoother set: A set $\{x_i, t_i\}$ (i=1, 2, ..., N) is smoother than the set $\{x'_j, t'_j\}$ (j=1, 2, ..., N') if the former can be fit with a smoother function $f(t)$ of the same class within the same or smaller error than the latter.

Smoothing of a data set: A (linear) transformation of a data set $(x,t) \equiv \{x_i, t_i\}$ (i=1, 2, ..., $N_0$) into another set $(y,\tau) \equiv \{y_j, \tau_j\}$ (j=1, 2, ..., $N_1$) of the form $$y = A \cdot x, \quad \tau = B \cdot t, \quad (ID.6)$$

where A and B are $N_1 \times N_0$ matrices, is called a smoothing if the latter set is smoother than the former. One can refer to $\{y_j, \tau_j\}$ as a smoothed set.

A measure of a closed domain: Let $\Omega$ be a singly connected domain on the plane $(\tau, T)$ with the boundary formed by a simple (i.e., without self-intersections) continuous curve. A measure M of such a domain $\Omega$ on the plane $(\tau, T)$ is defined as the Riemann integral $$M = \int\int_\Omega \rho(\tau, T) d\tau dT \quad (D.7)$$

where $\rho(\tau, T)$ is a nonnegative (weight) function on $\Omega$.

Note that when $\rho(\tau,T) \equiv 1$ the measure M of the domain coincides with its area, A; when $\rho(\tau,T) \equiv 1/\tau^2$, the measure, M, has the meaning of the area, A', of the domain $\Omega'$ on the transformed plane $(f,T)$, where $f=1/\tau 0$ can be understood as the heart rate since the quantity $\tau$ has the meaning of RR-interval. [The domain $\Omega'$ is the image of domain $\Omega$ under the mapping $(\tau,T) \rightarrow (1/\tau,T)$.]

2. Dispersion/Restitution Curves.

FIG. 1 illustrates the correspondence between the temporal phases of the periodic action potential (AP, upper graph, 20) generated inside cardiac muscle and summed up over its entire volume and the electrical signal produced on the body surface and recorded as an electrocardiogram (ECG, lower graph, 21). The figure depicts two regular cardiac cycles. During the upstroke of the action potential the QRS-complex is formed. It consists of three waves, Q, R, and S, which are marked on the lower panel. The recovery stage of the action potential is characterized by its fall off on the AP plot and by the T-wave on the ECG plot. One can see that the action potential duration is well represented by the time between Q and T waves and is conventionally defined as the QT interval, measured from the beginning of the Q wave to the end of the following T wave. The time between consecutive R-waves (RR interval) represents the duration of a cardiac cycle, while its reciprocal value represents the corresponding instantaneous heart rate.

Figure 2B:
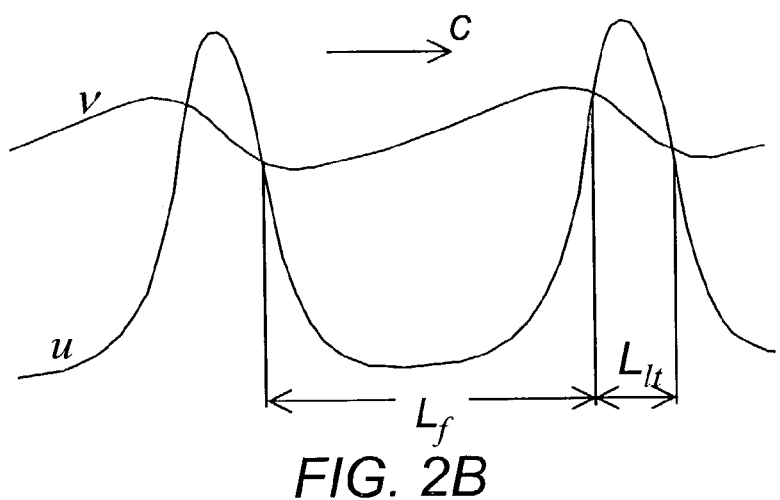
FIG. 2B depicts a periodic excitation wave (action potential, u, and instantaneous threshold, v, generated by computer using a simplified mathematical model, the equations of which are set forth in FIG. 2A.
Figure 2C:
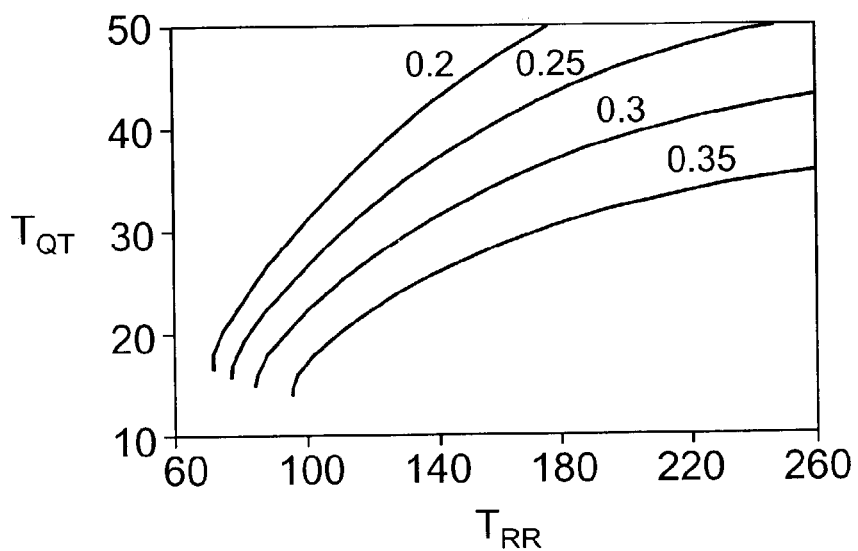
FIG. 2C depicts a family of four composite dispersion-restitution curves corresponding to four values of the medium excitation threshold.

FIG. 2 illustrates major aspects of the process of propagation of a periodic action potential through cardiac tissue and the formation of a corresponding composite dispersion-restitution curve. The tissue can be considered as a continuous medium and the propagation process as a repetition at each medium point of the consecutive phases of excitation and recovery. The former phase is characterized by a fast growth of the local membrane potential (depolarization), and the latter by its return to a negative resting value (repolarization). The excitation phase involves a very fast (~0.1 ms) decrease in the excitation threshold and the following development of a fast inward sodium current that causes the upstroke of the action potential (~1 ms). Next, during an intermediate plateau phase (~200 ms) sodium current is inactivated; calcium and potassium currents are developing while the membrane is temporarily unexcitable (i.e., the threshold is high). During the next recovery phase (~100 ms), a potassium current repolarizes the membrane so it again becomes excitable (the excitation threshold is lowered).

The complicated description of a multitude of ionic currents involved in the process can be circumvented if one treats the process directly in terms of the local membrane potential, u, and a local excitation threshold, v. Such a mathematical description referred to as the CSC model, was developed by Chernyak, Starobin, & Cohen (*Phys. Rev. Lett.*, 80, pp.5675–5678, 1998) and is presented as a set of two Reaction-Diffusion (RD) equations in panel A. The left-hand side of the first equation describes local accumulation of the electric charge on the membrane, the first term in the right-hand side describes Ohmic coupling between neighboring points of the medium, and the term i(u,v)

represents the transmembrane current as a function of the membrane potential and the varying excitation threshold ($\epsilon$ is a small constant, the ratio of the slow recovery rate to the fast excitation rate). A periodic solution (a wave-train) can be found analytically for some particular functions i(u,v) and g(u,v). The wave-train shown in panel B has been calculated for $g(u,v)=\zeta u+v_r-v$, where $\zeta$ and $v_r$ are appropriately chosen constants ($v_r$ has the meaning of the initial excitation threshold and is the main determinant of the medium excitability). The function i(u,v) was chosen to consist of two linear pieces, one for the sub-threshold region, u<v, and one for supra-threshold region, u>v. That is $i(u,v)=\lambda_r u$ when $u \leq v$, and $i(u,v)=\lambda_{ex}(u-u_{ex})$ when u>v, where $\lambda_r$ and $\lambda_{ex}$ are membrane chord conductances in the resting (u=0) and excited ($u=u_{ex}$) states, respectively. The resting state u=0 is taken as the origin of the potential scale. We used such units that $\lambda_{ex}=1$ and $u_{ex}=1$. (For details see Chernyak & Starobin, *Critical Reviews in Biomed. Eng.* 27, 359–414 (1999)).

A medium with higher excitability, corresponding to the tissue with better conduction, gives rise to a faster, more robust action potential with a longer Action Potential Duration (APD). This condition also means that a longer-lasting excitation propagates faster. Similarly, a wave train with a higher frequency propagates slower since the medium has less time to recover from the preceding excitation and thus has a lower effective excitability. These are quite generic features that are incorporated in the CSC model. In physics, the relation between the wave's speed, c, and its frequency, $f$, or its period, $T=1/f$, is called a dispersion relation. In the CSC model the dispersion relation can be obtained in an explicit form $T=F_T(c)$, where $F_T$ is a known function of c and the medium parameters. The CSC model also allows us to find a relation between the propagation speed and the APD, $T_{AP}$, in the explicit form $T_{AP}=F_{AP}(c)$, which represents the restitution properties of the medium. In the medical literature, the restitution curve is $T_{AP}$ versus diastolic interval $T_{DI}$, which differently makes a quite similar physical statement. One can consider a pair of dispersion and restitution relations $\{T=F_T(c), T_{AP}=F_{AP}(c)\}$ as a parametric representation of a single curve on the $(T, T_{AP})$-plane as shown in panel C (FIG. 2). Such a curve (relation) shall be referred to as a composite dispersion-restitution curve (relation) and can be directly obtained from an experimental ECG recording by determining the QT-RR interval data set and plotting $T_{QT}$ versus $T_{RR}$. A condition that the experimental $\{T_{QT}, T_{RR}\}$ data set indeed represents the composite dispersion-restitution relation is the requirement that the data are collected under quasi-stationary conditions. Understanding this fact is a key discovery for the present invention.

3. Testing Methods.

The methods of the present invention are primarily intended for the testing of human subjects. Virtually any human subject can be tested by the methods of the present invention, including male, female, juvenile, adolescent, adult, and geriatric subjects. The methods may be carried out as an initial screening test on subjects for which no substantial previous history or record is available, or may be carried out on a repeated basis on the same subject (particularly where a comparative quantitative indicium of an individual's cardiac health over time is desired) to assess the effect or influence of intervening events and/or intervening therapy on that subject between testing sessions.

As noted above, the method of the present invention generally comprises (a) collecting a first RR-interval data set from said subject during a stage of gradually increasing heart rate up to a predetermined threshold of at least 130 beats per minute; (b) collecting a second RR-interval data set from said subject during a stage of gradually decreasing heart rate; (c) comparing said first RR-interval data set to said second RR-interval data set to determine the difference between said data sets; and (d) generating from said comparison of step (c) a measure of cardiac ischemia during stimulation in said subject, wherein a greater difference between said first and second data sets indicates greater cardiac ischemia and lesser cardiac or cardiovascular health in said subject.

The stages of gradually increasing and gradually decreasing heart rate are carried out in a manner that maintains during both periods essentially or substantially the same stimulation of the heart by the peripheral nervous and hormonal control systems, so that it is the effect of cardiac ischemia rather than that of the external control which is measured by means of the present invention. This methodology can be carried out by a variety of techniques, including the technique of conducting two consecutive stages of gradually increasing and gradually decreasing exercise loads (or average heart rates).

The stage of gradually increasing exercise load (or increased average heart rate) and the stage of gradually decreasing exercise load (or decreased average heart rate) may be the same in duration or may be different in duration. In general, each stage is at least 3, 5, 8, or 10 minutes or more in duration. Together, the duration of the two stages may be from about 6, 10, 16 or 20 minutes in duration to about 30, 40, or 60 minutes in duration or more. The two stages are preferably carried out sequentially in time—that is, with one stage following after the other substantially immediately, without an intervening rest stage. In the alternative, the two stages may be carried out separately in time, with an intervening "plateau" stage (e.g., of from 1 to 5 minutes) during which cardiac stimulation or exercise load is held substantially constant, before the stage of decreasing load is initiated. In a particular embodiment discussed below, where the subject is not afflicted with detectable coronary artery disease, a stage of decreasing exercise load may be considered to take place during the period following a quasi-stationary abrupt stop in exercise.

The exercise protocol may include the same or different sets of load steps during the stages of increasing or decreasing heart rates. For example, the peak load in each stage may be the same or different, and the minimum load in each stage may be the same or different. In general, each stage consists of at least two or three different load levels, in ascending or descending order depending upon the stage. Relatively high load levels, which result in relatively high heart rates, can be used. The peak or predetermined threshold heart rate is sufficiently high such that subsequent resting or decreased exercise load periods are quasi-stationary. Embodiment of the present invention may be used to diagnose or test patients with varying levels of ischemia, including patients without detectable ischemia, patients with moderate ischemia, and patients with coronary artery disease.

The predetermined threshold heart rate may correspond to varying workloads for different patients depending on overall fitness and cardiac health. For example, for an athletic or trained subject, for the first or ascending stage, a first load level may be selected to require a power output of 60 to 100 or 150 watts by the subject; an intermediate load level may be selected to require a power output of 100 to 150 or 200 watts by the subject; and a third load level may be selected to require a power output of 200 to 300 or 450 watts or more by the subject. For the second or descending stage, a first load level may be selected to require a power output of 200 to 300 or 450 watts or more by the subject; an intermediate or second load level may be selected to require a power output of 100 to 150 or 200 watts by the subject; and a third load level may be selected to require a power output of 60 to 100 or 150 watts by the subject. Additional load levels may be included before, after, or between all of the foregoing load levels as desired, and adjustment between load levels can be carried out in any suitable manner, including step-wise or continuously. Increased heart rates up to the predetermined threshold heart rate may also be achieved by maintaining a single load level for a sustained period of time sufficient to reach the threshold heart rate.

In a further example, for an average subject or a subject with a history of cardiovascular disease, for the first or ascending stage, a first load level may be selected to require a power output of 20 to 40 to 75 or 100 watts by the subject; an intermediate load level may be selected to require a power output of 75 to 100 or 150 watts by the subject; and a third load level may be selected to require a power output of 125 to 200 or 300 watts or more by the subject. For the second or descending stage, a first load level may be selected to require a power output of 125 to 200 or 300 watts or more by the subject; an intermediate or second load level may be selected to require a power output of 75 to 100 or 150 watts by the subject; and a third load level may be selected to require a power output of 40 to 75 or 100 watts by the subject. As before, additional load levels may be included before, after, or between all of the foregoing load levels as desired, and adjustment between load levels can be carried out in any suitable manner, including step-wise or continuously. The predetermined threshold heart rate may also be achieved by sustained exercise at a single power output for a sufficient amount of time.

The heart rate may be gradually increased and gradually decreased by subjecting the patient to a predetermined schedule of stimulation. For example, the patient may be subjected to a gradually increasing exercise load and gradually decreasing exercise load, or gradually increasing electrical or pharmacological stimulation and gradually decreasing electrical or pharmacological stimulation, according to a predetermined program or schedule. Such a predetermined schedule is without feedback of actual heart rate from the patient. In the alternative, the heart rate of the patient may be gradually increased and gradually decreased in response to actual heart rate data collected from concurrent monitoring of said patient. Such a system is a feedback system. For example, the heart rate of the patient may be monitored during the test and the exercise load (speed and/or incline, in the case of a treadmill) can be adjusted so that the heart rate varies in a prescribed way during both stages of the test. The monitoring and control of the load can be accomplished by a computer or other control system using a simple control program and an output panel connected to the control system and to the exercise device that generates an analog signal to the exercise device. One advantage of such a feedback system is that (if desired) the control system can insure that the heart rate increases substantially linearly during the first stage and decreases substantially linearly during the second stage.

The generating step (d) may be carried out by any suitable means, such as by generating curves from the data sets (with or without actually displaying the curves), and then (i) directly or indirectly evaluating a measure (e.g., as defined in the integral theory) of the domain (e.g., area) between the hysteresis curves, a greater measure indicating greater cardiac ischemia in said subject, (ii) directly or indirectly comparing the shapes (e.g., slopes or derivatives thereof) of the curves, with a greater difference in shape indicating greater cardiac ischemia in the subject; or (iii) combinations of (i) and (ii). Specific examples are given in Example 4 below.

The method of the invention may further comprise the steps of (e) comparing the measure of cardiac ischemia during exercise to at least one reference value (e.g., a mean, median or mode for the quantitative indicia from a population or subpopulation of individuals) and then (f) generating from the comparison of step (e) at least one quantitative indicium of cardiovascular health for said subject. Any such quantitative indicium may be generated on a one-time basis (e.g., for assessing the likelihood that the subject is at risk to experience a future ischemia-related cardiac incident such as myocardial infarction or ventricular tachycardia), or may be generated to monitor the progress of the subject over time, either in response to a particular prescribed cardiovascular therapy, or simply as an ongoing monitoring of the physical condition of the subject for improvement or decline (again, specific examples are given in Example 4 below). In such a case, steps (a) through (f) above are repeated on at least one separate occasion to assess the efficacy of the cardiovascular therapy or the progress of the subject. A decrease in the difference between said data sets from before said therapy to after said therapy, or over time, indicates an improvement in cardiac health in said subject from said cardiovascular therapy. Any suitable cardiovascular therapy can be administered, including but not limited to, aerobic exercise, muscle strength building, change in diet, nutritional supplement, weight loss, smoking cessation, stress reduction, pharmaceutical treatment (including gene therapy), surgical treatment (including both open heart and closed heart procedures such as bypass, balloon angioplasty, catheter ablation, etc.) and combinations thereof.

The therapy or therapeutic intervention may be one that is approved or one that is experimental. In the latter case, the present invention may be implemented in the context of a clinical trial of the experimental therapy, with testing being carried out before and after therapy (and/or during therapy) as an aid in determining the efficacy of the proposed therapy.

4. Testing Apparatus.

Figure 3:
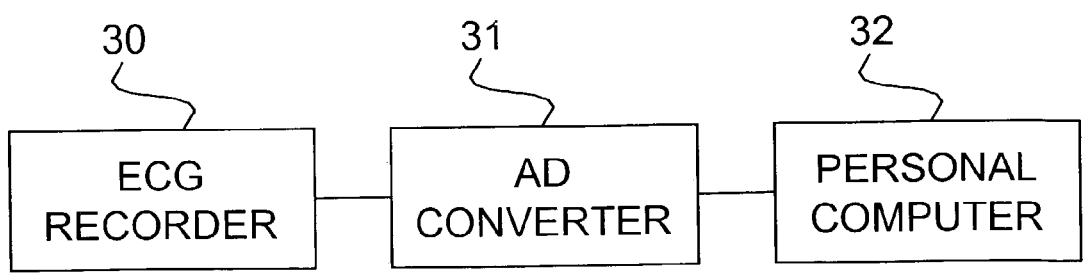
FIG. 3 is a block diagram of an apparatus for carrying out the present method.

FIG. 3 provides an example of the apparatus for data acquisition, processing and analysis by the present invention. Electrocardiograms are recorded by an ECG recorder 30, via electrical leads placed on a subject's body. The ECG recorder may be, for example, a standard multi-lead Holter recorder or any other appropriate recorder. The analog/digital converter 31 digitizes the signals recorded by the ECG recorder and transfers them to a personal computer 32, or other computer or central processing unit, through a standard external input/output port. The digitized ECG data can then be processed by standard computer-based waveform analyzer software. Composite dispersion-restitution curves and a cardiac or cardiovascular health indicium or other quantitative measure of the presence, absence or degree of cardiac ischemia can then be calculated automatically in the computer through a program (e.g., Basic, Fortran, C++, etc.) implemented therein as software, hardware, or both hardware and software.

Figure 4A:
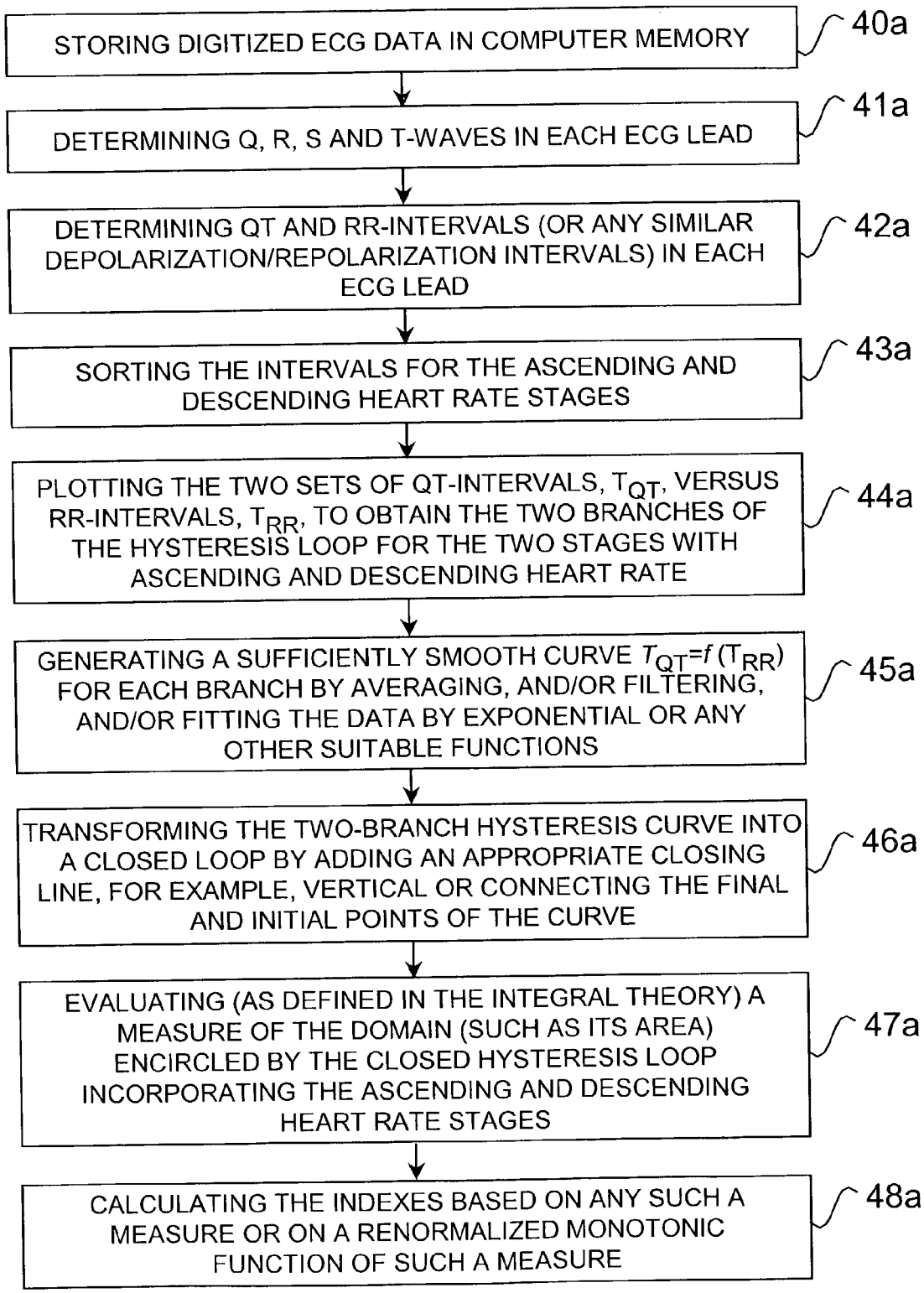
FIG. 4A is a block diagram of the processing steps for data acquisition and analysis of the present invention.
Figure 4B:
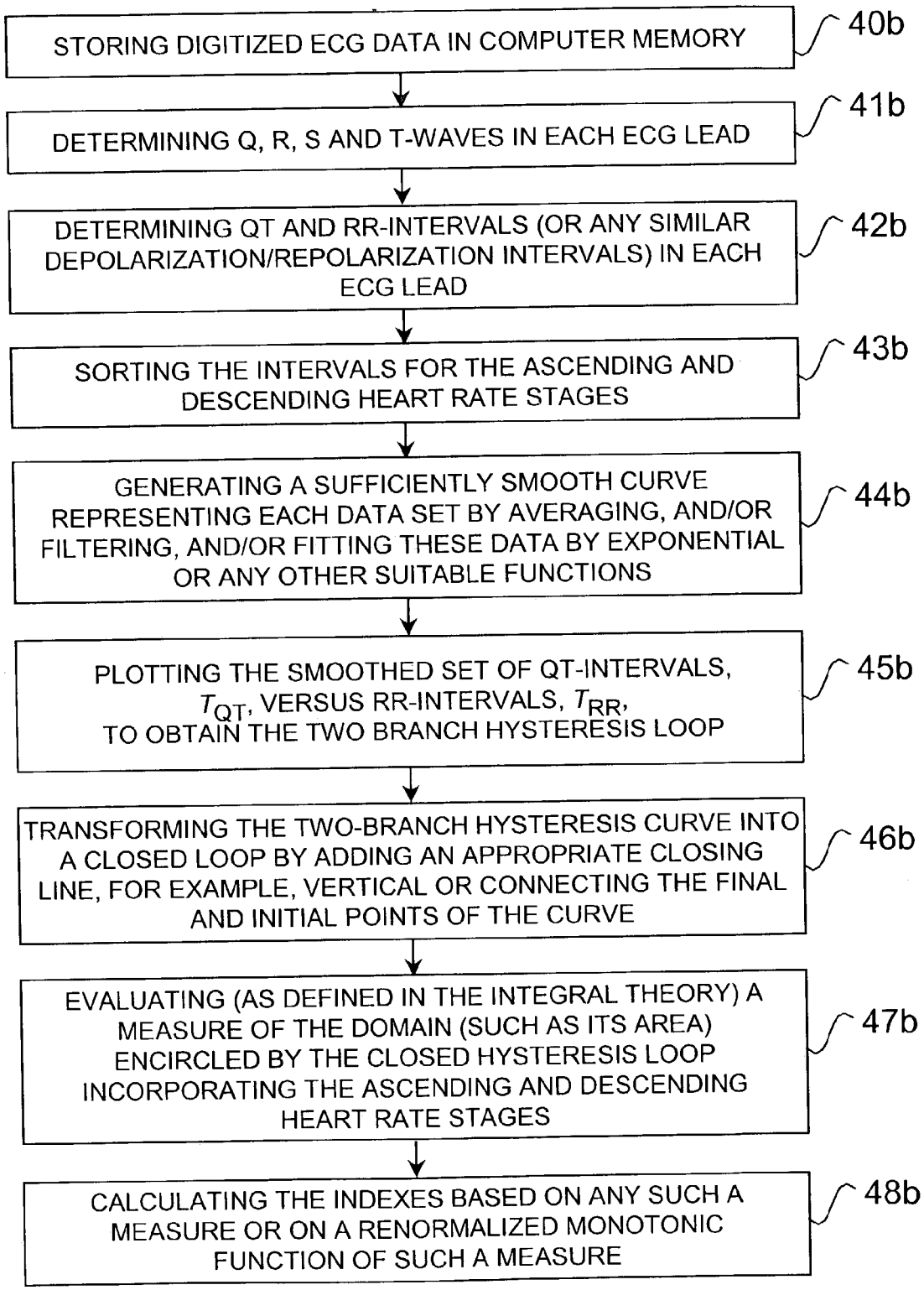
FIG. 4B is an alternative block diagram of the processing steps for data acquisition and analysis of the present invention.

FIG. 4A and FIG. 4B illustrate the major steps of digitized data processing in order to generate an analysis of a QT-RR data set collected from a subject during there-and-back quasi-stationary changes in physiological conditions. The first four steps in FIG. 4A and FIG. 4B are substantially the same. The digitized data collected from a multi-lead recorder are stored in a computer memory for each lead as a data array 40a, 40b. The size of each data array is determined by the durations of the ascending and descending heart rate stages and a sampling rate used by the waveform analyzer, which processes an incoming digitized ECG signal. The waveform analyzer software first detects major characteristic waves (Q,R,S and T waves) of the ECG signal in each particular lead 41a, 41b. Then in each ECG lead it determines the time intervals between consecutive R waves and the beginning of Q and the end of T waves 42a, 42b. Using these reference points it calculates heart rate and RR- and QT-intervals. Then, the application part of the software sorts the intervals for the ascending and descending heart rate stages 43a, 43b. The next two steps can be made in one of the two alternative ways shown in FIGS. 4A and 4B, respectively. The fifth step as shown in FIG. 4A consists of displaying by the application part of software QT-intervals versus RR-intervals 44a, separately for the ascending and descending heart rate stages effected by there-and-back gradual changes in physiological conditions such as exercise, pharmacological/electrical stimulation, etc. The same part of the software performs the next step 45a, which is smoothing, filtering or data fitting, using exponential or any other suitable functions, in order to obtain a sufficiently smooth curve $T_{QT}=F(T_{RR})$ for each stage. An alternative for the last two steps shown in FIG. 4B requires that the application part of the software first averages, and/or filters and/or fits, using exponential or any other suitable functions, the QT intervals as functions of time for both stages and similarly processes the RR-interval data set to produce two sufficiently smooth curves $T_{QT}=F_{QT}(t)$ and $T_{RR}=F_{RR}(t)$, each including the ascending and descending heart rate branches 44b. At the next step 45b the application part of the software uses this parametric representation to eliminate time and generate and plot a sufficiently smooth hysteresis loop $T_{QT}=F(T_{RR})$. The following steps shown in FIG. 4A and FIG. 4B are again substantially the same. The next step 46a, 46b performed by the application part of the software can be graphically presented as closing the two branch hysteresis loop with an appropriate interconnecting or partially connecting line, such as a vertical straight line or a line connecting the initial and final points, in order to produce a closed hysteresis loop on the $(T_{QT},T_{RR})$-plane. At the next step 47a, 47b the application software evaluates for each ECG lead an appropriate measure of the domain inside the closed hysteresis loop. A measure, as defined in mathematical integral theory, is a generalization of the concept of an area and may include appropriate weight functions increasing or decreasing the contribution of different portions of the domain into said measure. The final step 48a, 48b of the data processing for each ECG lead is that the application software calculates indexes by appropriately renormalizing the said measure or any monotonous functions of said measure. The measure itself along with the indexes may reflect both the severity of the exercise-induced ischemia, as well as a predisposition to local ischemia that can be reflected in some particularities of the shape of the measured composite dispersion-restitution curves. The results of all above-mentioned signal processing steps may be used to quantitatively assess cardiac ischemia and, as a simultaneous option, cardiovascular system health of a particular individual under test.

Instead of using the $(T_{QT},T_{RR})$-plane a similar data processing procedure can equivalently be performed on any plane obtained by a non-degenerate transformation of the $(T_{QT},T_{RR})$-plane, such as $(T_{QT},f_{RR})$ where $f_{RR}=1/T_{RR}$ is the heart rate or the like. Such a transformation can be partly or fully incorporated in the appropriate definition of the said measure.

5. Conditions Under which an Abrupt Stop Exercise Protocol can be Considered as a Quasi-stationary Exercise Protocol.

In general, each stage of a gradually increasing or gradually decreasing quasi-stationary exercise protocol is at least 2, 5, 8, or 10 minutes in duration. Each stage's duration is usually an order of magnitude longer than the average duration (~1 minute) of heart rate adjustment during an abrupt stop of the exercise between average peak load rate (from about 120 or 130 to about 150 or 160 beats/min) and average rest (from about 50 or 60 to about 70 or 80 beats/min) heart rate value (from about 50 or 60 to about 70 or 80 beats/min).

One should note that a short, approximately one-minute heart rate adjustment period after a non-quasi-stationary abrupt stop of exercise is typical only for healthy individuals and patients with a relatively low or moderate level of coronary artery disease (CAD) under relatively low exercise load, e.g., corresponding to a power output not exceeding 75 W (watt). However, the same adjustment period can be significantly longer, e.g., up to 5, 8, or 10 minutes or more in duration for either ischemic patients with coronary artery disease or normal individuals without coronary artery disease, under relatively significant exercise loads such as when the heart rate is relatively high. The threshold heart rate at which the adjustment period is increased and becomes quasi-stationary can be defined by the formula $$PT=(220\pm V\text{ bpm})-\text{age};$$

where PT is the predetermined threshold heart rate, V is 15, 20, or 25, bpm is beats per minute, and age is the age of said subject. The threshold heart rate may be referred to as a rate close to the maximum predetermined heart rate. In these cases the heart rate deviations (described in the example 9 below) are small and indicate that the individual remains under significant physical stress even after an abrupt stop of exercise, without further exercise load exposure, or with a low load, e.g., less than 25 W load, during the first one or two minutes after exercise. Under conditions of relatively significant exercise load, the recovery portion of the QT/PR hysteresis loop, as well as the whole loop eventually formed after an abrupt stop of exercise, can be considered as the quasi-stationary loop. Indeed, a slow recovery of the heart rate to its initial, prior-to-exercise, level 2, 5, 8, 10 or more minutes in duration with small heart rate deviations and, therefore, still satisfies the underlying definition of a gradual exercise protocol (see example 9, below).

Thus, when the exercise work load is sufficiently high, an abrupt stop of exercise does not impede the quasi-stationary completion of the descending HR recovery stage within methods according to embodiments of the present invention, since due to the prolongation of the HR recovery the QT/RR hysteresis still can be treated as quasi-stationary, and the hysteresis loop measure can be evaluated in the usual way despite the fact that the descending stage of the exercise protocol was not completed.

Note that typically a patient with a distinguished coronary artery disease level, as determined by physical exhaustion, shortness of breath, chest pain, and/or some other clinical symptom, is unable to exercise longer than 3, 5, 8 or 10 or more minutes at even a low-level power output of about 20 watts. A gradual recovery process followed the abrupt stop of such exercise in such patients satisfies the definition of a quasi-stationary process as given herein (see, e.g., Example 9). Note that patients with moderate levels of coronary artery disease can exercise longer, up to 20 minutes or more, and may be exposed to significantly higher exercise workouts ranging from 50 to 300 watts.

The present invention is explained in greater detail in the non-limiting examples set forth below.

EXAMPLE 1

Testing Apparatus

A testing apparatus consistent with FIG. 3 was assembled. The electrocardiograms are recorded by an RZ152PM12 Digital ECG Holter Recorder (ROZINN ELECTRONICS, INC.; 71-22 Myrtle Av., Glendale, N.Y., USA 11385-7254), via 12 electrical leads with Lead-Lok Holter/Stress Test Electrodes LL510 (LEAD-LOK, INC.; 500 Airport Way, P.O. Box L, Sandpoint, Ind., USA 83864) placed on a subject's body in accordance with the manufacturer's instructions. Digital ECG data are transferred to a personal computer (Dell Dimension XPS T500 MHz/Windows 98) using a 40 MB flash card (RZFC40) with a PC 700 flash card reader, both from Rozinn Electronics, Inc. Holter for Windows (4.0.25) waveform analysis software is installed in the computer, which is used to process data by a standard computer based waveform analyzer software. Composite dispersion-restitution curves and an indicium that provides a quantitative characteristic of the extent of cardiac ischemia are then calculated manually or automatically in the computer through a program implemented in Fortran 90.

Experimental data were collected during an exercise protocol programmed in a Landice L7 Executive Treadmill (Landice Treadmills; 111Canfield Av., Randolph, N.J. 07869). The programmed protocol included 20 step-wise intervals of a constant exercise load from 48 seconds to 1.5 minutes each in duration. Altogether these intervals formed two equal-in-duration gradually increasing and gradually decreasing exercise load stages, with total duration varying from 16 to 30 minutes. For each stage a treadmill belt speed and elevation varied there-and-back, depending on the subject's age and health conditions, from 1.5 miles per hour to 5.5 miles per hour and from one to ten degrees of treadmill elevation, respectively.

EXAMPLES 2–6

Human Hysteresis Curve Studies

These examples illustrate quasi-stationary ischemia-induced QT-RR interval hystereses in a variety of different human subjects. These data demonstrate a high sensitivity and the high resolution of the method.

EXAMPLES 2–3

Hysteresis Curves in Healthy Male Subjects of Different Ages

Figure 5:
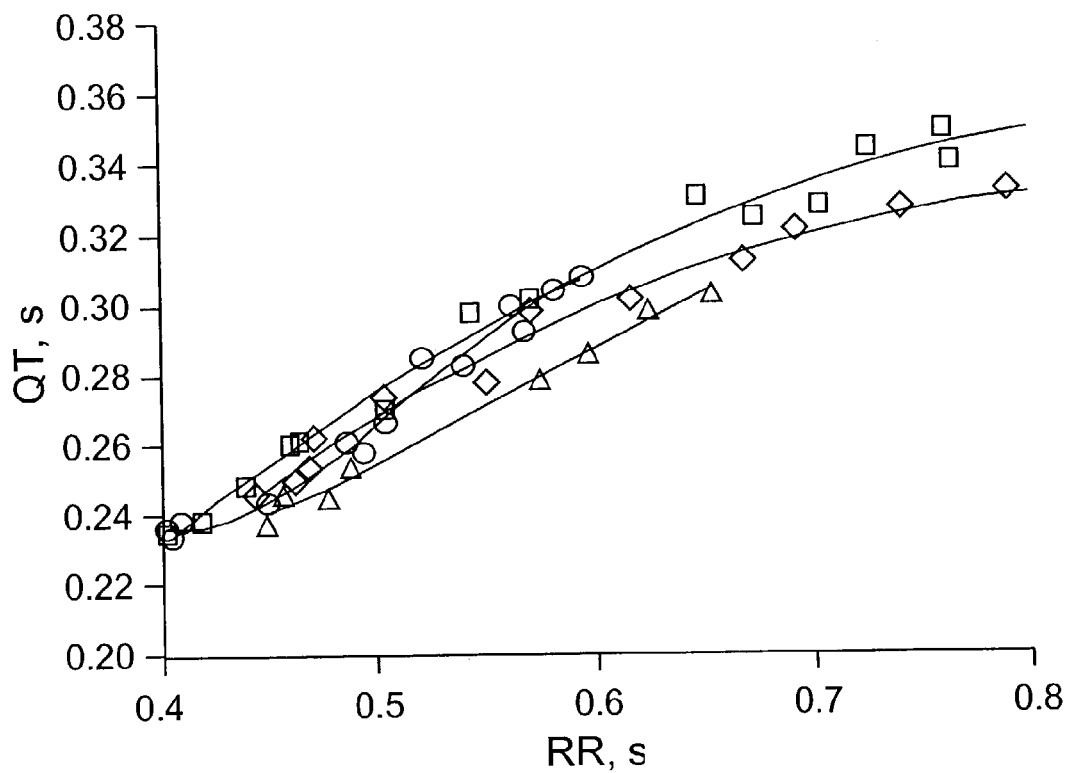
FIG. 5 illustrates experimental QT-interval versus RR-interval hysteresis loops for two healthy male (23 year old, thick line and 47 year old, thin line) subjects plotted on the composite dispersion-restitution curve plane.

These examples were carried out on two male subjects with an apparatus and procedure as described in Example 1 above. Referring to FIG. 5, one can readily see a significant difference in areas of hystereses between two generally healthy male subjects of different ages. These subjects (23 and 47 years old) exercised on a treadmill according to a quasi-stationary 30-minute protocol with gradually increasing and gradually decreasing exercise load. Here squares and circles (thick line) indicate a hysteresis loop for the 23 year old subject, and diamonds and triangles (thin line) correspond to a larger loop for the 47 year old subject. Fitting curves are obtained using the third-order polynomial functions. A beat sampling rate with which a waveform analyzer determines QT and RR intervals is equal to one sample per minute. Neither of the subjects had a conventional ischemia-induced depression of the ECG-ST segments. However, the method of the present invention allows one to observe ischemia-induced hystereses that provide a satisfactory resolution within a conventionally sub-threshold range of ischemic events and allows one to quantitatively differentiate between the hystereses of the two subjects.

EXAMPLES 4–5

Figure 6:
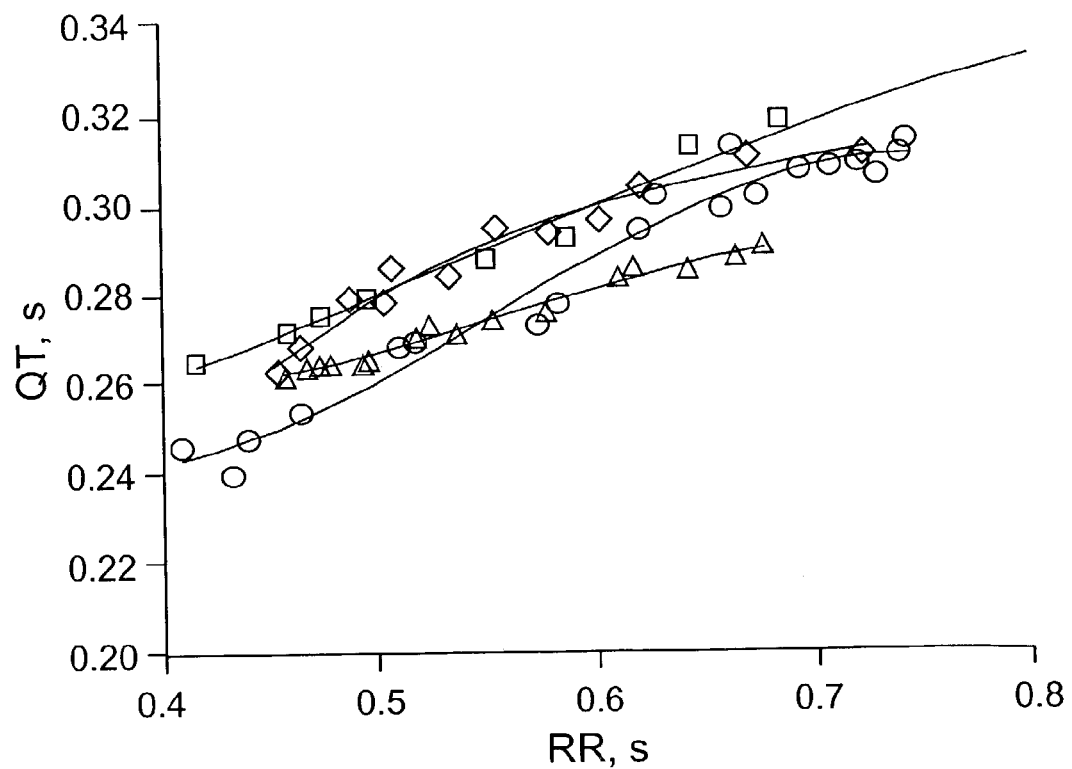
FIG. 6 provides examples of the QT-RR interval hysteresis for two male subjects, one with a conventional ECG ST-segment depression (thin line) and one with a history of a myocardial infarction 12 years prior to the test (thick line). The generation of the curves is explained in greater detail in the specification below.

Hysteresis Curves for Subjects with ST Segment Depression or Prior Cardiac Infarction These examples were carried out on two 55-year-old male subjects with an apparatus and procedure as described in Example 1 above. FIG. 6 illustrates quasi-stationary QT-RR interval hystereses for the male subjects. The curves fitted to the squares and empty circles relate to the first individual and illustrate a case of cardiac ischemia also detectable by the conventional ECG—ST segment depression technique. The curves fitted to the diamonds and triangles relate to the other subject, an individual who previously had experienced a myocardial infarction. These subjects exercised on a treadmill according to a quasi-stationary 20-minute protocol with a gradually increasing and gradually decreasing exercise load. Fitting curves are obtained using third-order polynomial functions. These cases demonstrate that the method of the present invention allows one to resolve and quantitatively characterize the difference between (1) levels of ischemia that can be detected by the conventional ST depression method, and (2) low levels of ischemia (illustrated in FIG. 5) that are subthreshold for the conventional method and therefore undetectable by it. The levels of exercise-induced ischemia reported in FIG. 5 are significantly lower than those shown in FIG. 6. This fact illustrates insufficient resolution of a conventional ST depression method in comparison with the method of the present invention.

EXAMPLE 6

Figure 7:
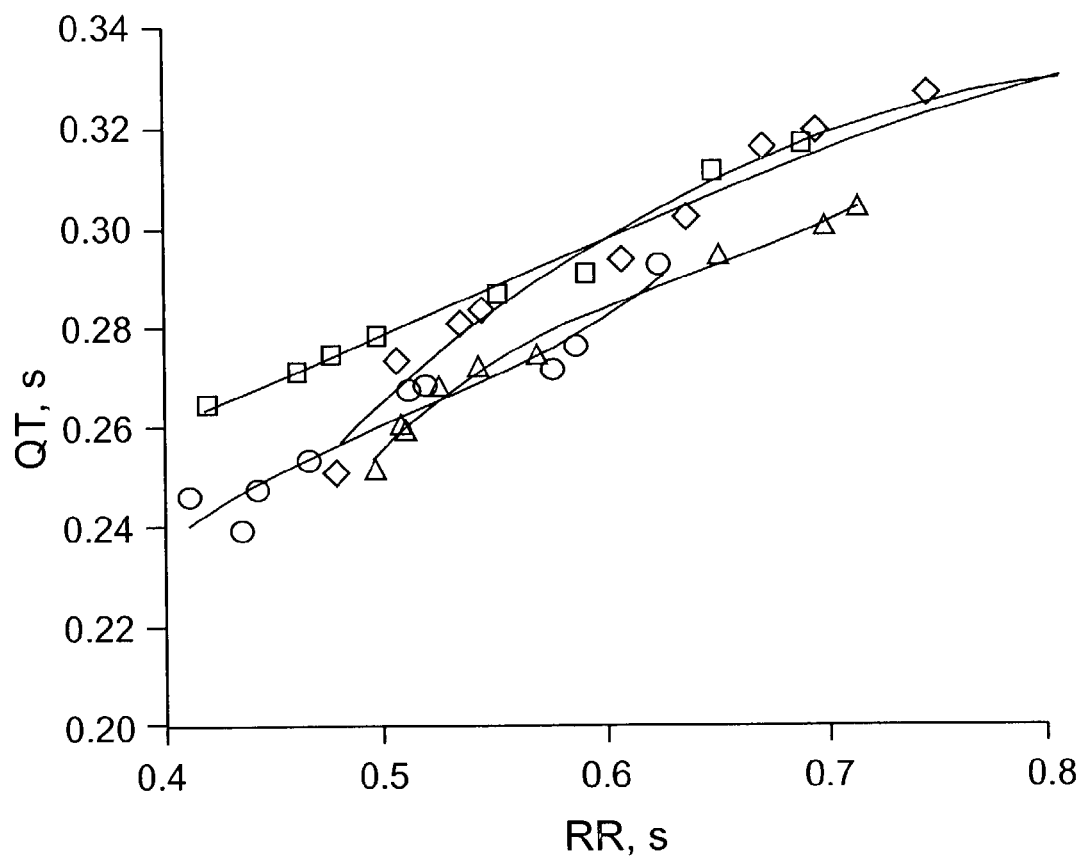
FIG. 7 illustrates sensitivity of the present invention and shows two QT-RR interval hysteresis loops for a male subject, the first one (thick lines) corresponds to the initial test during which an ST-segment depression on a conventional ECG was observed, and the second one shown by thin lines measured after a period of regular exercise.

Hysteresis Curves in the Same Subject Before and After a Regular Exercise Regimen This example was carried out with an apparatus and procedure as described in Example 1 above. FIG. 7 provides examples of quasi-stationary hystereses for a 55 year-old male subject before and after he engaged in a practice of regular aerobic exercise. Both experiments were performed according to the same quasi-stationary 20-minute protocol with a gradually increasing and gradually decreasing exercise load. Fitting curves are obtained using third-order polynomial functions. The first test shows a pronounced exercise-induced cardiac ischemic event developed near the peak level of exercise load, detected by both the method of the present invention and a conventional ECG-ST depression method. The maximum heart rate reached during the first test (before a regular exercise regimen was undertaken) was equal to 146. After a course of regular exercise the subject improved his cardiovascular health, which can be conventionally roughly, qualitatively, estimated by a comparison of peak heart rates. Indeed, the maximum heart rate at the peak exercise load from the first experiment to the second decreased by 16.4%, declining from 146 to 122. A conventional ST segment method also indicates the absence of ST depression, but did not provide any quantification of such an improvement since this ischemic range is sub-threshold for the method. Unlike such a conventional method, the method of the present invention did provide such quantification. Applying the current invention, the curves in FIG. 7 developed from the second experiment show that the area of a quasi-stationary, QT-RR interval hysteresis decreased significantly from the first experiment, and such hysteresis loop indicated that some level of exercise-induced ischemia still remained. A change in the shape of the observed composite dispersion-restitution curves also indicates an improvement since it changed from a flatter curve, similar to the flatter curves (with a lower excitability and a higher threshold, $v_r$=0.3 to 0.35) in FIG. 2, to a healthier (less ischemic) more convex-shape curve, which is similar to the lower threshold curves ($v_r$=0.2 to 0.25) in FIG. 2. Thus, FIG. 7 demonstrates that, due to its high sensitivity and high resolution, the methods can be used in the assessment of delicate alterations in levels of cardiac ischemia, indicating changes of cardiovascular health when treated by a conventional cardiovascular intervention.

EXAMPLE 7

Calculation of a Quantitative Indicium of Cardiovascular Health

Figure 8:
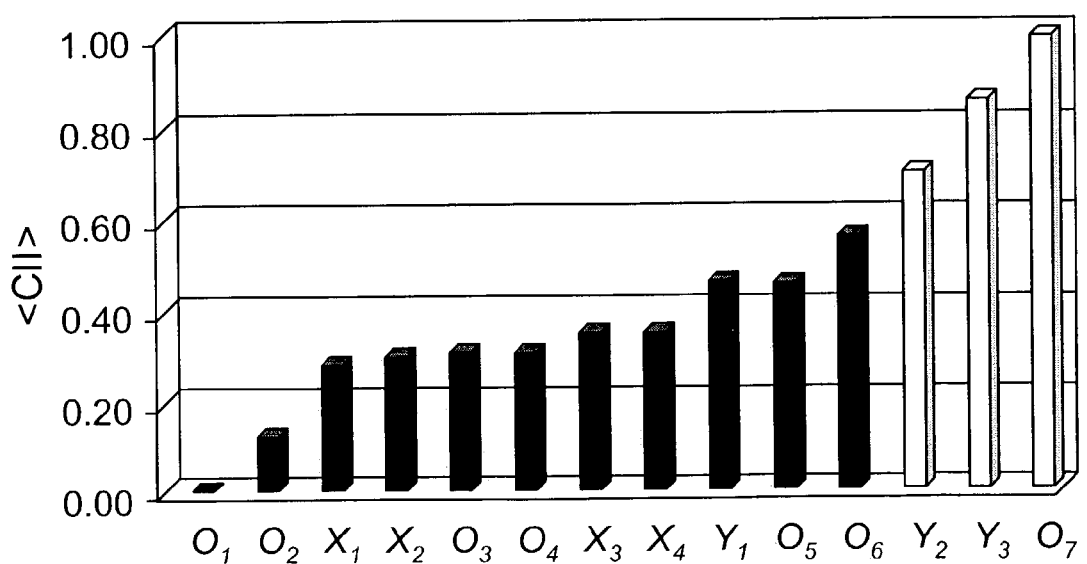
FIG. 8 illustrates a comparative cardiac ischemia analysis based on a particular example of a normalized measure of the hysteresis loop area. $<CII>=(CII-CII_{min})/(CII_{max}-CII_{min})$ ("CII" means "cardiac ischemia index"). $O_I$, $X_I$, and $Y_I$ represent human subject data. $X_i$ represents data collected from one subject (0.28–0.35) in a series of tests (day/night testing, run/walk, about two months between tests); exercise peak heart rate ranged from 120 to 135. $Y_i$ represents data collected from one subject (0.46–0.86) in a series of tests (run/walk, six weeks between tests before and after a period of regular exercise stage); exercise peak heart rate ranged from 122 to 146. Black bars indicate a zone ($<CII>$ less than 0.70) in which a conventional ST depression method does not detect cardiac ischemia. The conventional method may detect cardiac ischemia only in a significantly narrower range indicated by high white bars ($Y_2$, $Y_3$, $O_7$: $<CII>$ greater than 0.70).
Figure 9A:
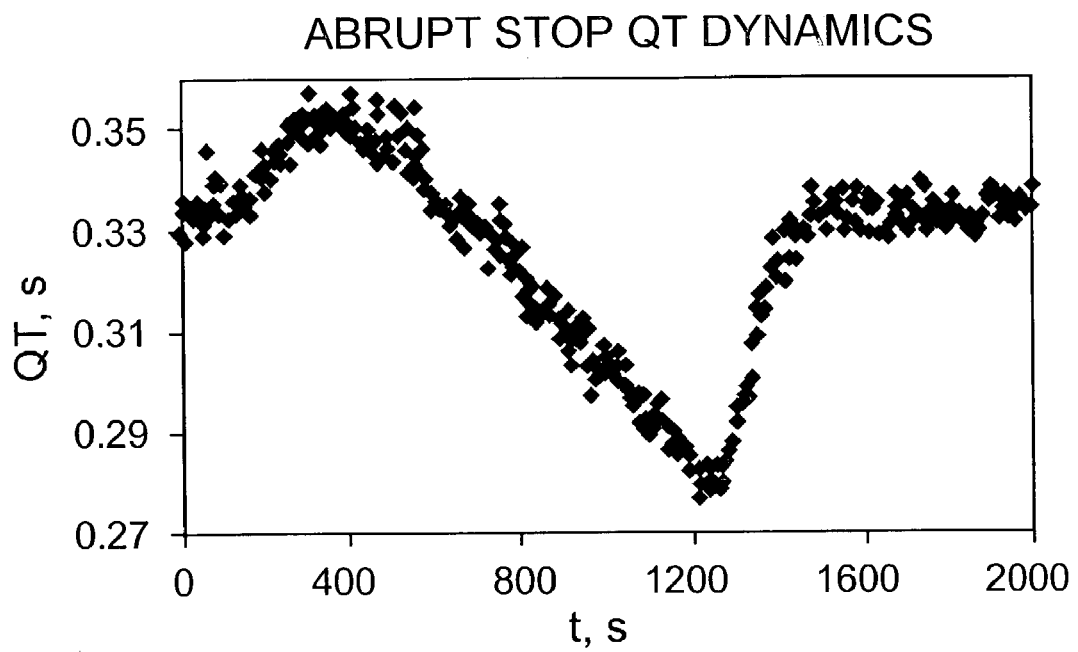
FIG. 9 illustrates a typical rapid peripheral nervous system and hormonal control adjustment of the QT and RR interval to an abrupt stop in exercise (that is, an abrupt initiation of a rest stage).
Figure 9B:
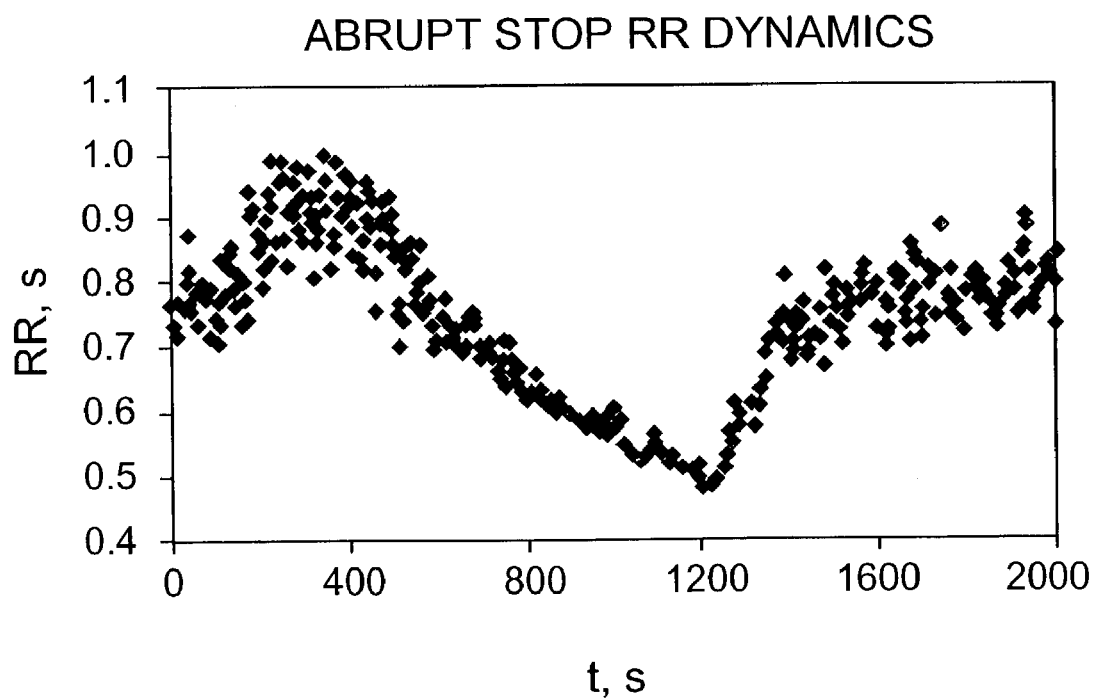
Figure 9C:
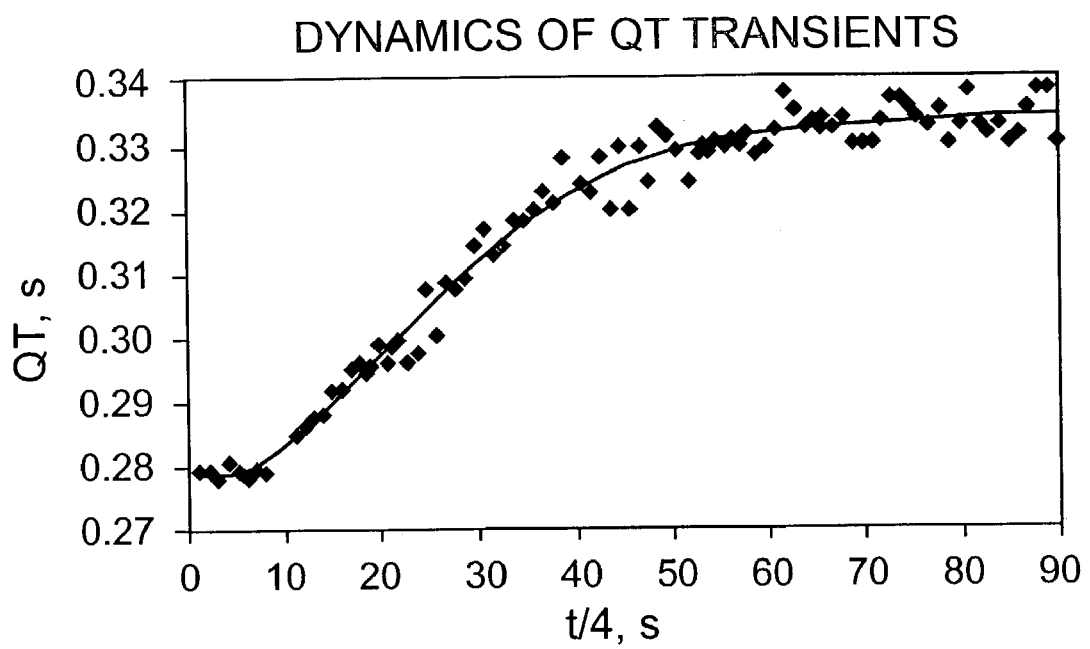
Figure 9D:
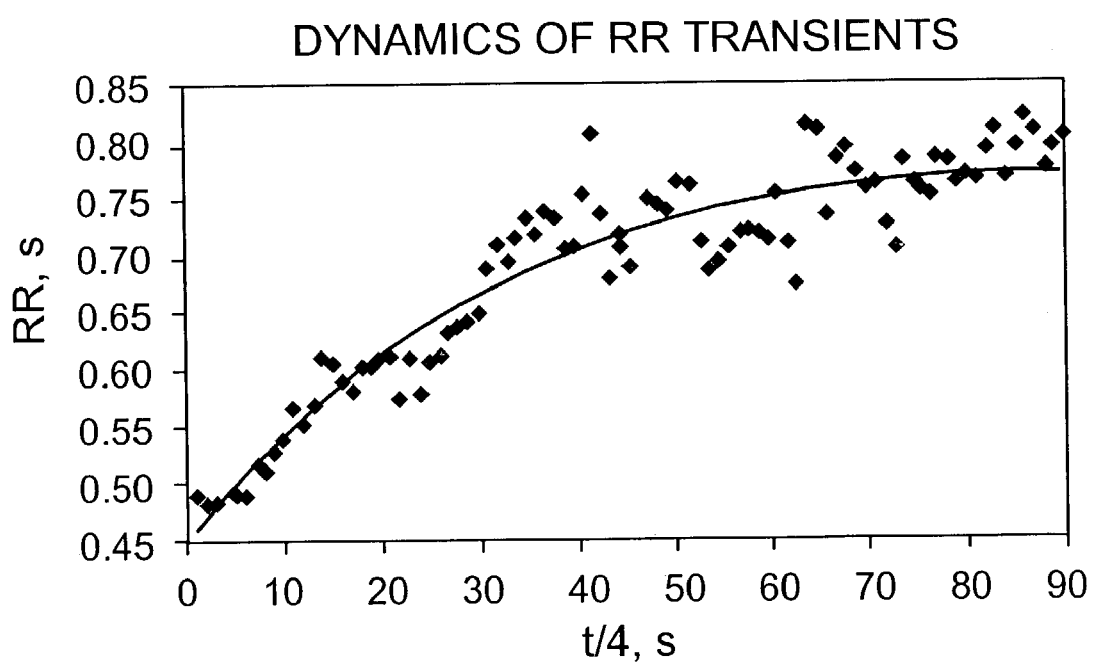

This example was carried out with the data obtained in Examples 2–6 above. FIG. 8 illustrates a comparative cardiovascular health analysis based on ischemia assessment by the method of the present invention. In this example an indicium of cardiovascular health (here designated the cardiac ischemia index and abbreviated "CII") was designed, which was defined as a quasi-stationary QT-RR interval hysteresis loop area, S, normalized by dividing it by the product $(T_{RR,max}-T_{RR,min})(T_{QT,max}-T_{QT,min})$. For each particular subject this factor corrects the area for individual differences in the actual ranges of QT and RR intervals occurring during the tests under the quasi-stationary treadmill exercise protocol. We determined minimum and maximum CII in a sample of fourteen exercise tests and derived a normalized index $<CII>=(CII-CII_{min})/(CII_{max}-CII_{min})$ varying from 0 to 1. Alterations of <CII> in different subjects show that the method of the present invention allows one to resolve and quantitatively characterize different levels of cardiac and cardiovascular health in a region in which the conventional ST depression method is sub-threshold and is unable to detect any exercise-induced ischemia. Thus, unlike a rough conventional ST-segment depression ischemic evaluation, the method of the present invention offers much more accurate assessing and monitoring of small variations of cardiac ischemia and associated changes of cardiac or cardiovascular health.

EXAMPLE 8

Illustration of Rapid Sympatho-Adrenal Transients

FIG. 9 illustrates a typical rapid sympathetic/parasympathetic nervous and hormonal adjustment of the QT (panels A, C) and RR (panels B,D) intervals to a non-quasi-stationary abrupt stop after 10 minutes of exercise with increasing exercise load. All panels depict temporal variations of QT/RR intervals obtained from the right precordial lead V3 of the 12-lead multi-lead electrocardiogram. A sampling rate with which a waveform analyzer determined QT and RR intervals was equal to 15 samples per minute. A human subject (a 47 year-old male) was at rest the first 10 minutes and then began to exercise with gradually (during 10 minutes) increasing exercise load (Panels A, B—to the left from the RR, QT minima). Then at the peak of the exercise load (heart rate about 120 beat/min) the subject stepped off the treadmill in order to initialize the fastest RR and QT interval's adaptation to a complete abrupt stop of the exercise load. He rested long enough (13 minutes) in order to insure that QT and RR intervals reached post-exercise average stationary values. Panels C and D demonstrate that the fastest rate of change of QT and RR intervals occurred immediately after the abrupt stop of the exercise load. These rates are about 0.015 s/min for QT intervals while they vary from 0.28 s to 0.295 s and about 0.15 s/min for RR intervals while they grow from 0.45 s to 0.6 s. Based on the above-described experiment, a definition for "rapid sympatho-adrenal and hormonal transients" or "rapid autonomic nervous system and hormonal transients" may be given.

It is noted that the peak exercise load in Example 8 is not sufficient to cause a quasi-stationary abrupt stop in the subject. That is, the exercise load does not cause sufficient stress to require a lengthened recovery period as observed in Examples 9 and 10. Rapid transients due to autonomic nervous system and hormonal control refer to the transients with the rate of 0.15 s/min for RR intervals, which corresponds to the heart rate's rate of change of about 25 beat/min, and 0.02 s/min for QT intervals or faster rates of change in RR/QT intervals in response to a significant abrupt change (stop or increase) in exercise load (or other cardiac stimulus). The significant abrupt changes in exercise load are defined here as the load variations which cause rapid variations in RR/QT intervals, comparable in size with the entire range from the exercise peak to the stationary average rest values.

EXAMPLE 9

Illustration of a Low Heart Rate Quasi-Stationary Exercise Protocol

Figure 10A:
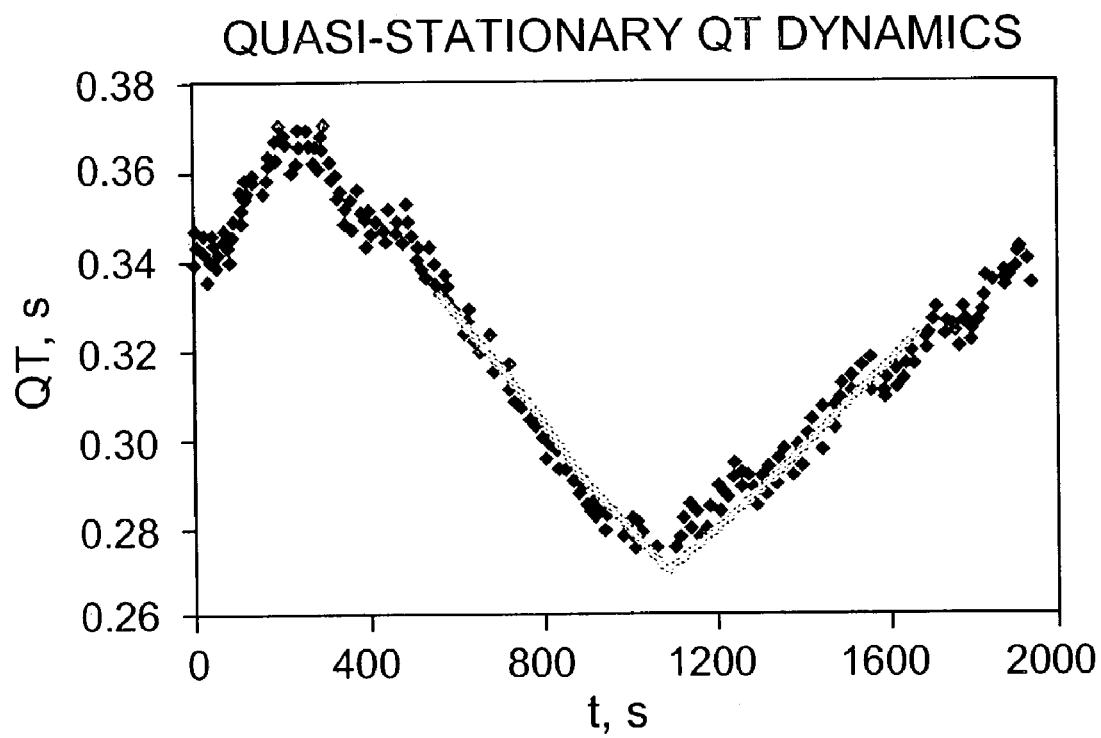
FIG. 10 illustrates a typical slow (quasi-stationary) QT and RR interval adjustment measured during gradually increasing and gradually decreasing cardiac stimulation.
Figure 10B:
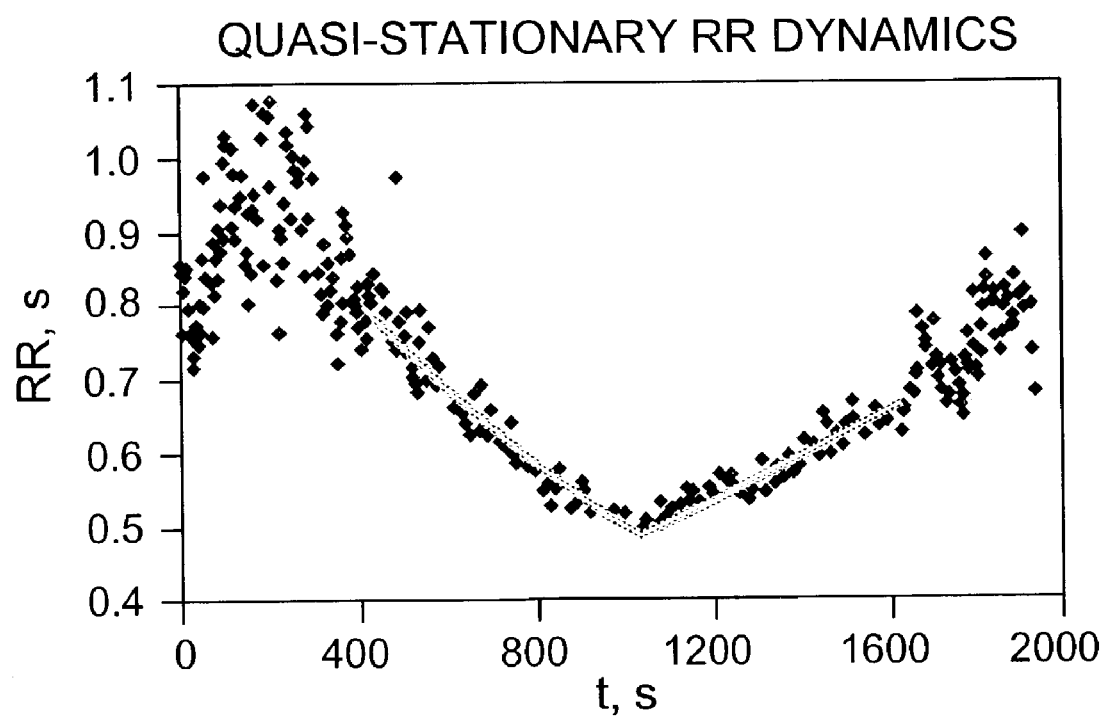
Figure 11:
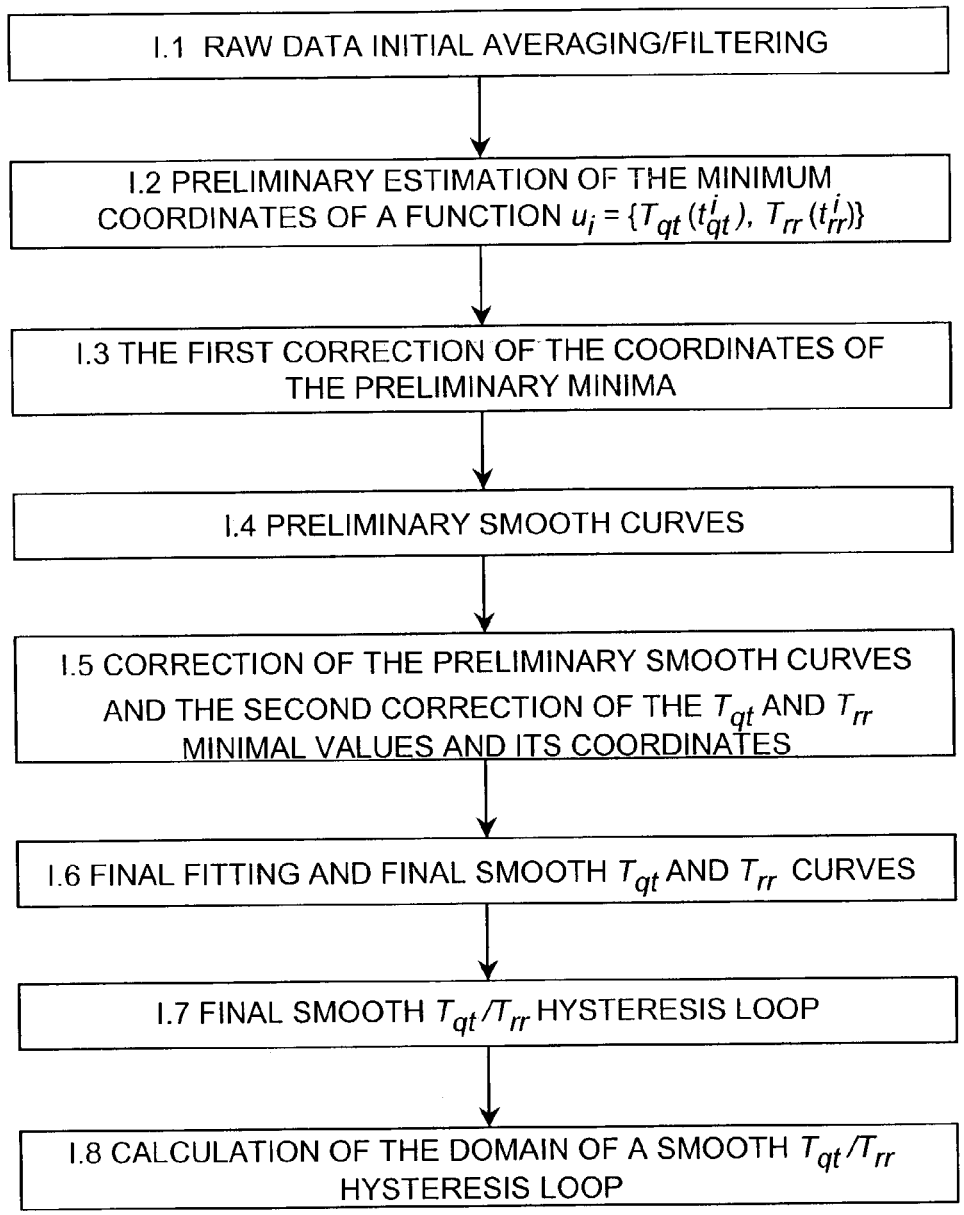
FIG. 11 demonstrates a block-diagram of the data processing by the method of optimized consolidation of a moving average, exponential and polynomial fitting (Example 11, steps 1–8).
Figure 13:
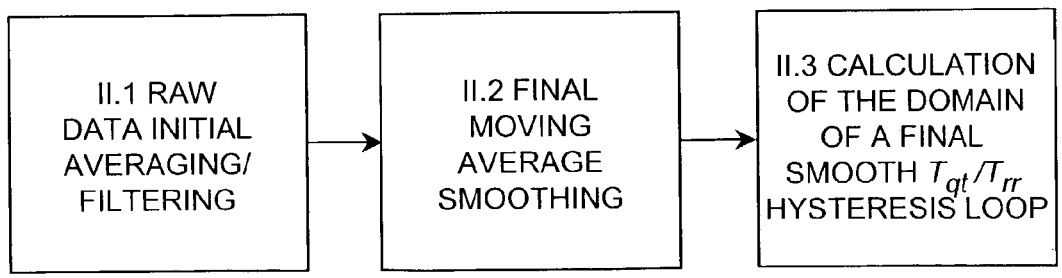
FIG. 13 demonstrates a block-diagram of the data processing by the method of a sequential moving average (Example 12, steps 1–3)

FIG. 10 illustrates a typical slow (quasi-stationary) QT (panel A) and RR (panel B) interval adjustment measured during gradually increasing and gradually decreasing exercise load in a right pre-cordial V3 lead of the 12 lead electrocardiogram recording. The sampling was 15 QT and RR intervals per minute. A male subject exercised during two consecutive 10 minute long stages of gradually increasing and gradually decreasing exercise load. Both QT and RR intervals gradually approached the minimal values at about a peak exercise load (peak heart rate ~120 beat/min) and then gradually returned to levels that were slightly lower than their initial pre-exercise rest values. The evolution of QT and RR intervals was well approximated by exponential fitting curves shown in gray in panels A and B. The ranges for the QT-RR interval, there-and-back, time variations were 0.34 s-0.27s-0.33 s (an average rate of change ~0.005 s/min) and 0.79 s-0.47 s-0.67 s (an average rate of change ~0.032 s/min or ~6 beat/min) for QT and RR intervals, respectively. The standard root-mean-square deviation, σ, of the observed QT and RR intervals, shown by black dots in both panels, from their exponential fits were on an order of magnitude smaller than the average difference between the corresponding peak and rest values during the entire test. These deviations were σ~0.003 s for QT and σ~0.03 s for RR intervals, respectively. According to FIG. 9 (panels C, D) such small perturbations, when associated with abrupt heart rate changes due to physiological fluctuations or due to discontinuity in an exercise load, may develop and decay faster than in 10 s, the time that is 60 times shorter than the duration of one gradual (ascending or descending) stage of the exercise protocol. Such a significant difference between the amplitudes and time constants of the QT/RR interval gradual changes and abrupt heart rate fluctuations allows one to average these fluctuations over time and fit the QT/RR protocol duration dynamics by an appropriate smooth exponential-like function with a high order of accuracy. A simultaneous fitting procedure (panels A, B) determines an algorithm of a parametrical time dependence elimination from both measured QT/RR data sets and allows one to consider QT interval for each exercise stage as a monotonic function.

Protocols that are gradual, low load, low heart rate, and quasi-stationary that may be useful for coronary artery disease patients are described in copending application Ser. No. 10/036,005, filed Dec. 26, 2001.

EXAMPLE 10

Illustration of a High Heart Rate Quasi-Stationary Exercise Protocol

Figure 23:
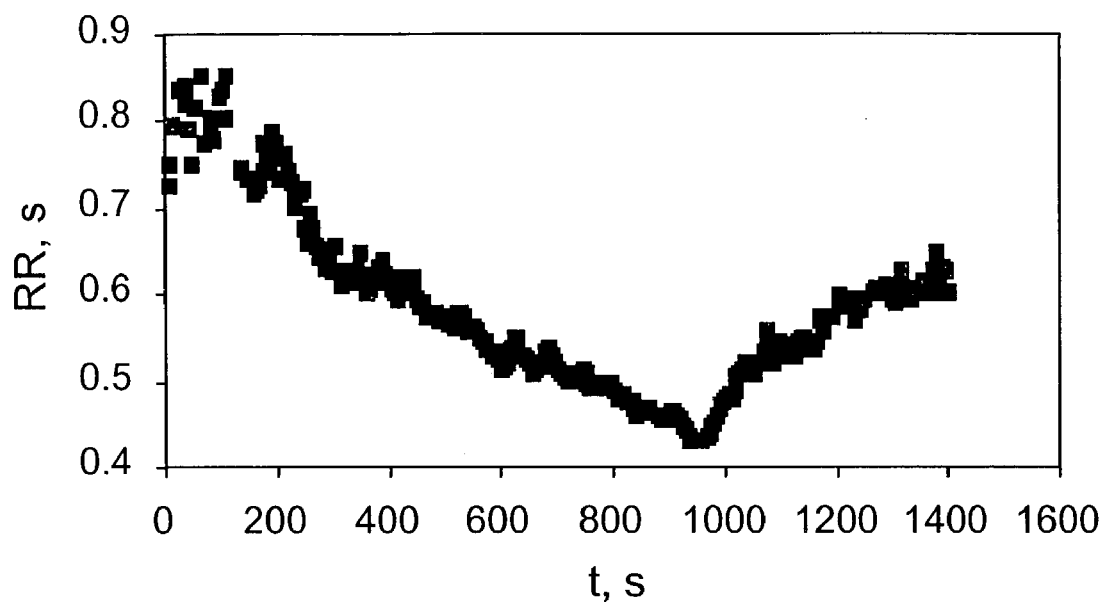
FIG. 23 is an RR-interval data set for a 50-year-old individual after fourteen minutes of work load before an almost abrupt stop of exercise preceded by two minutes of low, 20 W recovery work load after a peak work load of 130 W.
Figure 24:
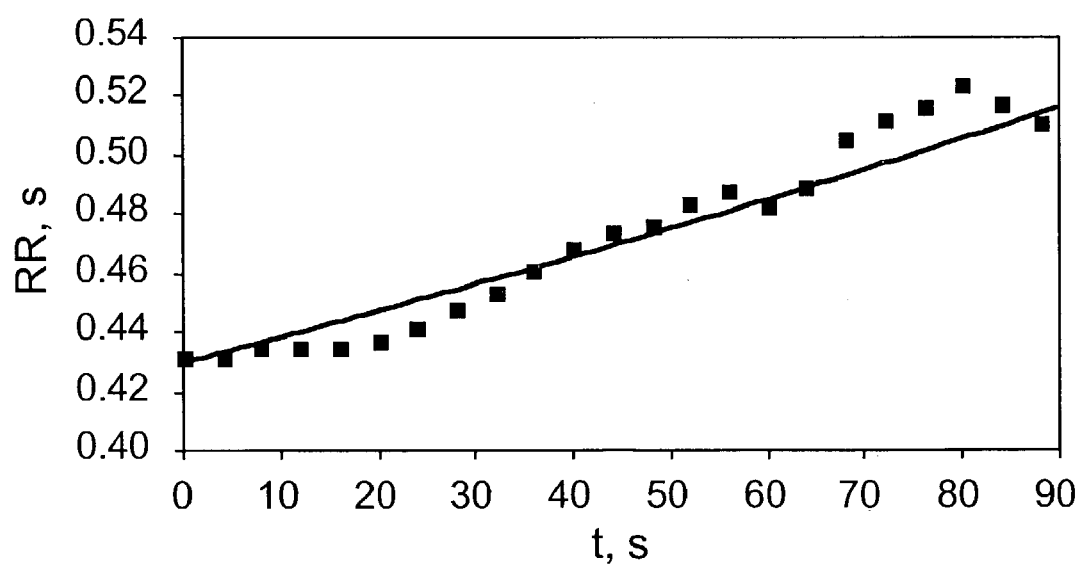
FIG. 24 is an RR-interval data set for the first 1.5 minutes of recovery after the almost abrupt stop of exercise preceded by two minutes of low, 20 W recovery work load after a peak work load of 130 W for the same 50-year-old individual in FIG. 23.
Figure 25:
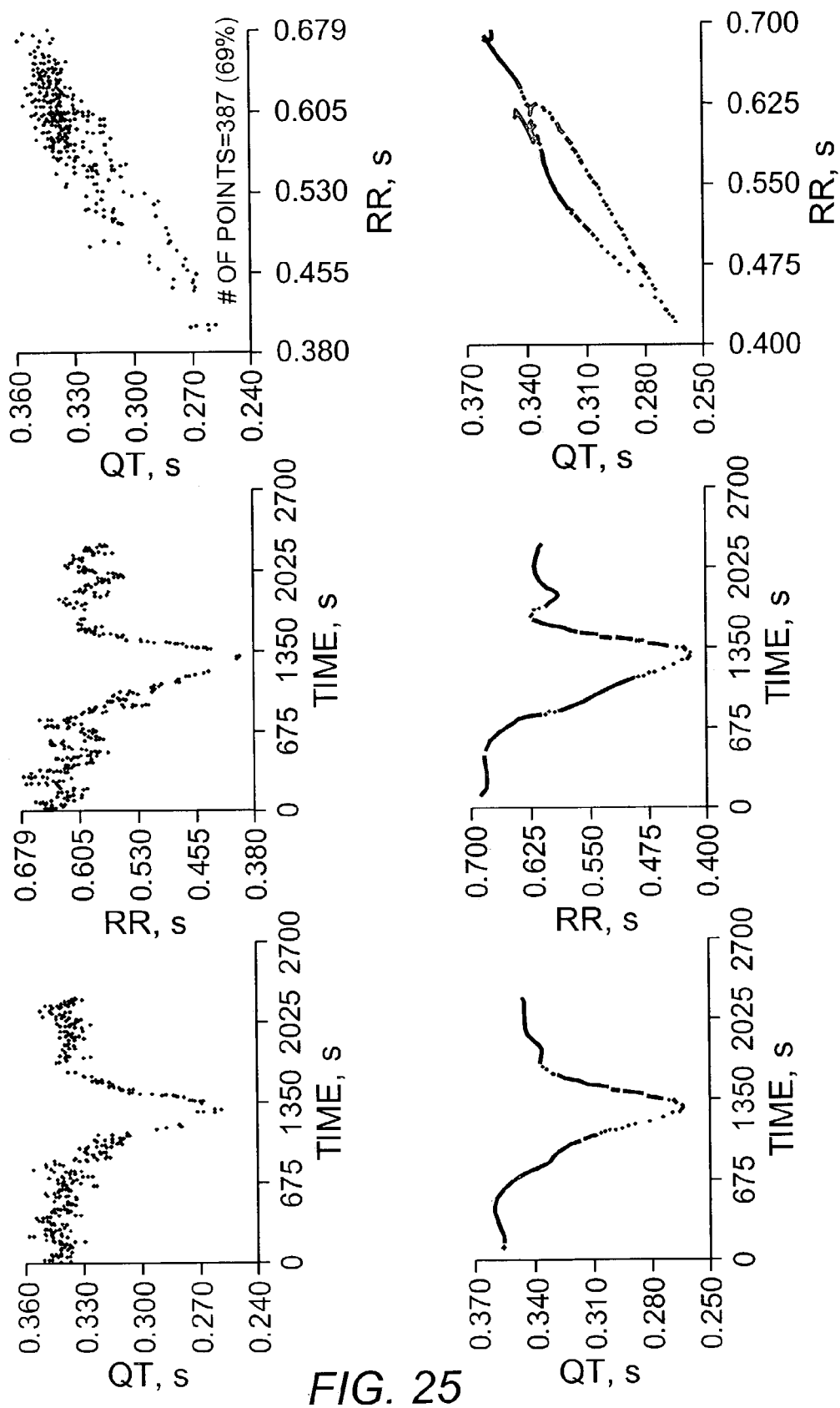
FIGS. 25–26 are RR- and QT-interval data sets and a calculated hysteresis loop for the coronary artery disease patient and the patient without coronary artery disease, respectively.
Figure 26:
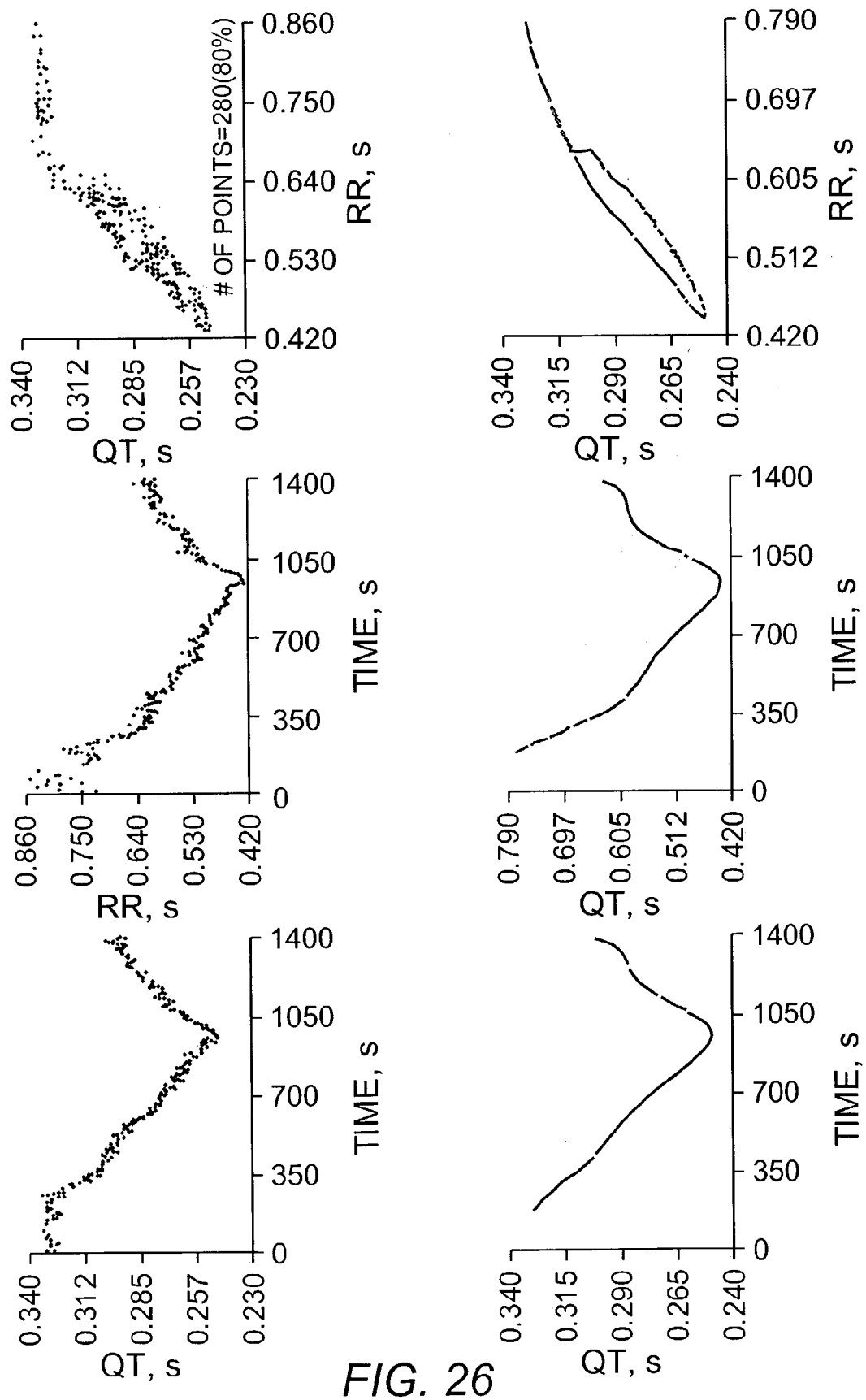

FIGS. 21–24 are the RR-interval data sets for a coronary artery disease patient and a patient without coronary artery disease. FIGS. 25–26 illustrate the formation of a hysteresis loop for the coronary artery disease patient and the patient without coronary artery disease. QT- and RR-interval data was collected from each subject during a stage of gradually increasing heart rate up to a predetermined threshold heart rate and during a stage of gradually decreasing heart rate. The stage of gradually decreasing heart rate may be preceded by a stage of reduced exercise load, as indicated.

Figure 21:
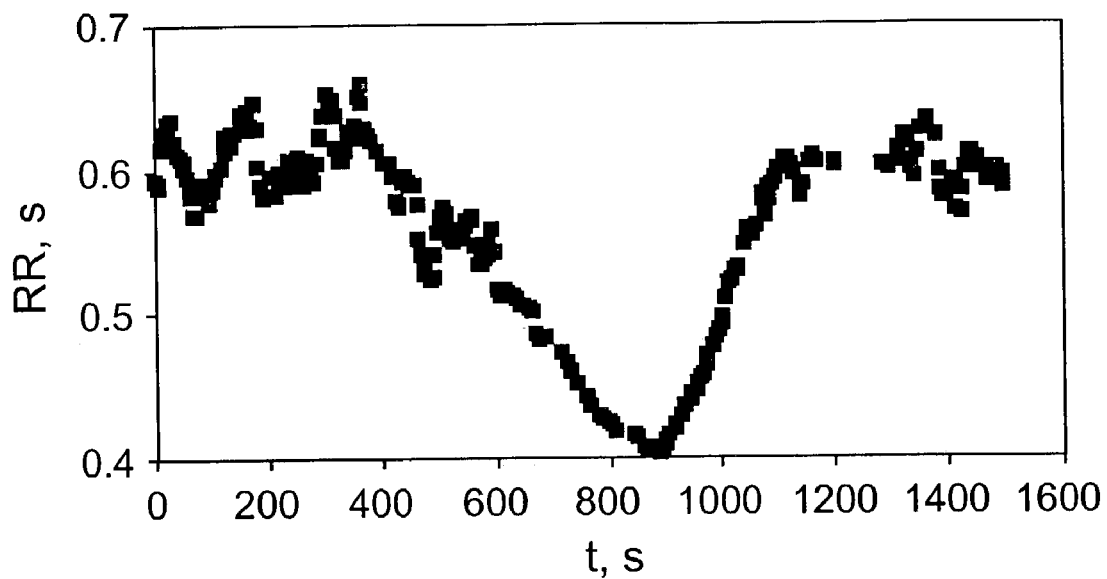
FIG. 21 is an RR-interval data set for a 60-year-old coronary artery disease "CAD" patient with 4.5 minutes of work load before an abrupt stop of exercise with a peak work load of 28 W (watt).
Figure 22:
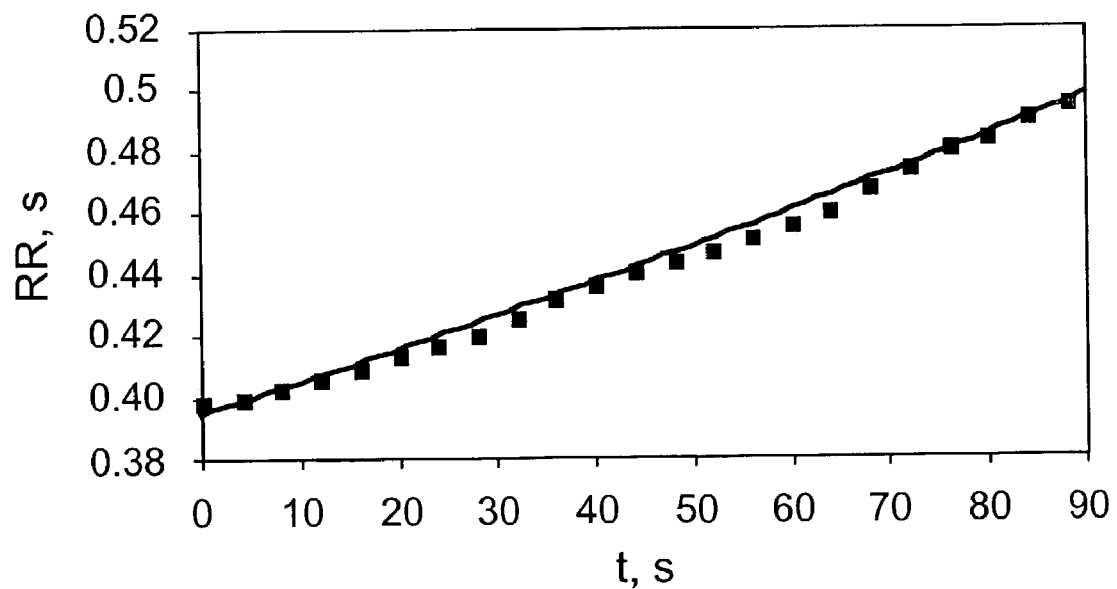
FIG. 22 is an RR-interval data set for the first 1.5 minutes of recovery after the abrupt stop of exercise with 4.5 minutes of work load for the same CAD patient in FIG. 21. The HR recovery occurs at a slow, quasi stationary rate of 9 beats/min.

FIG. 21 is an RR-interval data set for a 60-year-old coronary artery disease patient with 4.5 minutes of work load before a quasi-stationary abrupt stop of exercise with a peak work load of 28 W (watt). FIG. 22 is an RR-interval data set for the first 1.5 minutes of recovery after the quasi-stationary abrupt stop of exercise with 4.5 minutes of work load for the same coronary artery disease patient in FIG. 21. The heart rate recovery occurs at a slow, quasi-stationary rate of 9 beats/min. FIG. 25 shows the formation of the hysteresis loop for the same patient using QT- and RR-data. The upper and lower panels show raw and smoothed data, respectively.

FIG. 23 is an RR-interval data set for a 50-year-old individual without coronary artery disease after fourteen minutes of work load before an almost abrupt stop of exercise preceded by two minutes of low, 20 W recovery work load after a peak work load of 130 W. FIG. 24 is an RR-interval data set for the first 1.5 minutes of recovery after the almost abrupt stop of exercise preceded by two minutes of low, 20 W recovery work load after a peak work load of 130 W for the same 50-year-old individual in FIG. 23. The heart rate recovery is characterized by a quasi-stationary rate of 14 beats/min. FIG. 26 shows the formation of the hysteresis loop for the same patient using QT- and RR-data. The upper and lower panels show raw and smoothed data, respectively.

In both experiments, a sufficiently high heart rate was achieved such that the abrupt stop of exercise (FIGS. 21–22 and 25) and the two minutes of recovery workload followed by an abrupt stop of exercise (FIGS. 23–24 and 26) resulted in quasi-stationary conditions. The maximum workload in FIG. 26 is more than four times greater than in FIG. 25 and the exercise time is about three times longer. Therefore, the total exercise work performed by the non-coronary artery disease patient in FIG. 26 is more than ten times greater than the exercise performed by the coronary artery disease patient in FIG. 25. In spite of the difference in work load, the areas of the QT/RR hysteresis loops in both FIGS. 25 and 26 have approximately the same value. This indicates that the degree of ischemia in the patient in FIG. 25 is much higher than for the patient in FIG. 26 and may be typical for a coronary artery disease patient.

Based on the above-described experiment and the experiment in Example 9, definitions for a "quasi-stationary" exercise (or stimulation) protocol, can be quantitatively specified: A quasi-stationary exercise (or stimulation) protocol refers to two contiguous stages (each stage 3, 5, 8 or 10 minutes or longer in duration) of increasing and decreasing heart rates or stimulation, such as:

1. Each stage's duration is approximately an order of magnitude (e.g., at least about two, three, five, eight or ten times) longer than the average duration (about 1 minute) of a heart rate adjustment during an abrupt stop of the exercise between average peak load rate (about 120 or 130 to about 150 or 160 beat/min) and average rest (about 50 or 60 to about 70 or 80 beat/min) heart rate values.
2. The standard root-mean-square deviations of the original QT/RR interval data set from their smooth and monotonic (for each stage) fits are of an order of magnitude (e.g., at least about two, three, five, ten times) smaller than the average differences between peak and rest QT/RR interval values measured during the entire exercise under the quasi-stationary protocol.

As shown above (FIG. 10) a gradual quasi-stationary protocol itself allows one to substantially eliminate abrupt time dependent fluctuations from measured RR/QT interval data sets because these fluctuations have short durations and small amplitudes. Their effect can be even further reduced by fitting each RR/QT interval data set corresponding to each stage with a monotonic function of time. As a result the fitted QT interval values during each exercise stage can be presented as a substantially monotonic and smooth function of the quasi-stationary varying RR interval value. Presented on the (RR-interval, QT-interval)-plane this function gives rise to a loop, whose shape, area and other measures depend only weakly on the details of the quasi-stationary protocol, and is quite similar to the hysteresis loop presented in FIG. 2. Similar to a generic hysteresis loop, this loop can be considered as primarily representing electrical conduction properties of cardiac muscle.

It is well known that exercise-induced ischemia alters conditions for cardiac electrical conduction. If a particular individual has an exercise-induced ischemic event, then one can expect that the two experimental composite dispersion-restitution curves corresponding to the ascending and descending stages of the quasi-stationary protocol will be different and will form a specific quasi-stationary hysteresis loop. Since according to a quasi-stationary protocol the evolution of the average values of QT and RR intervals occurs quite slowly as compared with the rate of the transients due to sympathetic/parasympathetic and hormonal control, the hysteresis loop practically does not depend on the peculiarities of the transients. In that case such a hysteresis can provide an excellent measure of gradual ischemic exercise dependent changes in cardiac electrical conduction and can reflect cardiac health itself and cardiovascular system health in general.

It should be particularly emphasized that neither J. Sarma et al, supra, nor A. Krahn's et al. supra, report work based on collecting quasi-stationary dependences, which are similar to the QT-interval -RR interval dependence, since in fact both studies were designed for different purposes. To the contrary, they were intentionally based on non-quasi-stationary exercise protocols that contained an abrupt exercise stop at or near the peak of the exercise load. These protocols generated a different type of QT/RR interval hysteresis loop with a substantial presence of non-stationary sympathoadrenal transients (see FIG. 9 above). Thus these prior art examples did not and could not include data which would characterize gradual changes in the dispersion and restitution properties of cardiac electrical conduction, and therefore included no substantial indication that could be attributed to exercise-induced ischemia.

EXAMPLES 10–12

Data Processing at Steps 44–45a,b (FIGS. 4A and 4B)

The following Examples describe various specific embodiments for carrying out the processing, shown in FIG. 4B, where the software implemented at steps 44b and 45b performs the following major steps:

(i) Generates sufficiently smooth time dependent QT and RR data sets by averaging/filtering and fitting these averaged data by exponential or any other suitable functions;

(ii) Combines into pairs the points of RR and QT data sets that correspond to the same time instants, thereby generating smooth QT/RR curves for the ascending and descending heart rate stages (branches) on the ($T_{RR}$, $T_{QT}$)-plane or a similar plane or its image in computer memory;

(iii) Closes the ends of the QT/RR curves to transform them into a closed loop and determines an area, S, or a similar measure of the domain confined by the said loop and computes an index to provide a quantitative characteristic of cardiovascular health in a human subject based on a measure of this domain.

Each of these three major steps may consist of several sub steps, as illustrated in each of the methods shown in FIG. 11, FIG. 13 and FIG. 15, FIG. 16 and as discussed in greater detail below.

EXAMPLE 11

A Method of Optimized Consolidation of a Moving Average, Exponential and Polynomial Fitting 1. Raw data averaging/filtering (box 1 in FIG. 11). The raw data set consists of two subsets $\{t_{RR}^i, T_{RR}^i\}$ i=1, 2, . . . $N_{RR}$–1, and $\{t_{QT}^i, T_{QT}^i\}$, i=1, 2, . . . $N_{QT}$–1, where $t_x^i$ and $T_x^i$ denote the i-th sampling time instant and the respective, RR or QT, interval duration (subscript x stands for RR or QT). In order to simplify the notation we shall omit the subscripts RR and QT when it is applicable to both sub-samples. It is convenient to represent each data point as a two-component vector $u_i = (t^i, T^i)$. The /filtering procedure in this example comprises a moving averaging of neighboring data points. We shall denote a moving overage over a set of adjacent points by angular brackets with a subscript indicating the number of points included in the averaging operator. Thus, the preliminary data filtering at this sub step is described by the equation $$\langle u_i \rangle_2 = \frac{1}{2} \sum_{j=i}^{j=i+1} u_j = \frac{u_i + u_{i+1}}{2}, \tag{10.1}$$

for each i=1, 2, . . . N–1, where N is a number of data points in the corresponding (RR or QT) raw data set. Thus, the RR and QT interval durations and the corresponding sampling time points are identically averaged in order to preserve the one-to-one correspondence between them. This procedure removes the high frequency noise present in the raw data. This preliminary smoothing can also be described in the frequency domain and alternatively achieved via appropriate low-pass filtering. All the following processing pertinent to this example will be done on the averaged data points $\langle u_i \rangle_2$ and the angular brackets will be omitted to simplify the notation.

2. Preliminary estimation of the t-coordinates of the minima (box 2 in FIG. 11). The sub step consists of preliminary estimation of the time instants, $t_{RR}^{i_m}$ and $t_{QT}^{j_m}$ of the minima of the initially averaged RR-interval and QT-interval-data sets, respectively. The algorithm does a sequential sorting of the data sets choosing M data points corresponding to M least values of the RR- or QT-intervals and then averages the result. (In our examples, M=10.) First, the algorithm finds the u-vector $u_{i_1} = (t^{i_1}, T^{i_1})$ corresponding to the shortest interval $T^{i_1}$. Next, this data point is removed from the data set $\{u_i\}$ and the algorithm sorts the remaining data set and again finds a u-vector $u_{i_2} = (t^{i_2}, T^{i_2})$ corresponding to the shortest interval $T^{i_2}$. The minimum point is again removed from the data sets and sorting is repeated over and over again, until the $M^{th}$ u-vector $u_{i_m} = (t^{i_m}, T^{i_m})$ corresponding to the shortest interval $T^{i_m}$ is found. Next, the algorithm averages all M pairs and calculates the average minimum time coordinate $\bar{t}$ defined as $$\bar{t} = \frac{1}{M} \sum_{k=1}^{M} t^{i_k} \tag{10.2}$$

Finally, the algorithm determines the sampling time instant $t^{i_m}$, which is nearest to $\bar{t}$. We thus arrive to $t_{RR}^{i_m}$ and $t_{QT}^{j_m}$ for RR and QT data sets, respectively.

3. The first correction of the coordinates of the preliminary minima (box 3 in FIG. 11). At this sub step the first correction to the minimum coordinates $t_{RR}^{i_m}$ and $t_{QT}^{j_m}$ is found. This part of the algorithm is based on the iterative exponential fitting of the T-component of the initially filtered data set $\{u_i\} = \{t^i, T^i\}$ by functions of the form $$T(t) = A \exp [\beta | t - t^m |], \tag{10.3}$$

where $t^m$ is the time instant of the corresponding minimum determined at the previous sub step (i.e., $t^m = t_{RR}^{i_m}$ for RR-intervals and $t^m = t_{QT}^{j_m}$ for QT-intervals). The fitting is done separately for the descending (t<$t^m$) and ascending (t>$t^m$) branches of u(t) with the same value of constants A and $t^m$ and different values of $\beta$ for both branches. The initial value of A is taken from the preliminary estimation at sub step 2: $A = T^{i_m}$ and $t^m = t^{i_m}$ (i.e., $A = T_{RR}^{i_m}, t^m = t_{RR}^{i_m}$ for RR-intervals and $A=T_{QT}^{j^m}$, $t^m=t_{QT}^{j^m}$ for QT-intervals). The initial value of constant β for each branch and each data sub set is obtained from the requirement that the initial mean root square deviation $\sigma=\sigma_0$ of the entire corresponding branch from its fit by equation (10.3) is minimum. In each subsequent iteration cycle new values of constants A and β are determined for each branch. At the beginning of each iteration cycle a constant A is taken from the previous step and the value of β is numerically adjusted to minimize the deviation value, σ. Such iterations are repeated while the mean square deviation σ is becoming smaller and are stopped when σ reaches a minimum value, $\sigma=\sigma_{min}$. At the end of this sub step the algorithm outputs the corrected values A and β and the respective values of $\sigma_{min}^{RR}$ and $\sigma_{min}^{QT}$.

4. The preliminary smooth curves (box 4 in FIG. 11). The sub step consists of calculating a series of moving averages over p consecutive points for each data subset {u} as follows $$u_i^p \equiv \langle u_i \rangle_p = \frac{1}{p} \sum_{j=i}^{i+p-1} u_j. \tag{10.4}$$

We shall refer to the quantity p as the width of the averaging window. The calculation is performed for different values of p, and then the optimum value of the width of the averaging window p=m is determined by minimizing the mean square deviation of the set $\{u_i^p\}=\{t_i^p, T_i^p\}$ from its fit by Eq. (10.3) with the values of parameters A, $t^m$, and β determined at sub step 3. Having performed this procedure for each component of the data set (RR and QT) we arrive to the preliminary smoothed data set $\{u_i^m\}=\{t_i^m, T_i^m\}$, where $$T_i^m = \frac{1}{m} \sum_{j=i}^{i+m-1} T^i, \quad t_i^m = \frac{1}{m} \sum_{j=i}^{i+m-1} t^i \tag{10.5}$$

The number of points in such a data set is $N_m=N-m+1$, where N is the number of data points after the initial filtering at sub step 1.

5. Correction of the preliminary smooth curves and the second correction of the QT and RR minimal values and its coordinates (box 5 in FIG. 11). At this sub step we redefine the moving averages (using a smaller averaging window) in the vicinity of the minimum of quantity T (RR or QT interval). This is useful to avoid distortions of the sought (fitting) curve T=T(t) near its minimum. The algorithm first specifies all data points $\{t^i, T^i\}$ such that $T^i$ lie between $$\min_i\{T^i\} \text{ and } \min_i\{T^i\} + \sigma_{min}.$$

These data points have the superscript values i from the following set $$I = \left\{ i : T^i \in \left[ \min_i\{T^i\}, \min_i\{T^i\} + \sigma_{min} \right] \right\}. \tag{10.6}$$

Let us denote by $i_0 \in I$ and $i_q \in I$ the subscript values corresponding to the earliest and latest time instants among $\{t_i\}$ (i∈I). We thus set $i_0=\min\{I\}$ and $i_q=\max\{I\}$. Denoting the number of points in such a set by $q_{RR}$ for the RR data and by $q_{QT}$, for the QT data we determine the width, q, of the averaging window as the minimum of the two, $q=\min\{q_{QT}, q_{RR}\}$. Now we write the moving average for the data points in the vicinity of the minimum as $$u_i^q \equiv \langle u_i \rangle_q = \frac{1}{q} \sum_{j=i}^{i+q-1} u_j \tag{10.7}$$

Such modified averaging is applied to all consecutive data points $u_i$ with the subscript i ranging from $i_0$ to $i_q$. The final (smoothed) data set consists of the first $i_0-1$ data points defined by Eq.(10.4) with i=1, 2, ... $i_0-1$, q points defined by Eq.(10.7) with $i=i_0, i_0+1, \ldots, i_q$, and $N-i_q-m$ points defined again by Eq.(10.4) with $i=i_q+1, i_q+2, \ldots, N-m+1$. This the final set $\{\bar{u}_i\}$ can be presented as $$\{\bar{u}_i\}=\{u_i^p : i \in \{1, 2, \ldots, i_0-1\} U \{i_q+1, \ldots, N-m+1\}\} U \{u_i^q : i \in \{i_0, i_0+1, \ldots, i_q\}\} \tag{10.8}$$

At the end of sub step 10.5 the algorithm determines the final minimum values of QT and RR interval and the corresponding time instants. The algorithm sorts the smoothed data sets (10.8) and determines $\bar{u}_{min} \equiv (\bar{t}_{min}, \bar{T}_{min})$ corresponding to the minimum value of $\bar{T}_i$. This can be written as $$\bar{u}_{min} \equiv \left\{ (\bar{t}_{i_m}, \bar{T}_{i_m}) : \bar{T}_{i_m} = \min_k \{\bar{T}_k\} \right\} = \bar{u}_{i_m}. \tag{10.9}$$

6. Final fitting and the final smooth QT and RR curves (box 6 in FIG. 11). At this sub step the parameters of functions representing final smooth QT and RR curves are found. First, each data set $\{\bar{u}_i\}$ is split into two subsets $\{u_-^i\}$ and $\{u_+^i\}$ corresponding to the descending $(\bar{t}_i \leq \bar{t}_{i_m})$ and ascending $(\bar{t}_i \geq \bar{t}_{i_m})$ branch, respectively. We also shift the time origin to the minimum point $(\bar{t}_{i_m})$ and change the axis direction of the descending branch. These redefined variables are thus given by:

$$\{u_-^i\}=\{(t_-^i, T_-^i) \equiv (\bar{t}_{i_m}-\bar{t}_i, \bar{T}_i) : i \leq i_m\}\}, \tag{10.10a}$$

$$\{u_+^i\}=\{(t_+^i, T_+^i) \equiv (\bar{t}_i-\bar{t}_{i_m}, \bar{T}_i) : i \geq i_m\}. \tag{10.10b}$$

Notice that the minimum point is included in both branches. Next we perform a linear regression by fitting each branch with a 4-th order polynomial function in the following form $$T_\pm(t_\pm)=a_\pm t_\pm^4+b_\pm t_\pm^3+c_\pm y_\pm^2+d \tag{10.11}$$

The linear term is not included into this expression since this function must have a minimum at $t_\pm=0$. The value of d is defined by $$d=\bar{T}_{min} \tag{10.12}$$

For computational convenience the variables $u_\pm$ are transformed into $z_\pm=T_\pm-d$ and then the coefficients $a_\pm$, $b_\pm$, and $c_\pm$ are determined from the condition that expression for the error $$\varepsilon = \sum_i \left[ z_\pm^i - a_\pm (t_\pm^i)^4 - b_\pm (t_\pm^i)^3 - c_\pm (y_\pm^i)^2 \right]^2 \tag{10.13}$$

where summation is performed over all points of the corresponding branch, is minimized. We thus obtain four similar sets of linear algebraic equations—two for each of the $u_\pm$ branches of the two RR and QT data sets. These equations have the form $$\left\| \begin{matrix} \sum (t_\pm^i)^8 & \sum (t_\pm^i)^7 & \sum (t_\pm^i)^6 \\ \sum (t_\pm^i)^7 & \sum (t_\pm^i)^6 & \sum (t_\pm^i)^5 \\ \sum (t_\pm^i)^6 & \sum (t_\pm^i)^5 & \sum (t_\pm^i)^4 \end{matrix} \right\| \left\| \begin{matrix} a_\pm \\ b_\pm \\ c_\pm \end{matrix} \right\| = \left\| \begin{matrix} \sum (t_\pm^i)^4 z_\pm^i \\ \sum (t_\pm^i)^3 z_\pm^i \\ \sum (t_\pm^i)^2 z_\pm^i \end{matrix} \right\| \quad (10.14)$$

All summations are performed over all points of the branch. Now the QT and RR interval time dependences curves can be presented as the follows $$T_{RR}(t) = \begin{cases} T_{RR}^-(t - t_{min}^{RR}), & t \le t_{min}^{RR} \\ T_{RR}^+(t - t_{min}^{RR}), & t \ge t_{min}^{RR} \end{cases} \quad (10.15)$$

and $$T_{QT}(t) = \begin{cases} T_{QT}^-(t - t_{min}^{QT}), & t \le t_{min}^{QT} \\ T_{QT}^+(t - t_{min}^{QT}), & t \ge t_{min}^{QT} \end{cases} \quad (10.16)$$

where $T_{RR}^\pm(t)$ and $T_{QT}^\pm(t)$ are the fourth order polynomials given by Eq.(10.11) and $t_{min}^{RR}$ and $t_{min}^{QT}$ are the time coordinates of the corresponding minima defined by Eq. (10.9). Thus, formulas (10.10)–(10.16) determine the final smooth QT and RR curves with minima defined by formula (10.9).

7. Final smooth hysteresis loop (box 7 in FIG. 11). At this sub-step the software first generates a dense (N+1)-point time-grid $\tau_k = t_{start} + k(t_{end} - t_{start})/N$, where k=0, 1, 2, . . . , N (N=1000 in this example) and $t_{start}$ and $t_{end}$ are the actual values of time at the beginning and end of the measurements, respectively. Then it computes the values of the four functions $T_{RR}^\pm(\tau - t_{min}^{RR})$ and $T_{QT}^\pm(\tau - t_{min}^{QT})$ on the grid, which parametrically represents the final smooth curves $(T_{RR}^\pm(\tau - t_{min}^{RR}), T_{QT}^\pm(\tau - t_{min}^{QT}))$ in computer memory for the ascending (+) and descending (−) branches, respectively. This procedure is a computational equivalent of the analytical elimination of time. Next, the software also plots these smooth curves on the $(T_{RR}, T_{QT})$-plane or on another, similar plane, such as $(f_{RR}, T_{QT})$, where $f = 1/T_{RR}$ is the instantaneous heart rate. Finally, the algorithm adds to the curves a set of points representing a closing line, which connects the end point of the lower (descending) branch with the initial point on the of the upper (ascending) branch and, thus, generates a closed QT/RR hysteresis loop.

8. A measure of the domain bounded by the QT/RR hysteresis loop (box 8 in FIG. 11). At this sub step a measure of the domain inside the QT/RR hysteresis loop is computed by numerically evaluating the following integral (see definition above):

$$S = \iint_\Omega \rho(T_{RR}, T_{QT}) dT_{RR} dT_{QT} \quad (10.17)$$

where $\Omega$, is the domain on the $(T_{RR}, T_{QT})$-plane with the boundary formed by the closed hysteresis loop, and $\rho(T_{RR}, T_{QT})$ is a nonnegative (weight) function. In this example we can take $\rho(T_{RR}, T_{QT}) = 1$ so that S coincides with the area of domain $\Omega$, or we set $\rho = 1/(T_{RR})^2$ so S coincides with the dimensionless area of the domain inside the hysteresis loop on the $(f, T_{QT})$-plane, where $f = 1/T_{RR}$ is the heart rate.

EXAMPLE 12

A Method of a Sequential Moving Average

1. Raw data averaging/filtering. The sub step (similar to 10.1) consists of raw data averaging (filtering) according to formula (10.4). This is performed for a preliminary set of values of the averaging window width, p.

2. Final moving average smoothing. The sub step includes subsequent final smoothing of the preliminary smoothed data represented by the set $\{u_i^p\}$ found at the previous step: as follows.

$$\overline{u^p} \equiv \langle u_i^p \rangle_{m_f} = \frac{1}{m_f} \sum_{j=i}^{j=i+m_f-1} u_j^p. \quad (11.1)$$

Figure 12:
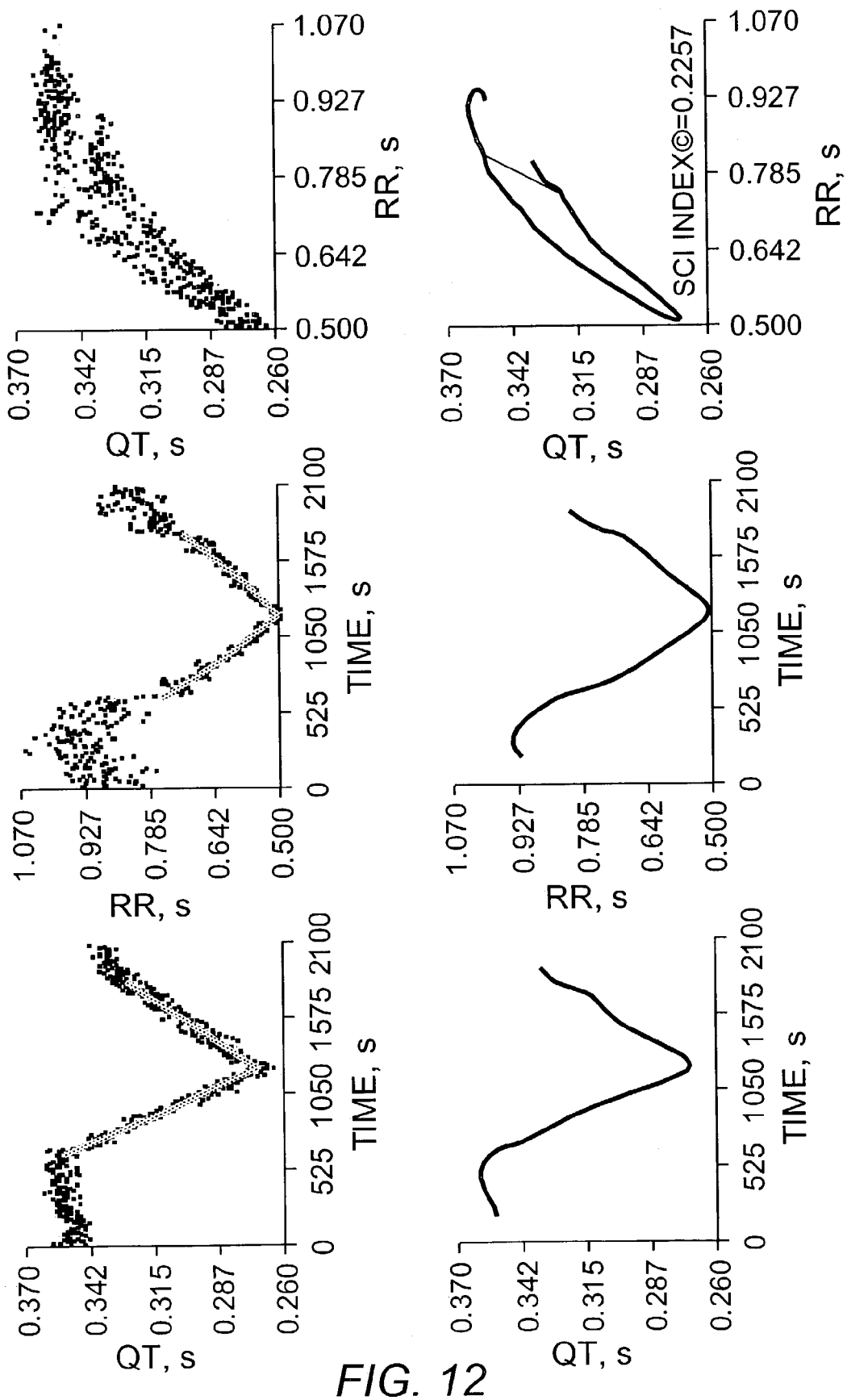
FIG. 12 demonstrates results of the processing throughout steps 1 to 8 of Example 11. Upper panels show QT and RR data sets processed from steps 1 to 3 (from left to right respectively), and the QT/RR hysteresis loop after step 1. The exponential fitting curves (step 3) are shown in gray in the first two panels. Low panels show the same smooth dependencies after processing from step 4 to a final step 8. Here the CII (see right low panel) is equal to a ratio $S/\{((T_{RR}^-(t_{end}-t_{min}^{RR})-T_{RR}^-(0))((T_{QT}^+(t_{start}-t_{min}^{QT})-T_{QT}^+(0))\}$ (see example 10, section 7).
Figure 14:
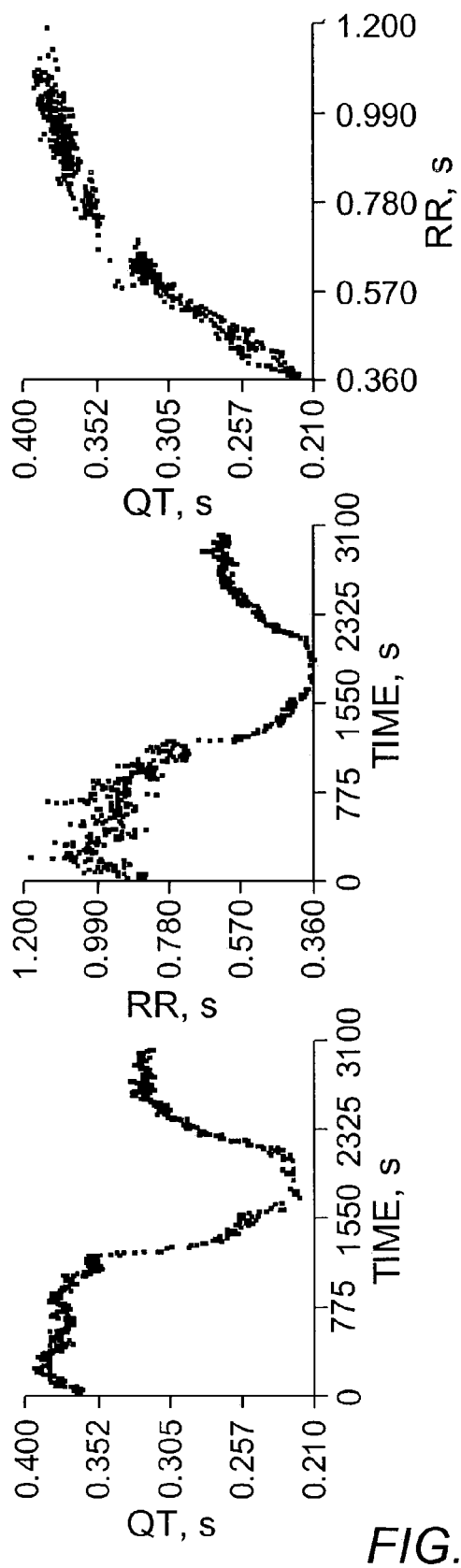
FIG. 14 demonstrates results of the processing throughout steps 1 to 2 of Example 12. Upper panels show processed QT and RR data sets, and the QT/RR hysteresis loop after step 1 (from left to right respectively). Low panels show the same smooth dependencies after the second moving average processing and a final step 3.
Figure 14:
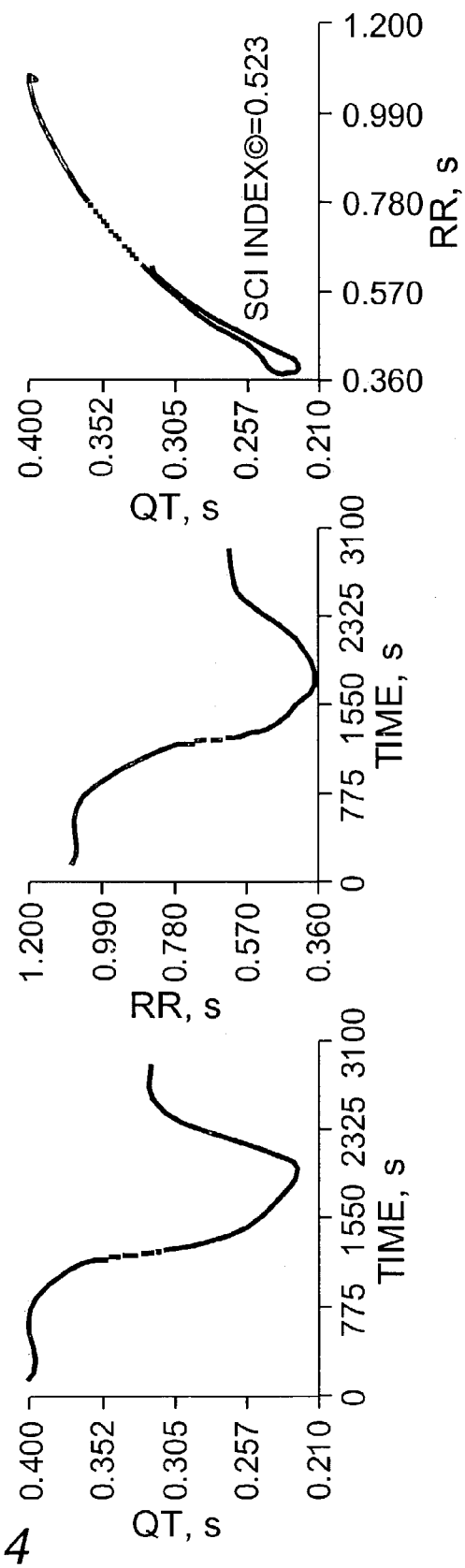

The window width $m_f$ is varied numerically to achieve optimum smoothness and accuracy of the fit. The optimally averaged data points form smooth curves on the corresponding planes (FIGS. 12, 14).

3. A measure of the domain inside the QT/RR hysteresis loop. The procedure on this sub step is as defined in Example 11, step 8, above.

EXAMPLE 13

A Method of Optimized Nonlinear Transformations

Figure 15:
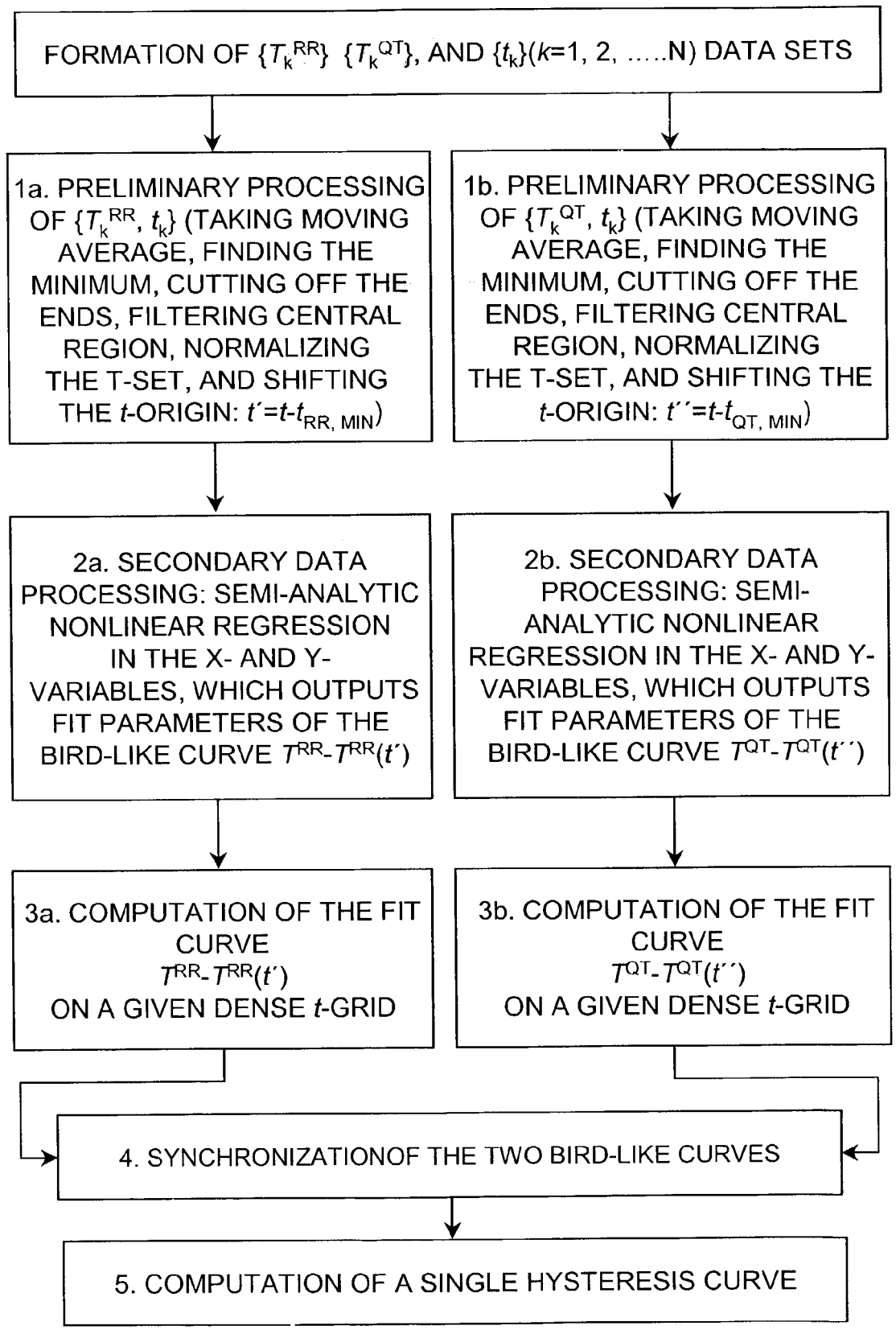
FIG. 15 shows a general data flow chart for major steps in optimized nonlinear transformation method. The left-hand side and the right-hand side boxes describe similar processing stages for the RR and QT-intervals, respectively.

FIG. 15 illustrates major steps in the data processing procedure involving our nonlinear transformations method. The first three stages for the RR and QT data sets are quite similar and each results in the computation of the fitted bird-like curves, $T^{RR} = T^{RR}(t)$ and $T^{QT} = T^{QT}(t)$, on a dense time-grid. Having computed both bird-like curves one actually completes the data processing procedure, because after appropriate synchronization, these two dependences parametrically along with a closing line represent the sought hysteresis loop on the $(T^{RR}, T^{QT})$, or similar, plane. We will describe our method in general terms equally applicable for the QT and RR interval data sets, and indicate the specific instants where there is a difference in the algorithm.

Figure 16:
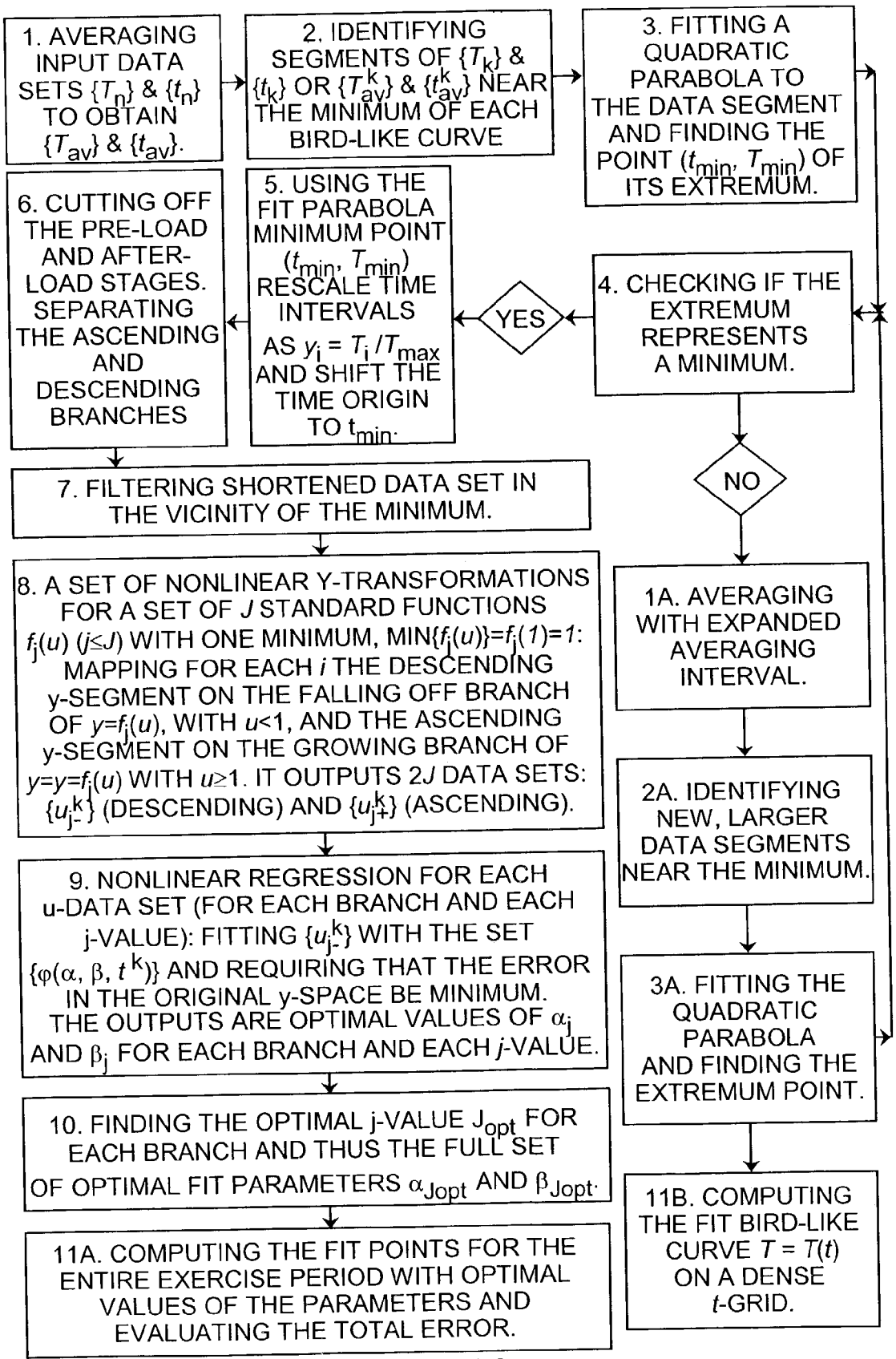
FIG. 16 shows a detailed data flow chart for one data subset, $\{t^k, T^k_{RR}\}$ or $\{t^k, T^k_{QT}\}$ during stages (1a/b) through (3a/b) in FIG. 15. The preliminary stage, boxes 1 through 7, uses a combination of traditional data processing methods and includes: moving averaging (1), determination of a minimum region (2), fitting a quadratic parabola to the data in this region (3), checking consistency of the result (4), finding the minimum and centering data at the minimum (5) and (6), conditionally sorting the data (7). Stages (8) through (11) are based on the dual-nonlinear transformation method for the non-linear regression.

1. Preliminary data processing stage. Let $\{T_k\}$, k=1, 2, . . . , N, be a set of the measured RR or QT interval durations, and $\{t_k\}$ be a set of the corresponding time instants, so that $t_1$ and $t_N$ are the starting and ending time instants (segments) of the entire record. The first three similar stages (stages 1 through 3 in FIG. 15) are the preliminary stage, the secondary, nonlinear-transformation stage, and the computational stage. A more detailed data flow chart for these stages is shown in FIG. 16. The preliminary stage, indicated by boxes 1 through 7 in FIG. 16, is a combination of traditional data processing methods and includes: smoothing (averaging) the data sets (1), determination of a region near the minimum (2), and fitting a quadratic parabola to the data in this region (3), checking consistency of the result (4), renormalizing and centering the data at the minimum (5), cutting off the data segments outside the exercise region and separating the ascending and descending branches (6), and finally filtering off a data segment in near the minimum (7). Let us discuss these steps in more detail.

Box 1 in FIG. 16, indicates the moving averaging and itself consists of two steps. First, we specify the initial value of the moving average procedure parameter m, as $$m = \max\left\{r\left(\frac{N}{N_c}\right), m_{\min}\right\} \quad (12.1)$$

where r(x) is the integer closest to x, and the values of $N_c$ and $m_{min}$ are chosen depending on the number N of data points and the amount of random fluctuations in the data (the size of the random component in the data). In our examples we have chosen $N_c$=100 and $m_{min}$=3. The value of m can be redefined iteratively at the later stages and its choice will be discussed therein. Next we compute the moving average for $\{t_i\}$ and $\{T_i\}$ data sets with the given averaging parameter m as follows:

$$<t_k>_m = \frac{1}{m}\sum_{i=1}^{m} t_{k+i}, \quad <T_k>_m = \frac{1}{m}\sum_{i=1}^{m} T_{k+i}. \quad (12.2)$$

The subscript m will be omitted below if m is fixed and no ambiguity can arise. The next step in our algorithm is the initial determination of a time interval on which the parabolic fit will be performed, (the parabolic fit interval). This step is represented in FIG. 16 by Box 2. We note that this data subset can be redefined at a later stage if a certain condition is not satisfied. In the current realization of our algorithm this region defined differently for $\{t_i,T_i^{RR}\}$ and $\{t_i,T_i^{QT}\}$ data sets. For the data set $\{t_i,T_i^{RR}\}$ the initial parabolic fit segment is defined as the data segment $\{t_i,T_i^{RR}\}$ with all sequential values of i between $i_1$ and $i_2$ where $i_1=n_{min}-\Delta m$ and $i_2=n_{min}+\Delta m$, and the integer parameters $n_{min}$ and $\Delta m$ are defined as follows. The number $n_{min}$ determines the time instant $t_{n_{min}}$ among the original set of time instants which is the closest to the minimum on the averaged data set $\{<t_i>,<T_i>\}$. In other words, $t_{n_{min}}$ is the nearest to the average time instant $<t_M>$ which corresponds to the minimum value of the average RR-interval $<T_i^{RR}>$, that is, the time instant with the subscript value M defined by the condition $$<T_M^{RR}> = \min_i\{<T_i^{RR}>\} \quad (12.3)$$

The value of $\Delta m$ is linked to the value of m by the condition $\Delta m=2m$. The link between $\Delta n$ and m arises from the requirement that the algorithm is stable and consistent. The consistency is the requirement that the positions of the minimum of the curve obtained by moving averaging and by quadratic fitting were approximately the same. On the other hand, it is also important that the value of m is sufficiently small because quadratic fitting is done with the purpose to describe the data only locally in the immediate vicinity of the minimum.

For the data set $\{t_i,T_i^{QT}\}$ the initial parabolic fit segment is defined as the data subset that consists of all consecutive points belonging to the lower portion of the non-averaged $\{T_i^{QT}\}$ data set. We thus define $i_1$ as the first (minimum) number i such that $$T_i^{QT} \leq \min_j(T_j^{QT}) + R\left[\max_j(T_j^{QT}) - \min_j(T_j^{QT})\right] \quad (12.4)$$

where R is a parameter, 0<R<1, that determines the portion of the data to be fitted with the quadratic parabola. In our calculations we set R=⅛=0.125, so we fit with the parabola the data points that correspond to the bottom 12.5% of the interval durations. Thus, the subscript $i_1$, is the first (smallest) value of i such that condition (12.4) is satisfied. Similarly, $i_2$ is the last (greatest) value of i such that condition (12.4) is satisfied. The initial fit region is then defined as the following non-averaged data subset: $\{(t_i,T_i^{TQ}):i=i_1, i_1+1, i_1+2, \ldots, i_2\}$. This method can also be used for determining an initial data segment for the quadratic polynomial fitting of the RR-data set.

At the next step, shown by box 3 in FIG. 12.2, we fit the data in this region (for each data set) by a parabola so that the data are approximately represented by the equation $$T_k \approx P_1 t_k^2 + P_2 t_k + P_3, \quad k=j_1, j_1+1, j_1+2, \ldots, j_2. \quad (12.5)$$

This is done using usual linear regression on this data subset. At the next step (Box 4 in FIG. 16) we check if the parabola has a minimum (i.e., if $P_1>0$). If this condition is satisfied, the determination of the parabolic fit interval and the fitting parabola itself is completed. Otherwise, we enter the loop indicated by boxes 1a through 3a in FIG. 16. The first step there is similar to the above second step utilized for the RR interval data set and defines an extended segment for the parabolic fitting. This is done by replacing m with m+1 and using this new value of m to redefine $\Delta m=2m$ and also calculate new averaged data sets in accordance with Eq. (12.2) as indicated by Box 1a in FIG. 16. This allows us to evaluate a new value of $n_{min}$ and new values of $i_1=n_{min}-\Delta m$ and $i_2=n_{min}+\Delta m$ with new value of m (Box 2a). Then the parabolic fit is done again (Box 3a) and the condition $P_1>0$, that the parabola has a minimum, is checked again. If it is satisfied, the determination of the fit interval and the quadratic fit coefficients procedure is completed. Otherwise we replace m with m+1 and repeat the process again and again until the condition $P_1>0$ is satisfied. This condition ensures that the extremum of the quadratic parabola is a minimum indeed. By the very design of the exercise protocol the average heart rate reaches a certain maximum somewhere inside the load stage and therefore corresponding average RR-interval reaches a minimum. This ensures that a so-defined data segment exists and is unique, and therefore the coefficients of the quadratic parabola are well defined. In short, we use the shortest data segment that is centered around the minimum of the averaged data set and that generates a quadratic parabola with a minimum ($P_1>0$).

The parabolic fit defines two important parameters of the data processing procedure, the position ($t_{min},T_{min}$) of the minimum on the (t,T)-plane as follows $$t_{min} = -\frac{P_2}{2P_1}, \quad T_{min} = P_3 - \frac{P_2^2}{4P_1}. \quad (12.6)$$

These parameters are final in the sense that our final fit curve will always pass through and have a minimum at the point ($t_{min}$, $T_{min}$). The coordinates ($t_{min}$, $T_{min}$) thus constitute parameters of our final fit bird-like curve. Having found the ordinate $T_{min}$ of the minimum we can renormalization of the T-data set as follows:

$$y_k = \frac{T_k}{T_{\min}}. \tag{12.7}$$

We also take the abscissa of the parabola's minimum $t_{min}$ as the time origin and define the time components of the data points as follows $$t_i^- = t_i - t_{min}, \ t_i \leq 0,$$

$$t_j^+ = t_j - t_{min}, \ t_j > 0 \tag{12.8}$$

These two data transformations are indicated by Box 5 in FIG. 16. We also restrict the data set only to the exercise period, plus some short preceding and following intervals (Box 5). The conditions $t_i^- \leq 0$, and $t_j^+ > 0$ define the descending, $\{t_i^-, T_i\}$, and ascending, $\{t_j^+, T_j\}$, branches, respectively, so the corresponding data points can be readily identified and separated (Box 6). Given the durations $t_d$ and $t_a$ of the descending and ascending load stage, respectively, we can reduce the original set by cutting off the points on the descending branch with $t_i^- < -t_d$ and the points on the ascending branch with $t_j^+ > t_a$ (Box 6 in FIG. 16). This determines the minimum value $i_0$ of subscript i for the descending branch, and the maximum value $j_{max}$ of subscript j on the ascending branch.

The final step of the preliminary data processing is the conditional sorting (Box 7). The conditional sorting removes all consecutive points such that at least one of them falls below the minimum of the parabola. The removal of the points below the minimum is necessary because the nonlinear transformation is possible only when $y_i \geq 1$. Eliminating only separate points below the minimum y=1 would create a bias in the data. Therefore, we have to eliminate an entire segment of the data in the vicinity of the minimum. It should be remembered though, that these points have already been taken into account in the above quadratic filtering procedure that determines ($t_{min}$, $T_{min}$) via Eq. (12.6).

Thus, the preliminary data processing results in two data sets corresponding to the descending and ascending load stages. The descending data set is defined as a set of consecutive pairs $(t_i^-, y_i) \equiv (t_i^-, y_i^-)$ with $i = i_0, i_0+1, i_0+2, \ldots, i_{max}$, where $i_{max}$ is determined by the conditional sorting as the largest subscript i value still satisfying the condition $y_i \geq 1$. Similarly, the ascending data set is defined as a set of consecutive pairs $(t_i^+, y_i) \equiv (t_i^+, y_i^+)$ with $j = j_{min}, j_0+1, j_0+2, \ldots, j_{max}$, where $j_{min}$ is determined by the conditional sorting as the first subscript; value on the ascending branch starting from which the condition $y_j \geq 1$ is satisfied for all subsequent j.

2. Secondary data processing. At the second stage we introduce a fundamentally new method of nonlinear regression by means of two consecutive optimal nonlinear transformations. The idea of the method is to introduce for each branch two appropriate nonlinear transformations of the dependent and independent variables, $y = f(u)$ and $u = \phi(t)$, both transformations depending on some parameters, and choose the values of the parameters in such a way that the composition of these transformations $f(\phi(t_i))$ would provide an approximation for $y_i$. Let $(t_i^-, y_1^-)$ and $(t_i^+, y_i^+)$ be the cut, conditionally sorted and normalized data set corresponding to the descending and ascending branches representing the dynamics of the RR- or QT-intervals during exercise. The nonlinear transformation $y \Rightarrow u$ is defined via a smooth function $$y = f_\gamma(u), \tag{12.9}$$

that has a unit minimum at u=1, so that $f_\gamma(1)=1$, $f_\gamma'(1)=0$, and $f_\gamma(u)$ grows monotonously when $u \geq 1$ and decreases monotonously when $u \leq 0$. The subscript $\gamma$ represents a set of discrete or continuous parameters and indicates a particular choice of such a function. Let us denote by $f_\gamma^-(u)$ the monotonously decreasing branch of $f_\gamma(u)$ and its monotonously increasing branch, by $f_\gamma^+(u)$. We can thus write $$f_\gamma(u) = \begin{cases} f_\gamma^-(u), \text{ when } u \leq 1, \\ f_\gamma^+(u), \text{ when } u \geq 1. \end{cases} \tag{12.10}$$

Let $u = g_\gamma^+(y)$ and $u = g_\gamma^-(y)$ be the inverse functions for the respective branches of $f_\gamma(u)$. The functions $g_\gamma^+(y)$ and $f_\gamma^+(u)$ are monotonously increasing, while the functions $g_\gamma^-(y)$ and $f_\gamma^-(u)$ are monotonously decreasing. Let $\{t_i, y_i^-\}$ represent the data for the descending segment of the data set, i.e. $t_i < t_{min}$, and $\{t_i, y_i^+\}$ represent the data for the ascending segment of the data set i.e. for $t_i > t_{min}$. The transformation $$u_{\gamma,i}^- = g_\gamma^-(y_i^-) \tag{12.11}$$

maps the monotonously decreasing (on the average) data set $\{t_i, y_i^-\}$ into a monotonously increasing one:

$$\{t_i, y_i^-\} \Rightarrow \{t_i, g_\gamma^-(y_i^-)\} \equiv \{t_i, u_{\gamma,i}^-\}. \tag{12.12}$$

Moreover, the average slope of the original data set is decreasing as $t_i$ approaches $t_{min}$ and eventually vanishing at the minimum. In contrast, the average slope of the transformed data set is always nonzero at $t = t_{min}$. Similarly, the transformation $$u_{\gamma,j}^+ = g_\gamma^+(y_j^+) \tag{12.13}$$

maps the monotonously increasing (on the average) data set $\{t_i, y_i^+\}$ into a monotonously increasing one:

$$\{t_j, y_j^+\} \Rightarrow \{t_j, g_\gamma^+(y_j^+)\} \equiv \{t_j, u_{\gamma,j}^+\}. \tag{12.14}$$

In our examples we used a discrete parameter $\gamma$ taking two values $\gamma=1$ and $\gamma=2$ that correspond to two particular choices of the nonlinear y-transformation. The first case ($\gamma=1$) is described by the equations $$y = f_1(u) \equiv 1 + (u-1)^2; \ u^- = g_1^-(y) \equiv y - \sqrt{y^2-1}, \ u^+ = g_1^+(y)$$
$$= y + \sqrt{y^2-1}. \tag{12.15}$$

The second case, $\gamma=2$, is described by the equations $$y = f_2(u) \equiv u + \frac{1}{u}; \tag{12.16}$$

$$u^- = g_2^-(y) \equiv 1 - \sqrt{y-1}, \ u^+ = g_2^+(y) \equiv 1 + \sqrt{y-1}.$$

Both functions reach a minimum y=1 at u=1. An example of such a function depending on a continuous parameter γ>0 is given by $$f_\gamma(u) = A_\gamma \left\{ \frac{1}{\gamma^2 + b_\gamma u} + \frac{\gamma^2 b_\gamma u}{\gamma^2 b_\gamma u + 1} \right\}, b_\gamma \equiv 1 + \gamma + \frac{1}{\gamma}. \quad (12.17)$$

The parameter $b_\gamma$ has been determined from the condition that $f\gamma(u)$ has a minimum at u=1 and the coefficient $A_\gamma$ is determined by the condition $f_\gamma(1)=1$, which yields $$A_\gamma = \frac{\gamma^3 + \gamma^2 + \gamma + 1}{\gamma^3 + \gamma^2 + 2\gamma} \quad (12.18)$$

Figure 17A:
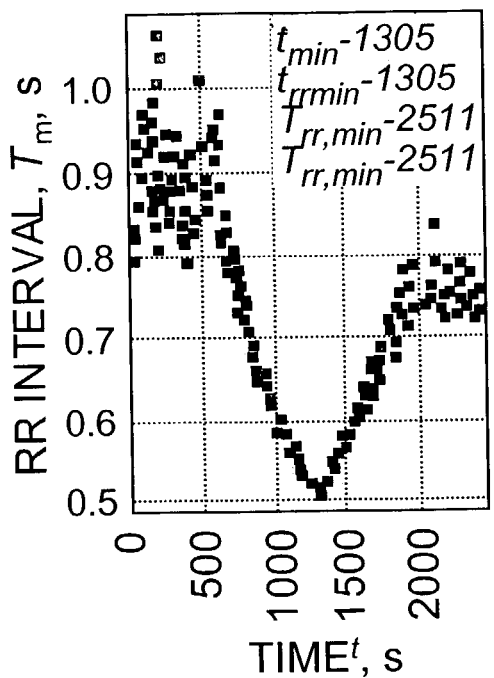
FIG. 17 displays the nonlinear transformation of a filtered RR-interval data set. Panel A shows the data on the original (t,y)-plane, the minimum is marked with an asterisk inside a circle. Panels B and C show the transformed sets on the (t,u)-plane, for j=1 and for j=2, respectively. The image of the minimum is also marked with an encircled asterisk. Note that the transformed data sets concentrate around a monotonously growing (average) curve with a clearly linear portion in the middle.
Figure 17B:
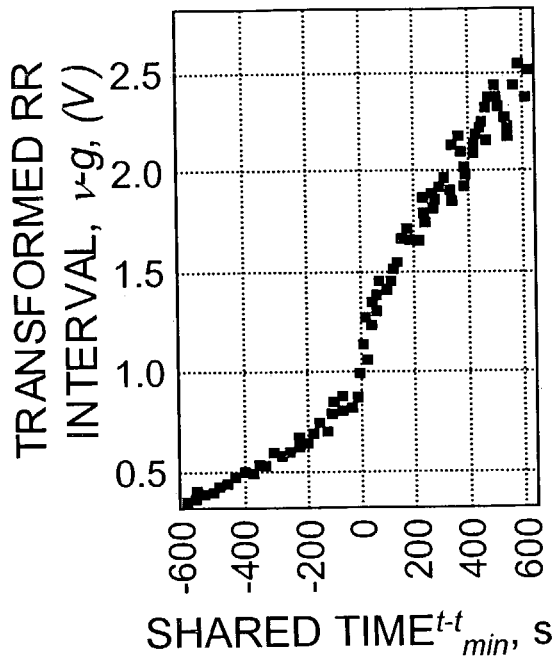
Figure 17C:
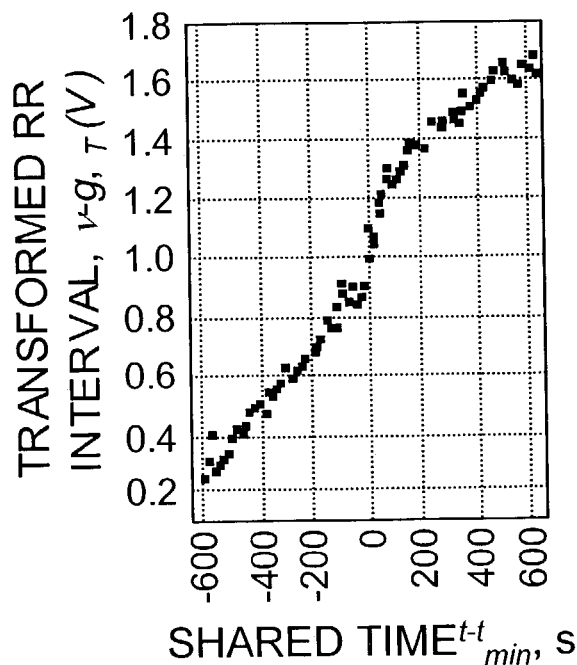
Figure 18A:
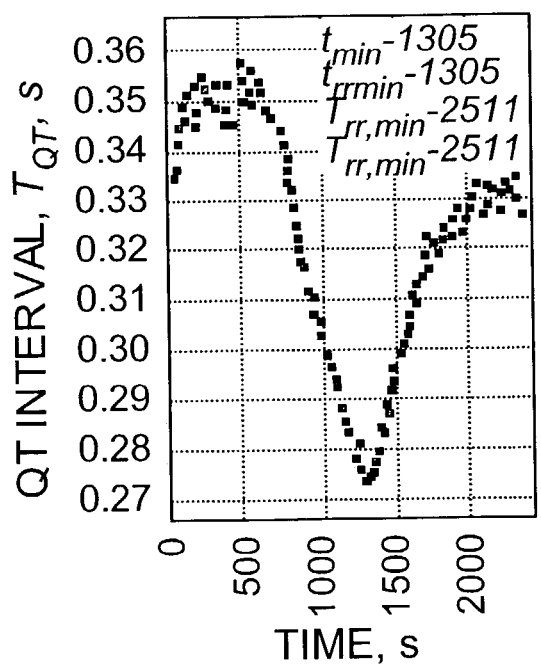
FIG. 18 is similar to FIG. 17 but for a QT-interval data set.
Figure 18B:
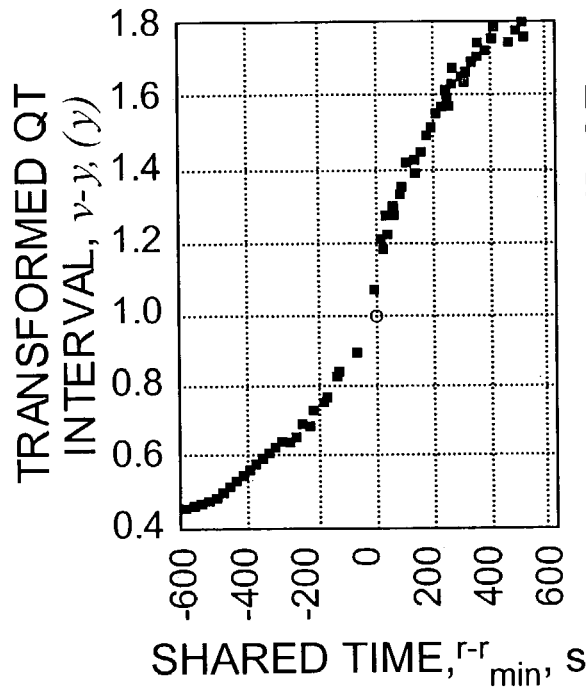
Figure 18C:
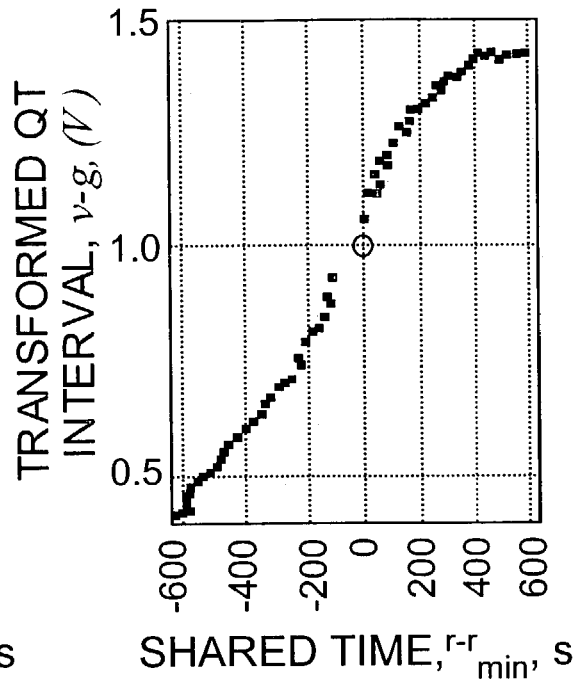

In our numerical examples below we utilize the discrete parameter case with γ taking two values, 1 and 2. The original and transformed sets are shown in FIGS. 17 (RR intervals) and 18 (QT-intervals). Panels A in both figures show the original data sets on the (t,T)-plane and panels B and C show the transformed sets on the (t,u)-plane, for γ=1 and for γ=2, respectively. The parabola minima on panels A and C are marked with a circled asterisk. The original data points concentrate near a non-monotonous curve (the average curve). The data points on the transformed plane concentrate around a monotonously growing (average) curve. Moreover, the figure illustrates that the transformation changes the slope of the average curve in the vicinity of $t=t_{min}$ from zero to a finite, nonzero value. On the $(t-t_{min}, u)$-plane the point corresponding to the parabola's minimum is (0,1). This point is also marked by a circled asterisk on panels B and C of FIGS. 17 and 18.

Let us introduce a pair of new time variables $\tau^-$ and $\tau^+$ for the descending and ascending branches, respectively. We shall count them off from the abscissa of the minimum of the fitted parabola and set $$\tau_i^- = t_{min} - t_i, \; t_i \leq t_{min}, \; i=1, 2, \ldots, I^-$$

$$\tau_j^+ = t_j - t_{min}, \; t_j \geq t_{min}, \; j=1, 2, \ldots, J^+ \quad (12.19)$$

where $I^-$ and $J^+$ are the number of data points on the descending and ascending branches, respectively. The (formerly) descending branch can be treated in exactly the same way as the ascending one if simultaneously with the time inversion given by the first line in Eq. (12.19) we perform an additional transformation of the descending branch ordinates as follows $$v_k = 1 - u_k^-. \quad (12.20)$$

In these variables both branches $(\tau_i^-, v_i)$ and $(\tau_j^+, u_j^+)$ are monotonously growing and start from the same point (τ=0, u=1) at which both have nonzero slope and possess similar behavior (convexity).

Since both branches are treated in exactly the same way, we shall simplify the notation and temporarily omit the superscripts ± and write $(\tau_k, u_k)$ for any of the pairs $(\tau_i^-, v_i)$ or $(\tau_j^+, u_j^+)$. We shall fit the data set $\{u_k\}$ with $\{\phi(\alpha, \beta, \tau_k)\}$, that is represent $\{u_k\}$ as $$u_k \approx \phi(\alpha, \beta, K, \tau_k) \quad (12.21)$$

where the function φ depends linearly on K and is defined as $$\phi(\alpha, \beta, K, \tau) = 1 + K\xi(\alpha, \beta, t) \quad (12.22)$$

where $$\xi(\alpha, \beta, \tau) = \begin{cases} \frac{\alpha}{\beta}\left(1 + \frac{\tau}{\alpha}\right)^\beta & \text{when } \beta > 0 \\ s \equiv \alpha \ln\left(1 + \frac{\tau}{\alpha}\right) & \text{when } \beta = 0 \\ \frac{\alpha}{1+\beta}\left[\left(1 + \frac{s}{\alpha}\right)^{1+\beta} - 1\right] & \text{when } -1 \leq \beta < 0 \end{cases} \quad (12.23)$$

Figure 19:
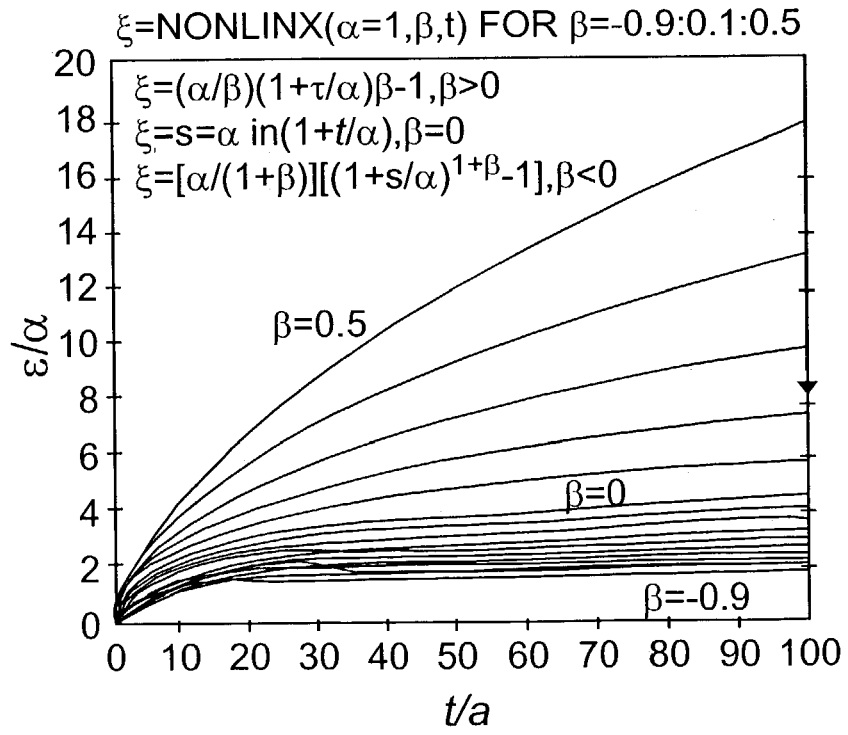
FIG. 19 displays an appropriately scaled representation for the family of functions $\xi(\alpha, \beta, \tau)$ for fifteen values of parameter $\beta$ varying with the step $\Delta\beta=0.1$ from $\beta=-0.9$ (lower curve) through $\beta=0$ (medium, bold curve), to $\beta=0.5$ (upper curve). The function $\xi(\alpha, \beta, \tau)$ is continuous in all three variables and as a function of $\tau$ has a unit slope at $\tau=0$, $\xi'(\alpha, \beta, 0)=1$.
Figure 20A:
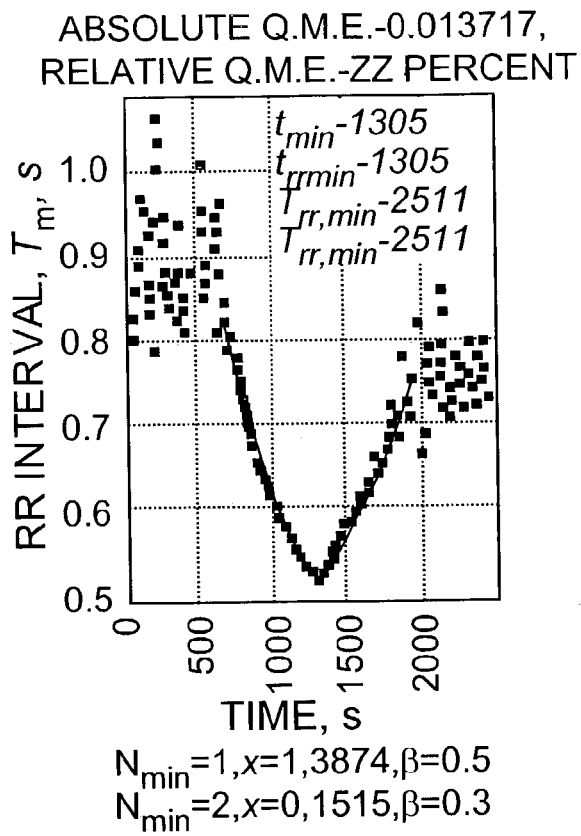
FIG. 20 shows an example of full processing of the RR and QT data sets for one patient. Panels A and C represent RR and QT data sets and their fit. Panel B shows the corresponding ascending and descending curves and closing line on the $(T_{RR}, T_{QT})$-plane, on which the area of such a hysteresis loop has the dimension of time-squared. Panel D shows a hysteresis loop on the $(f_{RR}, T_{QT})$-plane, where $f_{RR}=1/T_{RR}$ is the heart rate, on which the loop area is dimensionless. The total error for Panel A is 2.2% and for Panel C is 0.8%.
Figure 20B:
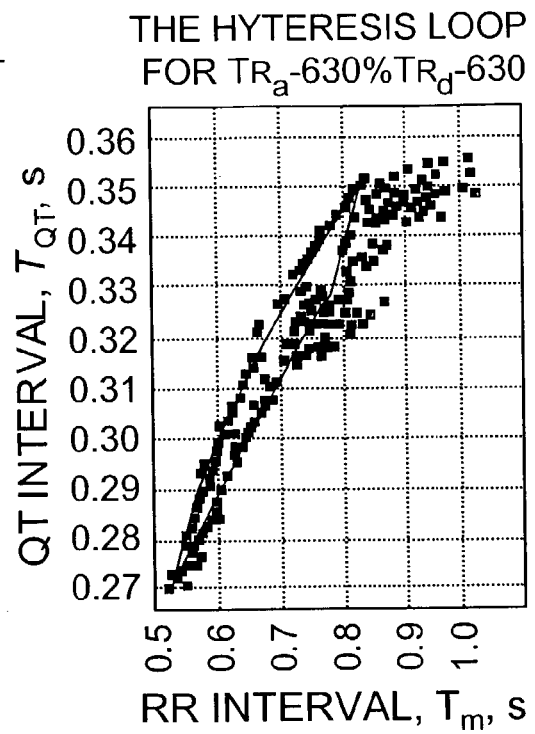
Figure 20C:
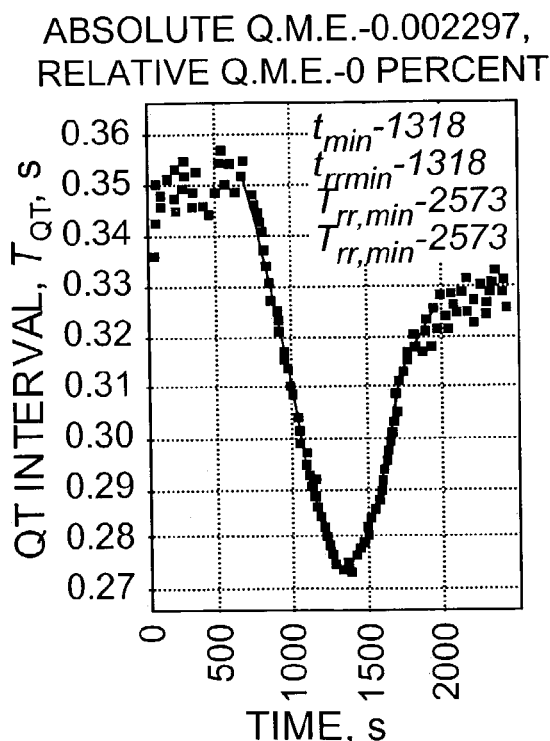
Figure 20D:
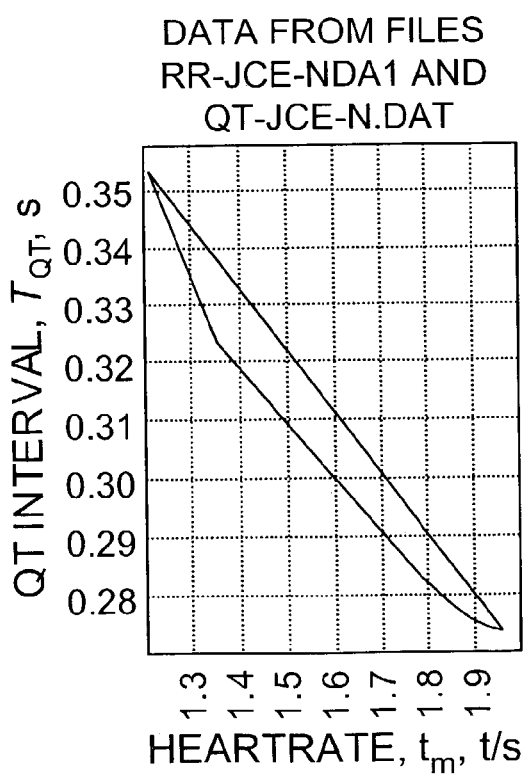

A family of functions $\xi(\alpha, \beta, \tau)$ is shown in FIG. 19 for fifteen values of parameter β. The parameter α is completely scaled out by plotting the function on the plane (τ/α,ε/α). The function $\xi(\alpha, \beta, \tau)$ is continuous in all three variables and as a function of τ at fixed α and β has a unit slope at τ=0, $\xi'(\alpha, \beta, 0)=1$. Therefore, at τ→0 the function ξ possesses a very simple behavior, ξ~τ, which is independent of α and β (the size of the region of such behavior of course depends on α and β). The function ξ possesses the following important feature: when β passes through the point β=0, its asymptotic behavior at τ→∞ continuously changes from the power function, ξ~τ^β at β>0, through ξ~ln(τ) at β=0, to a power of the logarithm, ξ~ln^{1+β}(τ) when −1<β<0. When β→−1, the behavior of ξ changes once more, and becomes ξ~ln(ln(τ)). The convexity of any function of the family is the same when β<1.

We shall explicitly express parameter K via α and β using the requirement for a given pair of α and β Eq-s. (12.22) and (12.23) ensure the best data fit in the u-space in a certain vicinity of the point (τ=0,u=1). Let $K_1$ be the number of points where the fit is required. The corresponding quadratic error is then a function of K, α and β that can be written as $$\varepsilon^{(u)}(K, \alpha, \beta) = \sum_{k \leq K_1} [u_k - K\varphi(\alpha, \beta, T_k)]^2 \quad (12.24)$$

and the requirement of its minimum immediately yields the following expression for K $$K = K(\alpha, \beta) \equiv \frac{\sum_{k \leq K_1} u_k \varphi(\alpha, \beta, \tau_k)}{\sum_{k \leq K_1} \varphi^2(\alpha, \beta, \tau_k)} \quad (12.25)$$

In our calculations we used such $K_1$ value that would include all adjacent points with the values of u between u=1 and u=1+0.4 ($u_{max}$−1). We have thus reduced the number of fitting parameters in our fitting procedure to two continuous parameters, α and β, and one discrete parameter, γ. The fitting function thus becomes $$y_k \approx f_\gamma(1 + K(\alpha, \beta)\xi(\alpha, \beta, \tau_k)) \quad (12.26)$$

The values of parameters α, β and K (and γ) are now directly determined by the condition that the fit error in the y-space $$\varepsilon_\gamma^{(y)}(\alpha, \beta) = \sum_k [y_k - f_\gamma(1 + K(\alpha,\beta)\varphi(\alpha,\beta,\tau_k))]^2 \quad (12.27)$$

is minimum. The sum in Eq. (12.27) is evaluated numerically on a grid (α,β) values for γ equal 1 and 2. Then the values of α,β and γ that deliver a minimum to $\epsilon_\gamma^{(y)}$ are found via numerical trials. Calculations can then be repeated on a finer grid in the vicinity of the found minimum.

Having found parameters $\alpha_{min}$, $\beta_{min}$ and $\gamma_{min}$ for the ascending branch we generate a dense t-grid $\{t_s, s=1, 2, \ldots, N\}$ and calculate the corresponding values of the interval duration as $$T_s = T_{min} f_{\gamma di\ min}(1 + K(\alpha_{min}, \beta_{min})\xi(\alpha_{min}, \beta_{min}, t_s - t_{min})) \quad (12.28)$$

A similar dense representation of the descending branch can be calculated in exactly the same way. The resulting bird-like curves are illustrated in panels A and C of FIG. 20. The actual absolute and relative errors are indicated in the captions. The right hand side panels B and D represent hysteresis curves in two different representations and each resulting from the curves shown in Panels A and C. The following computations of the hysteresis loop and its measure given by Eq. (10.17) is then performed as described in Example 11.

EXAMPLE 14

Creation of an RR-Hysteresis Loop With the Procedures of Examples 10–12

In addition to the procedures generating a hysteresis loop on the plane (QT-interval versus RR-interval) or an equivalent plane, one can introduce and assess a separate hysteresis of the duration of RR-interval versus exercise work load, which gradually varies, there-and-back, during the ascending and descending exercise stages. The RR-hysteresis can be displayed as loops on different planes based on just a single RR data set $\{t_{RR}^i, T_{RR}^i\}$ analysis. For example, such a loop can be displayed on the $(\tau^i, T_{RR}^i)$-plane, where $\tau^i = |t_{RR}^i - t_{min}|$ and $t_{min}$ is the time instant corresponding to the peak of the exercise load, or the center of the maximum load period, which may be determined according to numerical techniques described in the examples 10–12. The RR loop can also be introduced on the $(W(t_{RR}^i), T_{RR}^i)$ or $(\tau^i, (T_{RR}^i)^{-1})$ planes. Here $W(t_{RR}^i)$ is a work load that varies versus exercise stages, i.e. time and $(T_{RR}^i)^{-1}$ represents the heart rate.

In order to apply a numerical technique from the Example 11 (or any other as in Examples 11 or 12), one repeats essentially the same computational steps described in these examples. However, instead of considering both QT-$\{t_{QT}^i, T_{QT}^i\}$ and RR-$\{t_{RR}^i, T_{RR}^i\}$ interval data sets, only a single RR data set is numerically processed throughout the whole sequence of the described stages for a creation of a hysteresis loop. In this case variables $\tau^i$, $(T_{RR}^i)^{-1}$ or $W(t_{RR}^i)$ play the role of the second alternating component that along with the first $T_{RR}^i$ variable forms the RR-hysteresis plane.

The foregoing examples are illustrative of the present invention and are not to be construed as limiting thereof. The invention is defined by the following claims, with equivalents of the claims to be included therein.

That which is claimed is:

1. A method of assessing cardiac ischemia in a subject to provide a measure of cardiac or cardiovascular health in that subject, said method comprising the steps of:
   (a) collecting a first RR-interval data set from said subject during a stage of gradually increasing heart rate up to a predetermined threshold of at least 130 beats per minute;
   (b) collecting a second RR-interval data set from said subject during a stage of gradually decreasing heart rate;
   (c) comparing said first RR-interval data set to said second RR-interval data set to determine the difference between said data sets; and
   (d) generating from said comparison of step (c) a measure of cardiac ischemia in said subject, wherein a greater difference between said first and second data sets indicates greater cardiac ischemia and lesser cardiac or cardiovascular health in said subject.

2. The method according to claim 1, wherein the predetermined threshold rate is defined by the formula $$PT = (220 \pm V\ \text{bpm}) - \text{age};$$

where PT is the predetermined threshold heart rate, V is 20, bpm is beats per minute, and age is the age of said subject.

3. The method according to claim 2, wherein said first and second QT-interval data sets are collected under quasi-stationary conditions.

4. The method according to claim 1, further comprising:
   (e) concurrently with steps (a) and (b), collecting a first and second QT-interval data set from said subject;
   (f) comparing said first QT-interval data set to said second QT-interval data set to determine the difference between said data sets; and
   (g) generating from said comparison step (f) a measure of cardiac ischemia during stimulation in said subject, wherein a greater difference between said first and second data sets indicates greater cardiac ischemia and lesser cardiac or cardiovascular health in said subject.

5. The method according to claim 1, further comprising performing the method on a subject not afflicted with coronary artery disease.

6. The method according to claim 1, further comprising performing the method on a subject afflicted with coronary artery disease.

7. The method according to claim 1, further comprising performing the method on a subject afflicted with moderate coronary artery disease.

8. The method according to claim 1, wherein said first and second RR-interval data sets are collected under quasi-stationary conditions.

9. The method according to claim 1, wherein said stage of gradually increasing heart rate and said stage of gradually decreasing heart rate are each at least 3 minutes in duration.

10. The method according to claim 1, wherein said stage of gradually increasing heart rate and said stage of gradually decreasing heart rate are together carried out for a total time of from 6 minutes to 40 minutes.

11. The method according to claim 1, wherein:
   both said stage of gradually increasing heart rate and said stage of gradually decreasing heart rate are carried out between a peak rate and a minimum rate; and
   said peak rates of both said stage of gradually increasing heart rate and said stage of gradually decreasing heart rate are the same.

12. The method according to claim 11, wherein:
   said minimum rates of both said stage of gradually increasing heart rate and said stage of gradually decreasing heart rate are substantially the same.

13. The method according to claim 1, wherein said stage of gradually decreasing heart rate is carried out at at least three different heart-rate levels.

14. The method according to claim 13, wherein said stage of gradually increasing heart rate is carried out at at least three different heart-rate levels.

15. The method according to claim 1, wherein said stage of gradually increasing heart rate and said stage of gradually decreasing heart rate are carried out sequentially in time.

16. The method according to claim 1, wherein said stage of gradually increasing heart rate and said stage of gradually decreasing heart rate are carried out separately in time.

17. The method according to claim 1, wherein said generating step is carried out by generating curves from each of said data sets.

18. The method according to claim 17, wherein said generating step is carried out by comparing the shapes of said curves from data sets.

19. The method according to claim 17, wherein said generating step is carried out by determining a measure of the domain between said curves.

20. The method according to claim 17, wherein said generating step is carried out by both comparing the shapes of said curves from data sets and determining a measure of the domain between said curves.

21. The method according to claim 17, further comprising the step of displaying said curves.

22. The method according to claim 1, wherein said heart rate during said stage of gradually increasing heart rate exceeds 150 beats per minute.

23. The method according to claim 1, further comprising the step of:
(e) comparing said measure of cardiac ischemia during stimulation to at least one reference value; and then
(f) generating from said comparison of step (e) a quantitative indicium of cardiac or cardiovascular health for said subject.

24. The method according to claim 23, further comprising the steps of:
(g) treating said subject with a cardiovascular therapy; and then
(h) repeating steps (a) through (f) to assess the efficacy of said cardiovascular therapy, in which a decrease in the difference between said data sets from before said therapy to after said therapy indicates an improvement in cardiac health in said subject from said cardiovascular therapy.

25. The method according to claim 24, wherein said cardiovascular therapy is selected from the group consisting of aerobic exercise, muscle strength building, change in diet, nutritional supplement, weight loss, stress reduction, smoking cessation, pharmaceutical treatment, surgical treatment, and combinations thereof.

26. The method according to claim 23, further comprising the step of assessing from said quantitative indicium the likelihood that said subject is at risk to experience a future ischemia-related cardiac incident.

27. A computer program product for assessing cardiac ischemia in a subject to provide a measure of cardiac or cardiovascular health in that subject, said computer program product comprising a computer usable storage medium having computer readable program code embodied in the medium, the computer readable program code comprising:
(a) computer readable program code for collecting a first RR-interval data set from said subject during a stage of gradually increasing heart rate up to a predetermined threshold of at least 130 beats per minute;
(b) computer readable program code for collecting a second RR-interval data set from said subject during a stage of gradually decreasing heart rate;
(c) computer readable program code for comparing said first RR-interval data set to said second RR-interval data set to determine the difference between said data sets; and
(d) computer readable program code for generating from said comparing in said computer readable program code (c) a measure of cardiac ischemia in said subject, wherein a greater difference between said first and second data sets indicates greater cardiac ischemia and lesser cardiac or cardiovascular health in said subject;
(e) computer readable program code for comparing said measure of cardiac ischemia during stimulation to at least one reference value; and
(f) computer readable program code for generating from said comparison of (e) a quantitative indicium of cardiac or cardiovascular health for said subject.

28. The computer program product of claim 27, further comprising:
(g) computer readable program code for concurrently with steps (a) and (b), collecting a first and second QT-interval data set from said subject;
(h) computer readable program code for comparing said first QT-interval data set to said second QT-interval data set to determine the difference between said data sets at step; and
(i) computer readable program code for generating from said comparing in said computer readable program code (h) a measure of cardiac ischemia in said subject, wherein a greater difference between said first and second data sets indicates greater cardiac ischemia and lesser cardiac or cardiovascular health in said subject.

29. The computer program product of claim 27, wherein said computer readable program code for generating includes computer readable program code for generating curves from each of said data sets.

30. The computer program product of claim 29, wherein said computer readable program code for generating (i) includes computer readable program code for comparing the shapes of said curves from data sets.

31. The computer program product of claim 29, wherein said computer readable program code for generating (i) includes computer readable program code for determining a measure of the domain between said curves.

32. The computer program product of claim 29, wherein said computer readable program code for generating (i) includes computer readable program code for comparing the shapes of said curves from data sets and determining a measure of the domain between said curves.

33. The computer program product of claim 29, further comprising computer readable program code for displaying said curves.

34. The computer program product of claim 27, further comprising computer readable program code for assessing from said quantitative indicium the likelihood that said subject is at risk to experience a future ischemia-related cardiac incident.

35. A system for assessing cardiac ischemia in a subject to provide a measure of cardiac or cardiovascular health in that subject, comprising:
(a) means for collecting a first RR-interval data set from said subject during a stage of gradually increasing heart rate up to a predetermined threshold of at least 130 beats per minute;
(b) means for collecting a second RR-interval data set from said subject during a stage of gradually decreasing heart rate;
(c) means for comparing said first RR-interval data set to said second RR-interval data set to determine the difference between said data sets; and (d) means for generating from said means for comparing (c) a measure of cardiac ischemia in said subject, wherein a greater difference between said first and second data sets indicates greater cardiac ischemia and lessor cardiac or cardiovascular health in said subject (e) means for generating said measure of cardiac ischemia to at least one reference value; and (f) means for generating from said comparison of (e) a quantitative indicium of cardiac or cardiovascular health for said subject.

36. The system of claim 35, further comprising:

(g) means for concurrently with steps (a) and (b), collecting a first and second QT-interval data set from said subject;

(h) means for comparing said first QT-interval data set to said second QT-interval data set to determine the difference between said data sets; and (i) means for generating from said comparing a measure of cardiac ischemia in said subject, wherein a greater difference between said first and second data sets indicates greater cardiac ischemia and lesser cardiac or cardiovascular health in said subject.

37. The system of claim 35, wherein said means for generating (i) includes means for generating curves from each of said data sets.

38. The system of claim 37, wherein said means for generating (i) includes means for comparing the shapes of said curves from data sets.

39. The system of claim 37, wherein said means for generating includes means for determining a measure of the domain between said curves.

40. The system claim 37, wherein said means for generating (i) includes means for comparing the shapes of said curves from data sets and determining a measure of the domain between said curves.

41. The system of claim 37, further comprising means for displaying said curves.

42. The system of claim 35, further comprising:

(e) means for comparing said measure of cardiac ischemia during stimulation to at least one reference value; and (f) means for generating from said comparison of (e) a quantitative indicium of cardiac or cardiovascular health for said subject.

43. The system of claim 42, further comprising means for assessing from said quantitative indicum the likelihood that said subject is at risk to experience a future ischemia-related cardiac incident.

* * * * *

UNITED STATES PATENT AND TRADEMARK OFFICE
CERTIFICATE OF CORRECTION

PATENT NO.        : 7,104,961 B2                                   Page 1 of 1
APPLICATION NO.   : 10/308639
DATED             : September 12, 2006
INVENTOR(S)       : Starobin et al.

It is certified that error appears in the above-identified patent and that said Letters Patent is hereby corrected as shown below:

<u>Column 41,</u>

Lines 5-6 should read -- lesser cardiac or cardiovascular health in said subject (e) means for comparing said measure of cardiac ischemia --

<u>Column 42,</u>

Lines 14-19 (Claim 42) should be deleted.

Line 20 should read -- 42. The system of claim 35, further comprising means for --

Signed and Sealed this

Tenth Day of July, 2007

JON W. DUDAS
*Director of the United States Patent and Trademark Office*